(12) United States Patent
Edman et al.

(10) Patent No.: US 6,780,584 B1
(45) Date of Patent: Aug. 24, 2004

(54) ELECTRONIC SYSTEMS AND COMPONENT DEVICES FOR MACROSCOPIC AND MICROSCOPIC MOLECULAR BIOLOGICAL REACTIONS, ANALYSES AND DIAGNOSTICS

(75) Inventors: Carl F. Edman, San Diego, CA (US); Eugene Tu, San Diego, CA (US); Christian Gurtner, La Jolla, CA (US); Lorelei Westin, San Diego, CA (US); Michael J. Heller, Encinitas, CA (US)

(73) Assignee: Nanogen, Inc., San Diego, CA (US)

( * ) Notice: Subject to any disclaimer, the term of this patent is extended or adjusted under 35 U.S.C. 154(b) by 121 days.

(21) Appl. No.: 09/671,954

(22) Filed: Sep. 27, 2000

(51) Int. Cl.[7] .......................... C12Q 1/68; C12P 19/34; G01N 33/566; G01N 15/06
(52) U.S. Cl. ......................... 435/6; 435/91.2; 436/501; 422/50; 422/68.1
(58) Field of Search ................... 435/6, 31.2; 436/501; 422/50, 68.1

(56) References Cited

U.S. PATENT DOCUMENTS

| | | | |
|---|---|---|---|
| 3,902,986 A | 9/1975 | Nees et al. | |
| 4,589,965 A | 5/1986 | Kreisher et al. | |
| 4,787,963 A | 11/1988 | MacConnell | 204/180.1 |
| 4,936,963 A | * 6/1990 | Mandecki et al. | 204/468 |
| 5,605,662 A | 2/1997 | Heller et al. | 422/68.1 |
| 5,632,957 A | 5/1997 | Heller et al. | 422/68.1 |
| 6,017,696 A | 1/2000 | Heller | 435/6 |
| 6,051,380 A | 4/2000 | Sosnowski et al. | 435/6 |

* cited by examiner

Primary Examiner—Jeffrey Siew
Assistant Examiner—J. Tung
(74) Attorney, Agent, or Firm—O'Melveny & Myers LLP

(57) ABSTRACT

This invention pertains to the design, fabrication, and uses of an electronic system which can actively carry out and control multi-step and multiplex reactions in macroscopic or microscopic formats. In particular, these reactions include molecular biological reactions, such as nucleic acid hybridizations, nucleic acid amplification, sample preparation, antibody/antigen reactions, clinical diagnostics, combinatorial chemistry and selection, drug screening, oligonucleotide and nucleic acid synthesis, peptide synthesis, biopolymer synthesis and catalytic reactions. A key feature of the present invention is the ability to control the localized concentration of two or more reaction-dependant molecules and their reaction environment in order to greatly enhance the rate and specificity of the molecular biological reaction.

86 Claims, 12 Drawing Sheets

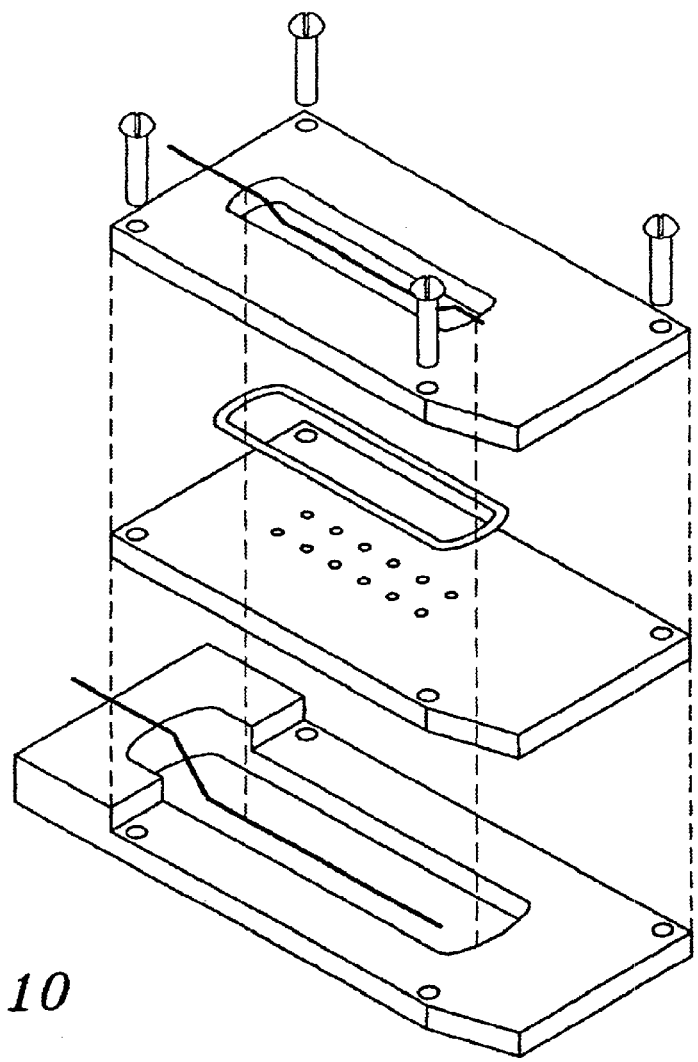
FIG. 10
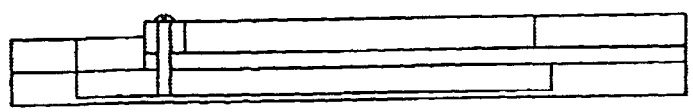
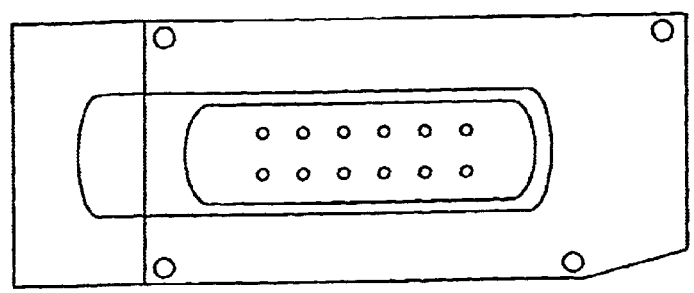

SEQUENCE LISTING

<160> NUMBER OF SEQ ID NOS: 17

<210> SEQ ID NO 1
<211> LENGTH: 19
<212> TYPE: DNA
<213> ORGANISM: Artificial Sequence
<220> FEATURE:
<223> OTHER INFORMATION: Capture oligonucleotide
<220> FEATURE:
<221> NAME/KEY: modified_base
<222> LOCATION: (1)..(1)
<223> OTHER INFORMATION: Base 1 modified with Biotin

<400> SEQUENCE: 1
gatgagcagt tctacgtgg					19

<210> SEQ ID NO 2
<211> LENGTH: 17
<212> TYPE: DNA
<213> ORGANISM: Artificial Sequence
<220> FEATURE:
<223> OTHER INFORMATION: Capture oligonucleotide
<220> FEATURE:
<221> NAME/KEY: modified_base
<222> LOCATION: (1)..(1)
<223> OTHER INFORMATION: Base 1 modified with Biotin

<400> SEQUENCE: 2
gtctccttcc tctccag					17

<210> SEQ ID NO 3
<211> LENGTH: 19
<212> TYPE: DNA
<213> ORGANISM: Artificial sequence
<220> FEATURE:
<223> OTHER INFORMATION: Reporter oligonucleotide
<220> FEATURE:
<221> NAME/KEY: modified_base
<222> LOCATION: (1)..(1)
<223> OTHER INFORMATION: Base 1 modified with Bodipy Texas Red

<400> SEQUENCE: 3
ccacgtagaa ctgctcatc					19

<210> SEQ ID NO 4
<211> LENGTH: 15
<212> TYPE: DNA
<213> ORGANISM: Artificial sequence
<220> FEATURE:
<223> OTHER INFORMATION: Capture oligonucleotide
<220> FEATURE:
<221> NAME/KEY: modified_base
<222> LOCATION: (1)..(1)
<223> OTHER INFORMATION: Base 1 modified with Biotin

<400> SEQUENCE: 4
cacaccggcg gcgcc					15

<210> SEQ ID NO 5
<211> LENGTH: 15
<212> TYPE: DNA
<213> ORGANISM: Artificial sequence
<220> FEATURE:
<223> OTHER INFORMATION: Capture oligonucleotide
<220> FEATURE:
<221> NAME/KEY: modified_base
<222> LOCATION: (1)..(1)
<223> OTHER INFORMATION: Base 1 modified with Biotin

```
<400> SEQUENCE: 5
cacaccgtcg gcgcc                                                    15

<210> SEQ ID NO 6
<211> LENGTH: 15
<212> TYPE: DNA
<213> ORGANISM: Artificial sequence
<220> FEATURE:
<223> OTHER INFORMATION: Reporter oligonucleotide
<220> FEATURE:
<221> NAME/KEY: modified_base
<222> LOCATION: (1)..(1)
<223> OTHER INFORMATION: Base 1 modified with Bodipy Texas Red

<400> SEQUENCE: 6
ggcgccgccg gtgtg                                                    15

<210> SEQ ID NO 7
<211> LENGTH: 18
<212> TYPE: DNA
<213> ORGANISM: Artificial sequence
<220> FEATURE:
<223> OTHER INFORMATION: Primer oligonucleotide
<220> FEATURE:
<221> NAME/KEY: modified_base
<222> LOCATION: (1)..(1)
<223> OTHER INFORMATION: Base 1 modified with Biotin

<400> SEQUENCE: 7
tgaaggataa gcagcaat                                                 18

<210> SEQ ID NO 8
<211> LENGTH: 18
<212> TYPE: DNA
<213> ORGANISM: Artificial sequence
<220> FEATURE:
<223> OTHER INFORMATION: Primer oligonucleotide

<400> SEQUENCE: 8
tcctctcaac ccccaata                                                 18

<210> SEQ ID NO 9
<211> LENGTH: 36
<212> TYPE: DNA
<213> ORGANISM: Artificial sequence
<220> FEATURE:
<223> OTHER INFORMATION: Reporter oligonucleotide
<220> FEATURE:
<221> NAME/KEY: modified_base
<222> LOCATION: (1)..(36)
<223> OTHER INFORMATION: Base 1 modified with Bodipy Texas Red

<400> SEQUENCE: 9 agggggctgat ccaggcctgg gtgctccacc tggcac                            36

<210> SEQ ID NO 10
<211> LENGTH: 21
<212> TYPE: DNA
<213> ORGANISM: Artificial sequence
<220> FEATURE:
<223> OTHER INFORMATION: Capture oligonucleotide
<220> FEATURE:
<221> NAME/KEY: modified_base
<222> LOCATION: (1)..(1)
<223> OTHER INFORMATION: Base 1 modified with Biotin

<400> SEQUENCE: 10
```

```
ttccacagac ttagatttga c                                              21
```

<210> SEQ ID NO 11
<211> LENGTH: 26
<212> TYPE: DNA
<213> ORGANISM: Artificial sequence
<220> FEATURE:
<223> OTHER INFORMATION: Capture oligonucleotide
<220> FEATURE:
<221> NAME/KEY: modified_base
<222> LOCATION: (1)..(1)
<223> OTHER INFORMATION: Base 1 modified with Biotin

<400> SEQUENCE: 11

```
gtgctgcagg tgtaaacttg tacgag                                         26
```

<210> SEQ ID NO 12
<211> LENGTH: 21
<212> TYPE: DNA
<213> ORGANISM: Artificial sequence
<220> FEATURE:
<223> OTHER INFORMATION: Reporter oligonucleotide
<220> FEATURE:
<221> NAME/KEY: modified_base
<222> LOCATION: (1)..(1)
<223> OTHER INFORMATION: Base 1 modified with Bodipy Texas Red

<400> SEQUENCE: 12

```
gtcaaatcta agtctgtgga a                                              21
```

<210> SEQ ID NO 13
<211> LENGTH: 42
<212> TYPE: DNA
<213> ORGANISM: Artificial sequence
<220> FEATURE:
<223> OTHER INFORMATION: Primer oligonucleotide
<220> FEATURE:
<221> NAME/KEY: modified_base
<222> LOCATION: (1)..(1)
<223> OTHER INFORMATION: Base 1 modified with Biotin

<400> SEQUENCE: 13

```
accgcatcga atgcatgtcc tcgggtctct gggctaatag ga                       42
```

<210> SEQ ID NO 14
<211> LENGTH: 42
<212> TYPE: DNA
<213> ORGANISM: Artificial sequence
<220> FEATURE:
<223> OTHER INFORMATION: Primer oligonucleotide
<220> FEATURE:
<221> NAME/KEY: modified_base
<222> LOCATION: (1)..(1)
<223> OTHER INFORMATION: Base 1 modified with Biotin

<400> SEQUENCE: 14

```
acgattcagc tccagacttc tcgggtcaga atttctgaaa gg                       42
```

<210> SEQ ID NO 15
<211> LENGTH: 20
<212> TYPE: DNA
<213> ORGANISM: Artificial sequence
<220> FEATURE:
<223> OTHER INFORMATION: Primer oligonucleotide

<400> SEQUENCE: 15

```
actacagtga cgtggacatc                                                20
```

```
<210> SEQ ID NO 16
<211> LENGTH: 20
<212> TYPE: DNA
<213> ORGANISM: Artificial sequence
<220> FEATURE:
<223> OTHER INFORMATION: Primer oligonucleotide

<400> SEQUENCE: 16
tgttatcaca ctggtgctaa                                              20

<210> SEQ ID NO 17
<211> LENGTH: 21
<212> TYPE: DNA
<213> ORGANISM: Artificial sequence
<220> FEATURE:
<223> OTHER INFORMATION: Reporter oligonucleotide
<220> FEATURE:
<221> NAME/KEY: modified_base
<222> LOCATION: (1)..(1)
<223> OTHER INFORMATION: Base 1 modified with Bodipy Texas Red

<400> SEQUENCE: 17
acttctaatc tgtaagagca g                                            21
```

US 6,780,584 B1

ELECTRONIC SYSTEMS AND COMPONENT DEVICES FOR MACROSCOPIC AND MICROSCOPIC MOLECULAR BIOLOGICAL REACTIONS, ANALYSES AND DIAGNOSTICS

RELATED APPLICATION INFORMATION

The following applications and patents are incorporated by reference herein in their entirety: application Ser. No. 08/986,065, filed Dec. 5, 1997, entitled "METHODS AND PROCEDURES FOR MOLECULAR BIOLOGICAL ANALYSIS AND DIAGNOSTICS", now issued as U.S. Pat. No. 6,051,380, which is a continuation-in-part of application Ser. No. 08/855,058 entitled "METHODS FOR ELECTRONIC FLUORESCENT PERTURBATION FOR ANALYSIS AND ELECTRONIC PERTURBATION CATALYSIS FOR SYNTHESIS", filed May 14, 1997, now issued as U.S. Pat. No. 6,048,690, which is a continuation-in-part of application Ser. No. 08/534,454, filed Sep. 27, 1995, entitled "APPARATUS AND METHODS FOR ACTIVE PROGRAMMABLE MATRIX DEVICES", which is a continuation-in-part of application Ser. No. 08/304,657, filed Sep. 9, 1994, entitled "AUTOMATED MOLECULAR BIOLOGICAL DIAGNOSTIC SYSTEM," now issued as U.S. Pat. No. 5,632,957, (which has been continued into application Ser. No. 08/859,644, filed May 20, 1997, entitled "CONTROL SYSTEM FOR ACTIVE, PROGRAMMABLE ELECTRONIC MICROBIOLOGY SYSTEM"), which is a continuation-in-part of application Ser. No. 08/271,882, filed Jul. 7, 1994, entitled "METHODS FOR ELECTRONIC STRINGENCY CONTROL FOR MOLECULAR BIOLOGICAL ANALYSIS AND DIAGNOSTICS," now allowed, which is a continuation-in-part of Ser. No. 08/146,504, filed Nov. 1, 1993, entitled "ACTIVE PROGRAMMABLE ELECTRONIC DEVICES FOR MOLECULAR BIOLOGICAL ANALYSIS AND DIAGNOSTICS", now issued as U.S. Pat. No. 5,605,662, (which has been continued into application Ser. No. 08/725,976, filed Oct. 4, 1996, entitled "METHODS FOR ELECTRONIC SYNTHESIS OF POLYMERS"), and also a continuation-in-part of application Ser. No. 08/708,262, filed Sep. 6, 1996, entitled "METHODS AND MATERIALS FOR OPTIMIZATION OF ELECTRONIC HYBRIDIZATION REACTIONS"; and application Ser. No. 08/986,065, filed Dec. 5, 1997, now issued as U.S. Pat. No. 6,051,380, entitled "METHODS AND PROCEDURES FOR MOLECULAR BIOLOGICAL ANALYSIS AND DIAGNOSTICS."

BRIEF DESCRIPTION

This invention pertains to the design, fabrication, and uses of an electronic system which can actively carry out and control multi-step and multiplex reactions in macroscopic or microscopic formats. In particular, these reactions include molecular biological reactions, such as nucleic acid hybridizations, nucleic acid amplification, sample preparation, antibody/antigen reactions, clinical diagnostics, combinatorial chemistry and selection, drug screening, oligonucleotide and nucleic acid synthesis, peptide synthesis, biopolymer synthesis, and catalytic reactions. A key feature of the present invention is the ability to control the localized concentration of two or more reaction-dependant molecules and their reaction environment in order to greatly enhance the rate and specificity of the molecular biological reaction.

BACKGROUND OF THE INVENTION

Molecular biology comprises a wide variety of techniques for the analysis of nucleic acids and proteins, many of which form the basis of clinical diagnostic assays. These techniques include nucleic acid hybridization analysis, restriction enzyme analysis, genetic sequence analysis, and separation and purification of nucleic acids and proteins (See, e.g., J. Sambrook, E. F. Fritsch, and T. Maniatis, *Molecular Cloning: A Laboratory Manual*, 2 Ed., Cold Spring Harbor Laboratory Press, Cold Spring Harbor, N.Y., 1989).

Many molecular biology techniques involve carrying out numerous operations on a large number of samples. They are often complex and time consuming, and generally require a high degree of accuracy. Many a technique is limited in its application by a lack of sensitivity, specificity, or reproducibility. For example, problems with sensitivity and specificity have so far limited the practical applications of nucleic acid hybridization.

Nucleic acid hybridization analysis generally involves the detection of a very small numbers of specific target nucleic acids (DNA or RNA) with probes among a large amount of non-target nucleic acids. In order to keep high specificity, hybridization is normally carried out under the most stringent conditions, achieved through various combinations of temperature, salts, detergents, solvents, chaotropic agents, and denaturants.

Multiple sample nucleic acid hybridization analysis has been conducted on a variety of filter and solid support formats (see G. A. Beltz et al., in *Methods in Enzymology*, Vol. 100, Part B, R. Wu, L. Grossmam, K. Moldave, Eds., Academic Press, New York, Chapter 19, pp. 266–308, 1985). One format, the so-called "dot blot" hybridization, involves the non-covalent attachment of target DNAs to a filter, which are subsequently hybridized with a radioisotope labeled probe(s). "Dot blot" hybridization gained widespread use, and many versions were developed (see M. L. M. Anderson and B. D. Young, in *Nucleic Acid Hybridization—A Practical Approach*, B. D. Hames and S. J. Higgins, Eds., IRL Press, Washington D.C., Chapter 4, pp. 73–111, 1985). The "dot blot" hybridization has been further developed for multiple analysis of genomic mutations (D. Nanibhushan and D. Rabin, in EPA 0228075, Jul. 8, 1987) and for the detection of overlapping clones and the construction of genomic maps (G. A. Evans, in U.S. Pat. No. 5,219,726, Jun. 15, 1993).

Another format, the so-called "sandwich" hybridization, involves attaching oligonucleotide probes covalently to a solid support and using them to capture and detect multiple nucleic acid targets. (M. Ranki et al., Gene, 21, pp. 77–85, 1983; A. M. Palva, T. M. Ranki, and H. E. Soderlund, in UK Patent Application GB 2156074A, Oct. 2, 1985; T. M. Ranki and H. E. Soderlund in U.S. Pat. No. 4,563,419, Jan. 7, 1986; A. D. B. Malcolm and J. A. Langdale, in PCT WO 86/03782, Jul. 3, 1986; Y. Stabinsky, in U.S. Pat. No. 4,751,177, Jan. 14, 1988; T. H. Adams et al., in PCT WO 90/01564, Feb. 22, 1990; R. B. Wallace et al. 6 Nucleic Acid Res. 11, p. 3543, 1979; and B. J. Connor et al., 80 Proc. Natl. Acad. Sci. USA pp. 278–282, 1983). Multiplex versions of these formats are called "reverse dot blots".

Using the current nucleic acid hybridization formats and stringency control methods, it remains difficult to detect low copy number (i.e., 1–100,000) nucleic acid targets even with the most sensitive reporter groups (enzyme, fluorophores, radioisotopes, etc.) and associated detection systems (fluorometers, luminometers, photon counters, scintillation counters, etc.).

This difficulty is caused by several underlying problems associated with direct probe hybridization. One problem relates to the stringency control of hybridization reactions.

Hybridization reactions are usually carried out under the stringent conditions in order to achieve hybridization specificity. Methods of stringency control involve primarily the optimization of temperature, ionic strength, and denaturants in hybridization and subsequent washing procedures. Unfortunately, the application of these stringency conditions causes a significant decrease in the number of hybridized probe/target complexes for detection.

Another problem relates to the high complexity of DNA in most samples, particularly in human genomic DNA samples. When a sample is composed of an enormous number of sequences which are closely related to the specific target sequence, even the most unique probe sequence has a large number of partial hybridizations with non-target sequences.

A third problem relates to the unfavorable hybridization dynamics between a probe and its specific target. Even under the best conditions, most hybridization reactions are conducted with relatively low concentrations of probes and target molecules. In addition, a probe often has to compete with the complementary strand for the target nucleic acid.

A fourth problem for most present hybridization formats is the high level of non-specific background signal. This is caused by the affinity of DNA probes to almost any material.

These problems, either individually or in combination, lead to a loss of sensitivity and/or specificity for nucleic acid hybridization in the above described formats. This is unfortunate because the detection of low copy number nucleic acid targets is necessary for most nucleic acid-based clinical diagnostic assays.

Because of the difficulty in detecting low copy number nucleic acid targets, the research community relies heavily on the polymerase chain reaction (PCR) for the amplification of target nucleic acid sequences (see M. A. Innis et al., *PCR Protocols: A Guide to Methods and Applications*, Academic Press, 1990). The enormous number of target nucleic acid sequences produced by the PCR reaction improves the subsequent direct nucleic acid probe techniques, albeit at the cost of a lengthy and cumbersome procedure.

A distinctive exception to the general difficulty in detecting low copy number target nucleic acid with a direct probe is the in-situ hybridization technique. This technique allows low copy number unique nucleic acid sequences to be detected in individual cells. In the in-situ format, target nucleic acid is naturally confined to the area of a cell ($\sim$20–502 $\mu m^2$) or a nucleus ($\sim$10 $\mu m^2$) at a relatively high local concentration. Furthermore, the probe/target hybridization signal is confined to a microscopic and morphologically distinct area; this makes it easier to distinguish a positive signal from artificial or non-specific signals than hybridization on a solid support.

Mimicking the in-situ hybridization in some aspects, new techniques are being developed for carrying out multiple sample nucleic acid hybridization analysis on micro-formatted multiplex or matrix devices (e.g., DNA chips) (see M. Barinaga, 253 Science, pp. 1489, 1991; W. Bains, 10 Bio/Technology, pp. 757–758, 1992). These methods usually attach specific DNA sequences to very small specific areas of a solid support, such as micro-wells of a DNA chip. These hybridization formats are micro-scale versions of the conventional "reverse dot blot" and "sandwich" hybridization systems.

The micro-formatted hybridization can be used to carry out "sequencing by hybridization" (SBH) (see M. Barinaga, 253 Science, pp. 1489, 1991; W. Bains, 10 Bio/Technology, pp. 757–758, 1992). SBH makes use of all possible n-nucleotide oligomers (n-mers) to identify n-mers in an unknown DNA sample, which are subsequently aligned by algorithm analysis to produce the DNA sequence (R. Drmanac and R. Crkvenjakov, Yugoslav Patent Application #570/87, 1987; R. Drmanac et al., 4 Genomics, 1–14, 1989; Strezoska et al., 88 Proc. Natl. Acad. Sci. USA 10089, 1991; and R. Drmanac and R. B. Crkvenjakov, U.S. Pat. No. 5,202,231, Apr. 13, 1993), U.S. Pat. No. 6,018,041, Jan. 25, 2000, and U.S. Pat. No. 6,025,136, Feb. 15, 2000).

There are two formats for carrying out SBH. One format involves creating an array of all possible n-mers on a support, which is then hybridized with the target sequence. This is a version of the reverse dot blot. Another format involves attaching the target sequence to a support, which is sequentially probed with all possible n-mers. Both formats have the fundamental problems of direct probe hybridizations and additional difficulties related to multiplex hybridizations. This inability to achieve "sequencing by hybridization" by a direct hybridization method lead to a so-called "format 3", which incorporates a ligase reaction step. While, providing some degree of improvement, it actually represents a different mechanism involving an enzyme reaction step to identify base differences.

Southern, United Kingdom Patent Application GB 8810400, 1988; E. M. Southern et al., 13 Genomics 1008, 1992, proposed using the "reverse dot blot" format to analyze or sequence DNA. Southern identified a known single point mutation using PCR amplified genomic DNA. Southern also described a method for synthesizing an array of oligonucleotides on a solid support for SBH. However, Southern did not address how to achieve optimal stringency condition for each oligonucleotide on an array. See also U.S. Pat. No. 6,054,270, Apr. 25, 2000.

Fodor et al., 364 Nature, pp. 555–556, 1993, used an array of 1,024 8-mer oligonucleotides on a solid support to sequence DNA. In this case, the target DNA was a fluorescently labeled single-stranded 12-mer oligonucleotide containing only nucleotides the A and C bases. A concentration of 1 $\mu$mol ($\sim 6 \times 10^{11}$ molecules) of the 12-mer target sequence was necessary for the hybridization with the 8-mer oligomers on the array. The results showed many mismatches. Like Southern, Fodor et al., did not address the underlying problems of direct probe hybridization, such as stringency control for multiplex hybridizations. These problems, together with the requirement of a large quantity of the simple 12-mer target, indicate severe limitations to this SBH format.

Concurrently, Drmanac et al., 260 Science 1649–1652, 1993, used the above discussed second format to sequence several short (116 bp) DNA sequences. Target DNAs were attached to membrane supports ("dot blot" format). Each filter was sequentially hybridized with 272 labeled 10-mer and 11-mer oligonucleotides. A wide range of stringency conditions were used to achieve specific hybridization for each n-mer probe; washing times varied from 5 minutes to overnight, and temperatures from 0° C. to 16° C. Most probes required 3 hours of washing at 16° C. The filters had to be exposed for 2 to 18 hours in order to detect hybridization signals. The overall false positive hybridization rate was 5% in spite of the simple target sequences, the reduced set of oligomer probes, and the use of the most stringent conditions available.

Fodor et al., 251 Science 767–773, 1991, used photolithographic techniques to synthesize oligonucleotides on a matrix. Pirrung et al., in U.S. Pat. No. 5,143,854, Sep. 1, 1992, teach large scale photolithographic solid phase synthesis of polypeptides in an array fashion on silicon substrates.

In another approach of matrix hybridization, Beattie et al., in *The 1992 San Diego Conference: Genetic Recognition*, November, 1992, used a microrobotic system to deposit micro-droplets containing specific DNA sequences into individual microfabricated sample wells on a glass substrate. The hybridization in each sample well is detected by interrogating miniature electrode test fixtures, which surround each individual microwell with an alternating current (AC) electric field.

Regardless of the format, all current micro-scale DNA hybridizations and SBH approaches do not overcome the underlying problems associated with nucleic acid hybridization reactions. They require very high levels of relatively short single-stranded target sequences or PCR amplified DNA, and produce a high level of false positive hybridization signals even under the most stringent conditions. In the case of multiplex formats using arrays of short oligonucleotide sequences, it is not possible to optimize the stringency condition for each individual sequence with any conventional approach because the arrays or devices used for these formats can not change or adjust the temperature, ionic strength, or denaturants at an individual location, relative to other locations. Therefore, a common stringency condition must be used for all the sequences on the device. This results in a large number of non-specific and partial hybridizations and severely limits the application of the device. The problem becomes more compounded as the number of different sequences on the array increases, and as the length of the sequences decreases below 10-mers or increase above 20-mers. This is particularly troublesome for SBH, which requires a large number of short oligonucleotide probes.

Nucleic acids of different size, charge, or conformation are routinely separated by electrophoresis techniques which can distinguish hybridization species by their differential mobility in an electric field. Pulse field electrophoresis uses an arrangement of multiple electrodes around a medium (e.g., a gel) to separate very large DNA fragments which cannot be resolved by conventional gel electrophoresis systems (see R. Anand and E. M. Southern in *Gel Electrophoresis of Nucleic Acids—A Practical Approach*, 2 ed., D. Rickwood and B. D. Hames Eds., IRL Press, New York, pp. 101–122, 1990).

Pace, U.S. Pat. No. 4,908,112, Mar. 13, 1990, describes using micro-fabrication techniques to produce a capillary gel electrophoresis system on a silicon substrate. Multiple electrodes are incorporated into the system to move molecules through the separation medium within the device.

Soane and Soane, U.S. Pat. No. 5,126,022, Jun. 30, 1992, describe that a number of electrodes can be used to control the linear movement of charged molecules in a mixture through a gel separation medium contained in a tube. Electrodes have to be installed within the tube to control the movement and position of molecules in the separation medium.

Washizu, M. and Kurosawa, O., 26 IEEE Transactions on Industry Applications 6, pp. 1165–1172, 1990, used high-frequency alternating current (AC) fields to orient DNA molecules in electric field lines produced between microfabricated electrodes. However, the use of direct current (DC) fields is prohibitive for their work. Washizu 25 Journal of Electrostatics 109–123, 1990, describes the manipulation of cells and biological molecules using dielectrophoresis. Cells can be fused and biological molecules can be oriented along the electric fields lines produced by AC voltages between the micro-electrode structures. However, the dielectrophoresis process requires a very high frequency AC (1 MHz) voltage and a low conductivity medium. While these techniques can orient DNA molecules of different sizes along the AC field lines, they cannot distinguish between hybridization complexes of the same size.

MacConnell, U.S. Pat. No. 4,787,936, Nov. 29, 1988, describes methods and means for annealing complementary nucleic acid molecules at an accelerated rate. The nucleic acid probes are electrophoretically concentrated with a surface to which various sequences are bound. Unannealed probe molecules are electronically removed from the surface region by reversal of the electrical orientation, so as to electrophoretically move away from the surface of those materials which had been previously concentrated at the surface. In yet another aspect, the patent describes moving concentrated, unannealed probe molecules successively in various directions along the surface to which the sequences are bound.

Stanley, C. J., U.S. Pat. No. 5,527,670, issued Jun. 18, 1996, claiming priority to GB 9019946, filed Sep. 12, 1990 and GB 9112911 filed Jun. 14, 1991. Stanley discloses a process for denaturing native double-stranded nucleic acid material into its individual strands in an electrochemical cell. An electrical treatment of the nucleic acid with a voltage applied to the nucleic acid material by an electrode is utilized. Promoter compounds, such as methylviologen, are suggested to speed denaturation. The process is suggested for use in the detection of nucleic acid by hybridizing with a labeled probe or in the amplification of DNA by a polymerase chain reaction or ligase chain reaction.

More recently, attempts have been made at microchip based nucleic acid arrays to permit the rapid analysis of genetic information by hybridization. Many of these devices take advantage of the sophisticated silicon manufacturing processes developed by the semiconductor industry over the last forty years. In these devices, many parallel hybridizations may occur simultaneously on immobilized capture probes. Stringency and rate of hybridization is generally controlled by temperature and salt concentration of the solutions and washes. Even though of very high probe densities, such a "passive" micro-hybridization approaches have several limitations, particularly for arrays directed at reverse dot blot formats, for base mismatch analysis, and for re-sequencing and sequencing by hybridization applications.

First, as all nucleic acid probes are exposed to the same conditions simultaneously, capture probes must have similar melting temperatures to achieve similar levels of hybrid stringency. This places limitations on the length, GC content and secondary structure of the capture probes. Also, single-stranded target fragments must be selected out for the actual hybridization, and extremely long hybridization and stringency times are required(see, e.g., Guo, Z, et.al., Nucleic Acid Research, V.22, #24, pp 5456–5465, 1994).

Second, for single base mismatch analysis and re-sequencing applications a relatively large number of capture probes (>16) must be present on the array to interrogate each position in a given target sequence. For example, a 400 base pair target sequence would require an array with over 12,000 different probe sequences (see, e.g., Kozal, M. J., et.al., Nature Medicine, V.2, #7, pp.753–759, 1996).

Third, for many applications large target fragments, including PCR or other amplicons, can not be directly hybridized to the array. Frequently, complicated secondary processing of the amplicons is required, including: (1) further amplification; (2)conversion to single-stranded RNA fragments; (3) size reduction to short oligomers, and (4) intricate molecular biological/enzymatic reactions steps, such as ligation reactions.

Fourth, for passive hybridization the rate is proportional to the initial concentration of the target fragments in the solution, therefore, very high concentrations of target is required to achieve rapid hybridization.

Fifth, because of difficulties controlling hybridization conditions, single base discrimination is generally restricted to capture oligomers sequences of 20 bases or less with centrally placed differences (see, e.g., Chee '96; Guo, Z, et.al., Nucleic Acid Research, V.22, #24, pp 5456–5465, 1994; Kozal, M. J., et.al., Nature Medicine, V.2, #7, pp.753–759, 1996).

As is apparent from the preceding discussion, numerous attempts have been made to provide effective techniques to conduct multi-step, multiplex hybridizations and other molecular biological reactions. However, for at least the reasons stated above, these techniques have been proved deficient. Despite the long-recognized need for effective technique, no satisfactory solution has been proposed previously.

SUMMARY OF INVENTION

In an attempt to circumvent these limitations, the present invention utilizes electric fields as an independent parameter to modulate or control multi-step and multiplex reactions in macroscopic or microscopic formats. In particular, these reactions include molecular biological reactions, such as nucleic acid hybridizations, nucleic acid amplification, sample preparation, antibody/antigen reactions, clinical diagnostics, combinatorial chemistry and selection, drug screening, oligonucleotide and nucleic acid synthesis, peptide synthesis, biopolymer synthesis, and catalytic reactions. The devices of the invention have proven particularly useful for the acceleration of transport and hybridization of nucleic acids and the control of stringency of nucleic acid interactions. These are "active" devices in that they exploit electronic instead of passive diffusion technology. The "active" device provides a controllable electric (electrophoretic) field as a driving force to move and concentrate nucleic acid molecules (probes and/or targets) or other reagents to a selected microscopic/macroscopic test site (with other fixed target or probe molecules). In addition to salt, pH, temperature and chaotropic agents, the electric field strength (voltage/current/current density) provides a precisely controllable and continuously variable parameter for adjustment of nucleic acid interactions. Finally, by the utilization of particular buffer compositions on either side of the test site/semi-permeable matrix structure, the devices and methods of the present invention create favorable reaction zones for the reactant molecules (e.g. DNA probes and targets), and the ability to strictly control or modulate the reaction at the test site. Thus, a key aspect of the electronic devices and methods of this invention is that reactants or analytes from a substantially non-reactive environment can be rapidly brought to a selected test site (microlocation/macrolocation) where other selective binding agents or reactants are present and a third group of entities from another physically separate environment can be rapidly brought to the test site to create a favorable reaction zone.

The present invention relates to the design, fabrication, and uses of electronic systems and devices which can actively carry out controlled multi-step and multiplex reactions in microscale and macroscale formats. These reactions include, but are not limited to, most molecular biological procedures, such as nucleic acid hybridizations, antibody/antigen reaction, cell separation, and related clinical diagnostics.

In addition, the devices are able to carry out multi-step combinational biopolymer and combinatorial synthesis, including, but not limited to, the synthesis of different oligonucleotides or peptides at specific microlocations.

In addition, the electronic devices and methods of this invention allow rapid multiplex hybridization and discrimination of single base mismatches in full length DNA fragments and PCR amplicons, under what would be considered substantially non-hybridizing, denaturing or non-stringent conditions by any passive or conventional hybridization technique so that hybridization reactions occur only at the test sites.

In the reaction-modifying methods of the invention, each test site (microlocation, macrolocation) comprises a semi-permeable matrix (SPM) between two buffer reservoirs or chambers. This semi-permeable matrix may comprise several "sub-layers" with different functions (e.g., a charged surface membrane layer and a hydrogel layer). However, the overall characteristic of the SPM is that it forms a barrier which impedes the free diffusion of molecules between the two buffer reservoirs (chambers). Each of the buffer reservoirs (chambers) has an associated electrode(s). Attached to the surface of or within the SPM is a specific binding entity. In preferred embodiments of the invention, a first buffer reservoir contains a low conductance buffer and a first charged entity which reacts with the specific binding entity. A second buffer reservoir contains a second, oppositely charged entity which affects the reaction between the first charged entity and the specific binding entity. When an electric potential is applied across the SPM, the first charged entity rapidly migrates through bulk solution to the test site/semi-permeable matrix, creating a localized area of high concentration where it interacts with the specific binding entity. At the same time, the second charged entity migrates "through" the SPM, creating a localized zone of relatively high concentration of the second entity within and adjacent to the SPM wherein it may interact with the first charged entity and the specific binding entity at an effective concentration. Thus, a "reaction zone" of high localized concentration of the first and second entity (by electromotive force) and the specific binding entity (by binding to the SPM) is created at the semi-permeable interface between the two buffer reservoirs. This greatly facilitates the interaction between the first charged entity and the specific binding entity by first creating a zone of high concentration which increases the number of collisions between the specific binding entity and the two charged entities, and second by producing favorable conditions for the reaction (pH, specific buffer species, specific cations, specific anions, ionic strength, surfactants, etc.).

If the binding reaction is being utilized as a detection method, as in the case of a DNA hybridization reaction, or antigen/antibody interactions, then the method may also comprise a step utilizing the electric field to remove the members of the first charged entity which are reacting with the specific binding entity in a non-specific manner. By reversing the potential/bias, the first charged entity interacting with the specific binding entity experiences an electromotive force away from the specific binding entity. In addition, the concentration of the second charged entity, which had facilitated interactions between the first charged entity and the specific binding entity, decreases as it ceases to migrate through the SPM. Thus, members of the first charged entity which are not bound specifically to the specific binding entity, including single base mismatches which are slightly less thermodynamically stable, will dissociate from the specific binding entity, leaving the specifically bound members of the first charged entity for detection.

The macroscale and microscale devices for use in the methods of the present invention are preferably fabricated using techniques which include micromachining, high-tolerance molding, microlithography or any other techniques used for fabricating small laboratory instruments or systems, lab on a chip devices, or biochip devices. The device of the invention has a test site location comprising a semi-permeable matrix between first and second buffer reservoirs or chambers (FIG. 1). Although a single test location device is considered within the embodiments of the present invention, devices with a multiple of test sites or locations (microlocations or macrolocations) are the more preferred embodiments of this invention (FIG. 2). While the devices of this invention may contain a specific binding entity on or within the SPM, other devices may simply have binding or reactive sites on or within the SPM for later attachment of the specific binding entities, e.g., streptavidin. For instance, in a preferred embodiment, the device for use in the present invention comprises a SPM which contains streptavidin, so that specific binding entities which have been modified with a biotin moiety (e.g. DNA probes or target sequences) may be subsequently addressed and attached to the SPM.

Although a common first and second buffer reservoir (chamber) may be used for all microlocations, individual reservoirs for each location may also be used for the first, second, or both buffer reservoirs (FIGS. 3, 4, and 5). The use of individual first reservoirs (chambers) may, for example, be desirable to prevent cross-contamination of patient samples in high-throughput clinical testing applications of the invention. Alternatively, indentations in a first buffer reservoir (or the support structure for the SPM) may be provided to aid sample loading, as depicted in FIGS. 8 and 9. These applications could still utilize a common second reservoir, as depicted in FIG. 3. Although each individual test site microlocation may be able to electronically control and direct the transport and attachment of specific binding entities (e.g., nucleic acids, antibodies), a device in which common electrodes are used for all test sites microlocations is one of the more preferred embodiments of the present invention (FIG. 2). The use of a first and second common electrode in a first and second common buffer reservoir allow several substantially similar reactions to be carried out in parallel on several individual test sites microlocations under identical electronic conditions. This embodiment is preferable in instances where high-throughput processing of multiple samples is required, such as in pharmaco-genomic, drug discovery and some high volume clinical testing applications. Conversely, individual first and seconds electrodes may be used, as depicted in FIG. 3 or FIG. 4. These embodiments may be preferred in order to individually control the electric field at each test site microlocation, e.g., for electronic stringency in particular. All test sites microlocations can be addressed with different or similar specific binding entities. Because of the use of "active" electronic control over the molecular biochemical reaction and its environment, different specific binding entities and first and second charged entity may be used under conditions (i.e. ambient temperature, pH, ionic strength) where they (the reactants) would not normally be compatible or controllable in a conventional or passive type reactions.

Thus, one aspect of the present invention is a device for carrying out molecular biological reactions with an array of test sites or microlocations (or macrolocations) across which an electric field (current) may be applied, wherein:

a) each microscopic location comprises a SPM separating a first and second buffer reservoir (chamber) containing a first and second charged entity;

b) the SPM is so composed such that there is little or no migration of the first charged entity in the absence of an electric field, but so that controlled migration of the first charged entity occurs when an electric field is applied for the time necessary to achieve the biochemical reaction;

c) the SPM is so composed that there is little or no migration of the second charged entity in the absence of an electric field, but so that controlled migration of the second charged entity occurs when an electric field is applied for the time necessary to achieve the biochemical reaction;

d) wherein at each test site or microlocation there is attached to the first buffer chamber side of the SPM a specific binding entity which reacts with the first charged entity; and e) wherein the second charged entity modulates the reaction of the first charged entity with the specific binding entity.

By "array" is meant an arrangement of test site microlocations (and/or macrolocations) on the device. The locations can be arranged in two dimensional arrays, three dimensional arrays, or other formats. The number of locations can range from several to hundreds of thousands. In some cases (e.g., high throughput systems) microlocations can be DNA or other samples spotted (addressed) onto filter paper or membranes which are processed through an electronic hybridization system.

In a second aspect, this invention features a method for attaching the specific binding entity to the first-buffer side of the microlocations on the device. When activated, the device can affect the free field electrophoretic transport of any charged functionalized specific binding entity directly to the microlocation. Upon contacting the specific test site microlocation, the functionalized specific binding entity immediately becomes attached (covalently or non-covalently) to the surface or within the SPM. The process can be rapidly carried out in parallel at each test site microlocation, whether common or individual first buffer reservoirs are used.

By "charged functionalized specific binding entity" is meant a specific binding entity that is reactive (i.e., capable of covalent or non-covalent attachment to a location) and carries a net charge (either positive or negative). This also includes mixtures of more than one specific binding entity.

In a third aspect, this invention features a method for concentrating and reacting analytes, probes or reactants within a reaction zone at the test site microlocations (macrolocations) on the device (FIG. 1b). After the attachment of the specific binding entities, the analyte(s), probe(s) or reactant(s) (the first charged entity) is loaded into the first buffer reservoir. A second buffer, containing the second charged entity, is loaded into the second buffer reservoir. An electric potential is applied across the SPM between the two reservoirs, producing subsequent electrophoretic ionic flow across the SPM. This unique feature allows relatively dilute charged analytes or reactant molecules free in solution (first reservoir) to be rapidly transported, concentrated, and reacted at the microlocations while the second charged entity (second reservoir) migrates across the SPM to modulate the reaction between the analyte, probe, or reagent and the specific binding entity. This ability to concentrate dilute analyte or reactant molecules at selected microlocations wherein a reaction zone of increased concentration of the second charged entity is created that greatly accelerates the reaction at these test site microlocations. Thus, in the third aspect of the invention electronic devices and methods relate to improving reaction rates and efficiency. In the case of nucleic acid hybridization reactions, "electronic hybridization" can be carried out according to the above method, the methods further comprising steps chosen from:

using "electronic hybridization" to improve the overall hybridization of amplified target DNA and RNA sequences on arrays of capture probe oligonucleotides.

using "electronic hybridization" to improve the hybridization of any target DNA or RNA sequences on arrays of capture probe oligonucleotides in reverse dot blot formats.

using "electronic hybridization" for sequencing by hybridization (SBH) utilizing arrays with capture probes 8 bases or less in length.

using "electronic hybridization" to improve the hybridization of any target DNA or RNA sequences on arrays of capture probes in sandwich formats, with subsequent hybridization of reporter probes (fluorescent, chemiluminescent, radioactive, etc.).

using "electronic hybridization" to improve the hybridization of any DNA or RNA sequence on arrays of nucleic acid sequences in dot blot formats (target sequences addressed to the array, with subsequent hybridization of reporter probes)

using "electronic hybridization" to improve the hybridization of target nucleic acid sequences on arrays of nucleic acid probes in homogeneous/heterogeneous hybridization formats.

using "electronic hybridization" to improve the hybridization of target RNA or cDNA sequences on arrays of nucleic acid probes for gene expression applications.

using "electronic hybridization" for individual hybridization events occurring in the same bulk solution and at the same temperature.

using "electronic hybridization" to improve hybridization and detection of un-amplified or low copy number target DNA sequences by complexity reduction.

Using "electronic hybridization" to improve signal amplification techniques (fluorescent, chemiluminescent, calorimetric, enzymatic, dendrimers, branched DNA, and metallic, fluorescent, or magnetic nanospheres, etc.) used to detect un-amplified target or poorly amplified target DNA sequences.

When the desired reaction is complete, the electric field potential/bias can be reversed to remove non-specific analytes or unreacted molecules from the microlocations. The subsequent analysis of the analytes at the specific microlocations is also greatly improved by the ability to repulse non-specific entities and partially hybridized sequences from these locations.

Thus, in a fourth aspect, this invention features a methods for improving efficiency and stringency of nucleic acid hybridization reactions as carried out according to the above method, the methods further comprising steps chosen from:

rapidly removing non-specifically bound target DNA (or DNA probe) sequences from specific test site microlocation(s) or macrolocation(s) where hybridization has occurred by reversing the electric potential;

rapidly removing competing complementary target DNA or DNA probe sequences from specific test site microlocation(s) or macrolocation(s) where hybridization has occurred by reversing the electric potential;

adjusting electronic stringency control (ESC) via voltage and current level and density to remove partially hybridized DNA sequences or DNA probe (more than one base mis-match);

adjusting ESC via voltage and current level and density to improve the resolution of single base mis-match hybridizations using probes in the 8-mer to 21-mer range (e.g., to identify point mutations);

using ESC via voltage and current level and density, to utilize oligonucleotide point mutation probes outside of the ranges used in conventional procedures (e.g., probes longer than 21-mers and shorter than 8-mers); for example, 4-mer to 7-mer, and 22-mer to 30-mer or longer.

using ESC via voltage and current level and density, for sequencing by hybridization (SBH) arrays utilizing capture probes from 4 to 8 nucleotides in length.

applying ESC via voltage and current level and density, to discriminate single nucleotide polymorphisms (SNPs).

using ESC to improve the overall hybridization of amplified target DNA and RNA sequences on arrays of capture probe oligonucleotides.

using ESC to improve the hybridization of any target DNA or RNA sequences on arrays of capture probe oligonucleotides in reverse dot blot formats.

using ESC to improve the hybridization of any target DNA or RNA sequences on arrays of capture probe oligonucleotides in sandwich formats.

using ESC to improve the hybridization of any DNA or RNA sequence on arrays of nucleic acid sequences in the more classical dot blot format (target sequences on the array, reporter probes added)

using ESC to improve the hybridization of target nucleic acid sequences on arrays of nucleic acid probes in homogeneous/heterogeneous hybridization formats.

using ESC to improve the hybridization of target RNA or cDNA sequences on arrays of nucleic acid probes for gene expression applications.

applying independent ESC to individual hybridization events occurring in the same bulk solution and at the same temperature; and using ESC to improve hybridization and detection of un-amplified target DNA or poorly amplified sequences on arrays.

using ESC to improve signal amplification techniques (fluorescent, chemiluminescent, colorimetric, enzymatic, dendrimers, branched DNA, etc.) used to detect un-amplified target or poorly amplified target DNA sequences to arrays.

In a fifth aspect, this invention features a method for the combinatorial synthesis of biopolymers at the test site microlocations or macrolocations In an sixth aspect, this invention features a device which electronically delivers reagents and reactants with minimal use of fluidics.

In a seventh aspect, this invention features a device which carries out molecular biology and DNA amplification reactions (e.g. Polymerase Chain Reaction, Strand Displacement Amplification, restriction cleavage reactions, DNA/RNA polymerase and DNA ligase target amplification reactions.

In an eighth aspect, this invention features a device which can electronically size and identify restriction fragments (e.g. carry out electronic restriction fragment length polymorphism, short tandem repeat polymorphism and DNA finger printing analysis).

In an ninth aspect, this invention features a device which carries out antibody/antigen, immunodiagnostic reactions, and proteomic analysis.

In a tenth aspect, this invention features a device which is able to carry out combinatorial synthesis of oligonucleotides and peptides.

In an eleventh aspect, this invention features a device which selectively binds cells, processes cells for hybridization, causes cell lysis (electronic, hypotonic or hypertonic), removes DNA from cells, or carries out electronic in-situ hybridizations within the cells.

In a twelfth aspect, this invention features devices and methods which allow rapid multiplex hybridization and discrimination of single base mismatches (single nucleotide polymorphisms) in full length double-stranded or single-stranded DNA fragments, RNA fragments, PCR amplicons, and SDA amplicons, under what would normally be considered substantially non-hybridizing or denaturing conditions by any passive or conventional hybridization technique.

In a thirteenth aspect, this invention features electronic hybridization methods which incorporate buffer and/or electrolyte entity including but not limited to: histidine, di-histidine, histidine peptides, mixed histidine peptides, $Na^+$, $K^+$, $Mg^{++}$, $NH_4^+$, amines and other double strand DNA stabilizing entities; which can allow rapid transport and hybridization of nucleic acid fragments (DNA, RNA, etc.) under what would normally be considered substantially non-hybridizing or denaturing conditions by any passive or conventional hybridization technique.

In a fourteenth aspect, this invention features devices and methods which allow rapid multiplex hybridization and discrimination of multiple repeat sequences (di-, tri, tetra, etc.), including short tandem repeats (STRs) in nucleic acid fragments, under what would normally be considered substantially non-hybridizing or denaturing conditions by any passive or conventional hybridization technique.

In a fifteenth aspect, this invention features devices and methods which allow rapid multiplex hybridization in in-situ formats.

In a sixteenth aspect, this invention features devices and methods which can be combined into an instrument system which allows use of various specific binding entities or reactants which would not be compatible under normal passive or conventional reaction conditions, including common temperature and buffer composition.

In a seventeenth aspect, this invention features devices and methods which allow rapid multiplex catalytic reactions.

In a eighteenth aspect, this invention features devices and methods which allow rapid multiplex organic synthesis reactions.

In a nineteenth aspect, this invention features devices and methods which allow rapid multiplex polymer synthesis.

In a twentieth aspect, this invention features devices and methods which allow rapid combinatorial synthesis and selection reactions.

In a twenty-first aspect, this invention features devices and methods which allow rapid multiplex nanofabrication reactions.

In a twenty-second aspect, this invention features devices and methods which integrate biosensors or electronic detection components within the test site microlocations.

In a twenty-third aspect, this invention features devices with alternative second entity motive forces, such as the use of high pressure forces rather than or in addition to electromotive forces to transport the second entity through the semi-permeable matrix.

The active, electronic nature of the devices of the invention allows us to create new mechanisms for carrying out a wide variety of molecular biological reactions. These include novel methods for achieving both linear and exponential multiplication or amplification of target DNA and RNA molecules.

The device provides electronic mechanisms to: (1) transport denatured DNA or other charged entities in bulk solution at room temperature (e.g. well below their Tm points); (2) to selectively concentrate the specific charged entities, (e.g., DNA targets or probes, reactants, reagents, and enzymes, etc.) at the desired test site microlocation; and (3) to subsequently create "reaction zones" of favorable environment and reaction conditions to greatly decrease the time necessary for hybridization and/or other common molecular biological reactions. These all involve new physical parameters for carrying out molecular biological and target amplification type reactions.

A number of examples of electronically controlled molecular biology reactions (can be) have been developed, these include: (1) Electronically Directed Restriction Enzyme Cleavage of Specific ds-DNA Sequences; (2) Electronic Restriction Fragment Analysis; (3) Electronic Multiplication of Target DNA by DNA Polymerases; and (4) Electronic Ligation and Multiplication of Target DNA Sequences By DNA and RNA Polymerases; and (5) Electronic Multiplication of Target DNA by RNA Polymerases. These examples are representative of the types of molecular biological reactions and procedures which can be carried but on the devices of the invention.

Other features and advantages of the invention will be apparent from the following detailed description of the invention, and from the claims.

BRIEF DESCRIPTION OF THE DRAWINGS

FIG. 10. Functional Prototype Device. The schematic of a working prototype used for Examples 4, 5, and 6 is shown.

DETAILED DESCRIPTION OF THE INVENTION

Introduction

The devices and the related methodologies of this invention allow molecular biology and diagnostic reactions to be carried out under "complete electronic control". The meaning of "electronic control" as referred to in this invention goes beyond the conventional connotation of the term. Most conventional electronic devices, instruments, and detector systems are always at some level under electronic control. The electronic devices of this invention are not only under conventional electronic control, but more importantly they also provide further direct electronic control over the dynamic, physical, chemical and environmental aspects of carrying out molecular biological, diagnostic, synthetic, combinatorial, and catalytic reactions. The key aspect of the electronic devices and methods of this invention is that reactants or analytes which are in a substantially non-reactive environment, can be rapidly transported and concentrated at a selected test site (microlocation/macrolocation) where other selective binding agents or reactants are attached, and a third group of entities from another physically separate or distinct environment can be transported to the test site and used to now create a favorable reaction zone. In the case of a DNA hybridization reaction, denatured target DNA sequences in a non-hybridizing environment can be rapidly transported and concentrated at a selected test site (microlocation/macrolocation) where other selective DNA probes have been attached, and a third entity (e.g., a cationic buffer species or cationic salts) from another physically separate environment can be transported to the test site where it now creates a favorable hybridization reaction zone.

Figure 1A:
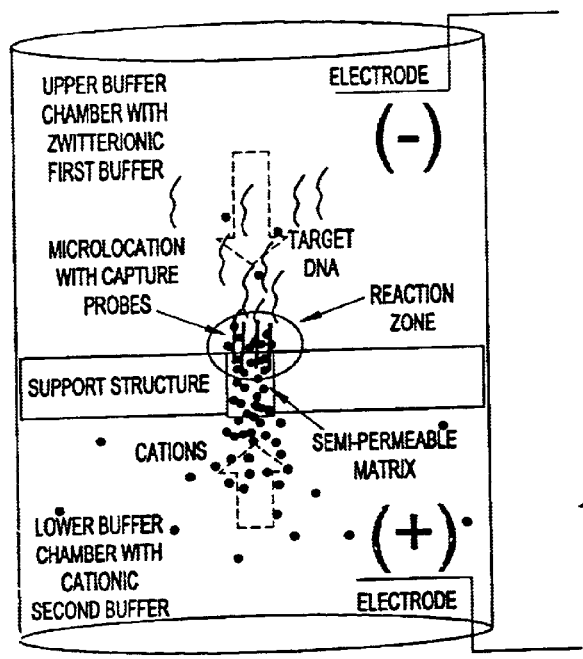
FIG. 1. Schematic of Basic Device While in Operation. (A) The basic components of the device under operation are shown. For purposed of illustration, hybridization of DNA is used as an example. Accordingly, the binding entity within the SPM is represented by "capture probes", the first charged entity in the upper chamber is "target DNA" and the second charged entity in the lower chamber is "cations". Arrows indicate electric field induced movement of first and second charged entities from the first and second buffer chamber into a semipermeable matrix (SPM). (B) An enlarged view of the reaction zone is shown.
Figure 1B:
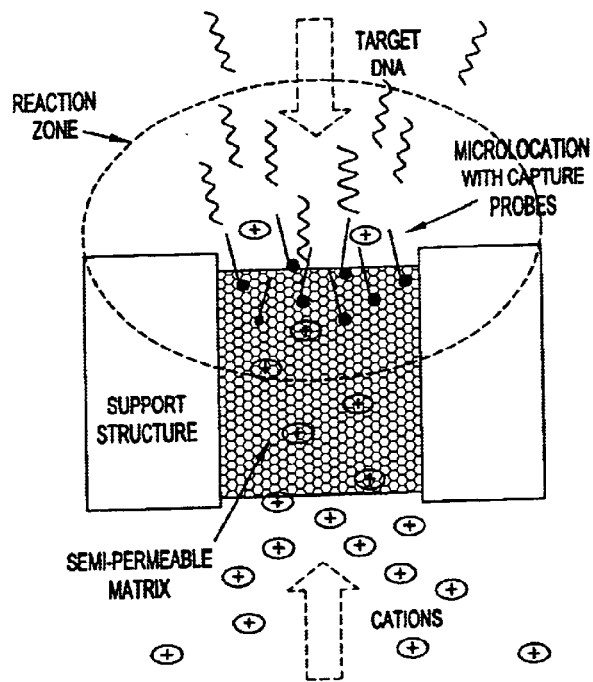

In the preferred embodiments, each test site microlocation or macrolocation comprises a semi-permeable matrix, (SPM), between two buffer reservoirs (chambers), as depicted in FIG. 1a and 1b. For the purposes of discussion, the first buffer reservoir (chamber) will be called the "upper" buffer reservoir (chamber), and the side of the semi-permeable matrix facing the upper buffer will be called the "upper" side of the SPM. Conversely, the second buffer reservoir (chamber) will be called the "lower" buffer reservoir (chamber). Although these terms are utilized for the discussion of the invention, they are not meant to so limit the invention to a particular geometry: upside-down and side-to-side (vertical) embodiments of the invention are also contemplated as within its scope.

Thus, one key aspect of the methods and devices of this invention is played by the semi-permeable matrix (SPM) which separates the first and second buffer reservoirs. In preferred embodiments, the SPM is at least derivatized on its upper surface for the covalent or non-covalent attachment of specific binding entities. The SPM may be so derivatized on its true surface as well as throughout it's three dimensional structure: an example is an agarose or polyacrylamide hydrogel SPM (impregnated with streptavidin) to which biotinylated probes have been attached. The SPM also regulates the diffusion of molecules from one buffer reservoir to the other. Thus, the SPM separates the different chemical environments (reactants, analytes, buffers, electrolytes, salts, metal ions, chaotropic agents, denaturants, etc.) of the first and second reservoirs. For example, in a DNA hybridization reaction (where DNA capture probes have first been selectively addressed and attached to the test site microlocations), the hybridizable target DNA sequences in the first reservoir are rapidly concentrated at the upper surface of the SPM (the test site microlocation or macrolocation) by electrophoretic transportation through the low conductance first buffer. Simultaneously, cations from the second buffer reservoir are drawn across the SPM by the electric field, creating a favorable hybridization reaction zone of relatively high cation concentration in and around the test site microlocation or macrolocation on the first-buffer-side of the SPM (see FIG. 1b). The design of the test site microlocation (macrolocation) structure allows high electric field densities to be achieved in these confined areas, creating highly localized concentration conditions or "reaction zones" that are favorable to hybridization or other reactions. The ability to create these favorable reaction zones, as well as to bring specific binding agents and analytes or reactants together at the test site microlocations represents one of the most important aspect of this invention. It is also within the scope of this invention to design and fabricate semi-permeable matrices (SPM's) which are composed of more than one layer, such as but not limited to; an upper and middle layer with selective diffusion properties and a third lower layer which provides support to the structure.

The devices of this invention are able to control and actively carry out a variety of assays and reactions. Analytes or reactants can be transported by free field electrophoresis from the bulk solution to the test site microlocation(s) where the analytes or reactants are effectively concentrated and reacted with the specific binding entity (entities) at the microlocation(s). The rapidity and sensitivity for detecting a specific analyte or reactant is improved because of the concentrating effect and because of the increased concentration of the second charged entity in the reaction zone. Any unbound analytes or reactants can be removed by reversing the polarity on a microlocation. This ability to produce a precisely controlled high field density (e.g. an electrophoretic field) at the microlocations, allows the selective "de-hybridization" of non-complementary DNA to be achieved to the level of single base mismatches or even completely complementary sequences. Thus, the devices provide further improvement of assay and reaction specificity.

The active nature of the devices provide independent electronic control over all aspects of the hybridization reaction (or other affinity, chemical, or catalytic reactions) occurring at the test site microlocations. These devices provide unique mechanisms for affecting hybridization reactions which are called electronic hybridization and electronic stringency control (ESC). For DNA hybridization reactions which require different stringency conditions, ESC can overcome inherent limitations of conventional array technologies. The active devices of this invention allow each microlocation to function as a concentration enhanced reaction zone for DNA hybridization in which both the concentration of DNA for complementation and the cations for stabilization are increased relative to the concentrations in the surrounding buffers. Additionally, it is unnecessary to change temperatures, and the need for multiple washing procedures is greatly reduced.

Figure 3:
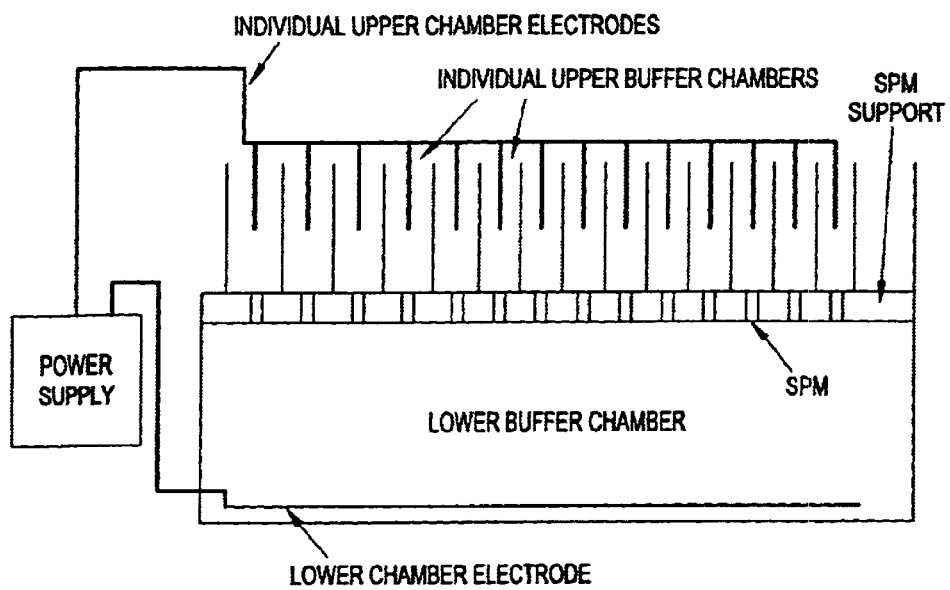
FIG. 3. Simple Embodiment of the Basic Device (b). In this embodiment, a device having multiplicity of first chambers each with a single first electrode and a common second buffer chamber with a single second electrode is shown.
Figure 4:
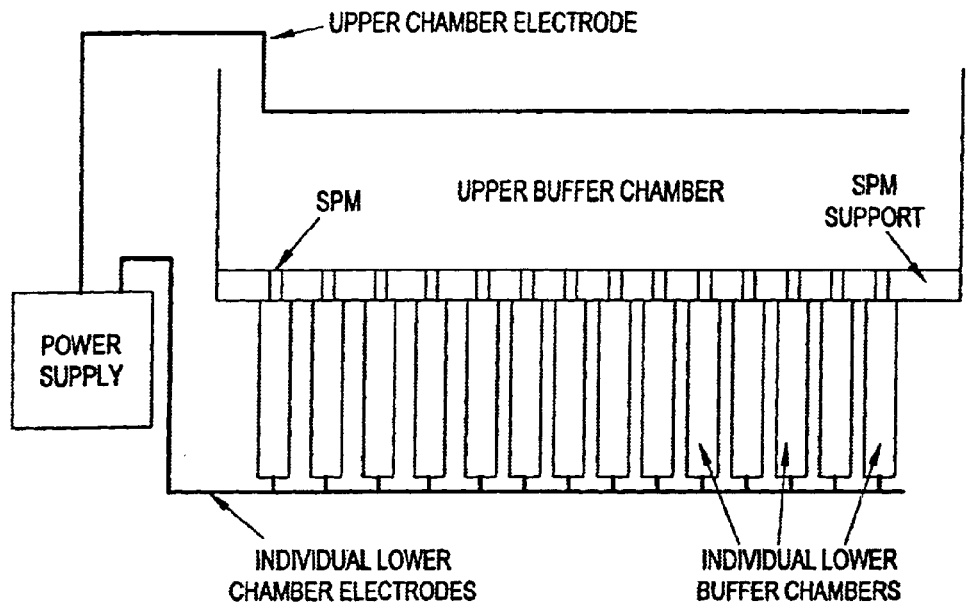
FIG. 4. Simple Embodiment of the Basic Device (c). In this embodiment, a device having a common first chamber with a single first electrode and a multiplicity of second chambers each with a single second electrode is shown.
Figure 5:
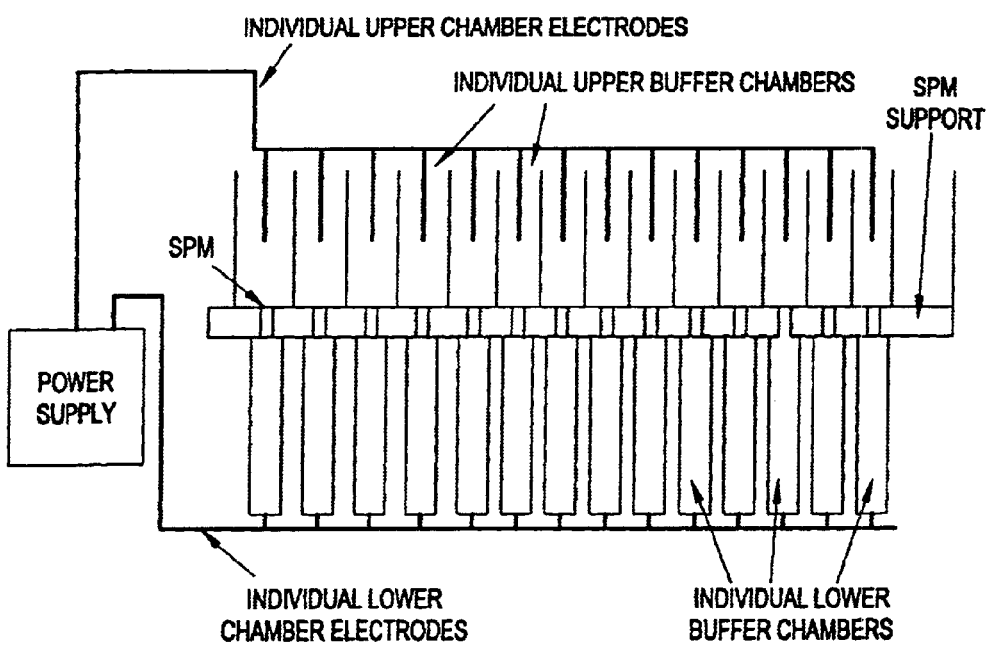
FIG. 5. Simple Embodiment of the Basic Device (d). In this embodiment, a device having multiplicity of first chambers each with a single first electrode and a multiplicity of second chambers each with a single second electrode is shown.

This aspect of the invention can be further refined if individual electrodes are utilized near each microlocation (FIGS. 3–5). When individual electrodes are used in the devices of the invention, the devices can electronically produce "different stringency conditions" at each microlocation. Thus, all hybridizations can be carried out optimally under the same temperatures and buffer conditions, despite disparate melting temperatures of the hybridization probes. These active devices are fundamentally different from conventional multiplex hybridization arrays, dot-blots, and DNA chips. While conventional arrays have different probes or target DNA's located at each site; all the sites on the array have the same common reaction or stringency conditions of temperature, buffer, salt concentration, and pH. Any change in the reaction or stringency condition affects all sites on the array. While sophisticated photolithographic techniques may be used to make an array, or microelectronic sensing elements may be incorporated for detection, conventional devices are passive and do not control or influence the actual hybridization process. When individual electrodes are used for each microlocation in the devices of the invention, hybridization conditions may be controlled for each individual location, making each a mini-test-tube with its own hybridization conditions.

Another important consideration is the composition of the transport and hybridization buffers and salts. To facilitate rapid movement of nucleic acids by free field electrophoretic transport, low conductivity buffers have been utilized in the first buffer reservoir. To achieve low conductivity and preserve good buffering capacity, zwitterionic buffers have been used that have little or no net charge at their pI. These buffers, typically possess conductivities less than 100 $\mu$S/cm. Buffers commonly employed in molecular biology have conductivities a thousand fold greater, e.g. 6×sodium chloride/sodium citrate (SSC). Low conductivity and zwitterionic buffers with little or no net charge do not optimally shield nucleic acid phosphodiester backbone charges and therefore, under passive conditions, do not aid in hybridization. While we do not wish to be bound by any particular theory, it is believed that this probably helps to prevent self annealing of denatured nucleic acids prior to transport, while free in the first buffer reservoir. Conversely, the second buffer reservoir contains some positively charged cationic entity whose diffusion into the first buffer reservoir is retarded by the SPM. When moved across the SPM by the applied electric potential, this cationic entity aids in the hybridization of DNA in the reaction zone adjacent to the SPM before diffusing into the first buffer reservoir. While we do not wish to be bound by any particular theory, it is believed that this probably helps to accelerate the annealing of complementary strands between probe and target nucleic acids at the surface of and within the SPM, while the cationic entity is still too diffuse to encourage self annealing of denatured nucleic acids in the greater volume of the first buffer reservoir.

By way of background, U.S. Pat. Nos. 5,605,662, 6,051,380 and 5,632,957 (and related patents) teach that electronic hybridization could be carried out in macroscale type devices. These devices were called "micro-machined" as opposed to the "microfabricated" chips or array devices. The patents teach that so-called "micro-machined" devices involved components that could have macroscopic or macroscale dimensions. Such devices included glass capillary tubes with polyacrylamide gels and capture oligonucleotides, fixed in devices with upper and lower buffer cambers with platinum wire electrodes. Other devices included electronic microtiter plate like devices for multiplex hybridization. In initial experiments using such devices, electronic hybridization was demonstrated using conventional or high salt buffers in both buffer chambers of these macroscale devices. The macroscale devices of the new invention now teach how hybridization can be carried out under substantially denaturing conditions, with low conductance buffers in a least one of the device chambers.

Thus, the disclosed devices can carry out multi-step and multiplex reactions with complete and precise electronic control, preferably under overall micro-processor control (i.e. run by a computer and supporting electronic interface). The rate, specificity, and sensitivity of multi-step and multiplex reactions are greatly improved at the test site microlocations on the disclosed device.

This invention may utilize test site microlocations of any size or shape consistent with the objective of the invention. In more preferred embodiments of the invention, test site microlocations in the 100 micron to 10 millimeter range are used.

As used herein, "specific binding entity" means any biological or synthetic molecule that has specific affinity to another molecule, macromolecule or cells, through covalent bonding or non-covalent bonding. Preferably, a specific binding entity contains (either by nature or by modification) a functional chemical group (primary amine, sulfhydryl, aldehyde, etc.), a common or unique sequence (for binding to nucleic acids), an epitope (for binding to antibodies), a hapten, or a ligand (biotin), that allows it to covalently react or non-covalently bind to a common functional group on the surface of a test site microlocation. Specific binding entities include, but are not limited to: nucleic acid polymers (deoxyribonucleic acids (DNA), ribonucleic acids (RNA), synthetic oligonucleotides, peptide nucleic acids (PNA), pyranosyl nucleic acids (pRNA),) antibodies, proteins, enzymes, peptides, lectins, modified polysaccharides, cells, synthetic composite macromolecules, functionalized nanostructures, functionalized microstructures, synthetic polymers, modified/blocked nucleotides/nucleosides, modified/blocked amino acids, fluorophores, chromophores, ligands, chelates and haptens.

By "stringency control" is meant the ability to discriminate specific and non-specific binding interactions by changing some physical or chemical parameter. In the case of nucleic acid hybridizations, temperature control is often used for stringency. Reactions are carried out at or near the melting temperature (Tm) of the particular double-stranded hybrid pair.

1.0 Buffers for Use in the Methods and Devices of the Present Invention 1.1 Basic Electrophoretic Principles The devices (referred to as electronically enhanced hybridization devices, "active" DNA chips/arrays, lab on a chip devices, microfluidic devices, micromachined devices, sample preparation devices, electronic dot blots, electronic microtiter plates, etc.) and methods of this invention involve the application of DC, and also DC/AC electric fields to effect the transport, to accelerate the reactivity, and to improve the specificity of charged reagent and analyte molecules and entities (DNA, RNA, enzymes, antibodies, proteins, cells, etc.). Thus, a basic understanding and definition of the physical parameters concerning the effects of electric fields on charged molecules, of electrophoretic transport, and the properties of different buffering agents and electrolytes (anions and cations) are important to this invention. Of particular importance to the invention are the physical effects and environment which occur around the SPM of the test site microlocation, near to where the electric field density is highest.

There are a number of physical parameters which relate to the electrophoretic transport of DNA and other charged analytes in various types of electrolyte and buffer solutions. The devices of this invention are basically DC (direct current) electrical devices which generate electric fields and produce a net current flow through the first and second buffer reservoirs via the SPM microlocations of the device. Additionally, a number of low frequency (~0.1 to 500 Hz) DC and DC/AC low frequency pulsing scenarios (which still produce a net current flow) can improve overall device performance, reagent and analyte concentration rates, DNA/RNA hybridization rates and efficiency, and the hybridization specificity. Also, using the systems and devices of this invention with special combinations of high frequency AC electric fields for cell selection and positioning, and DC electric fields for electrophoretic transport are disclosed for operations on the electronic devices (for sample preparation, bio-polymer synthesis, etc.). High frequency (kHZ to MHz) AC fields, which produce no net current flow, do not produce electrophoretic transport of charged molecules in solution. However, these high frequency AC fields, which produce a field gradient, can cause cells and other entities with different dielectric properties to align along the field gradient lines. This process is called dielectrophoresis.

With respect to DC fields (at voltages greater than ~1.0 to 1.5 volts) and pulsed DC and DC/AC fields, these electric fields do cause the electrophoretic transport of charged molecules to occur between oppositely (+/−) biased electrodes across the SPM of the microlocations or test locations on the device. Under these conditions the devices produce significant net direct current flow when a voltages greater than about 1.0 to 1.5 volts are applied. This production of current is considered "the signature of the electrophoretic process." In this process, the migration of ions or charged particles is produced by electrical forces along the direction of the electric field gradient, and the relationship of current and voltage are important to this process. The electrophoretic migration shows itself macroscopically as the conduction of electric current in a solution under the influence of an applied voltage and follows Ohm's law:

$$V = R \times I$$

where:

V is the electric potential (voltage)

R is the electric resistance of the electrolyte [$V \times A^{-1} = \Omega$]

I is the electric current [Ampere]

The resistance (R) of the solution is the reciprocal of the conductance (L) which can be measured by a conductometer. The conductance depends on the geometry of the measuring device, and on the ionic species of the buffer/electrolytes and their concentration. While broadly these same current/voltage relationships which form the basis for the electrophoresis techniques used in molecular biology research apply, the electric fields produced by the devices of this invention are focused into somewhat more microscopic environments, in that the electric field is concentrated and channeled through the SPM of the test site microlocations. Additionally, the electrolyte anions and cations ($Na^+$, $K^+$, $Cl^-$, etc.), the buffering agents (histidine, cysteine, tris, phosphate, citrate, etc.), and the analyte molecules (DNA, RNA, antibodies, enzymes, proteins, cells, etc.) also experience this very high electric field density at the test site microlocations.

In one aspect of this invention, this high electric field density appears to be an important property which can be utilized for the "electronic de-hybridization" of complementary and partially complementary DNA sequences (including single base differences) from the DNA sequences attached or tethered to the test site microlocations. This is the key mechanism for the process called "electronic stringency". The second electronic stringency mechanism is the more basic property of electrophoretically transporting unbound or non-specifically bound materials away from the microlocation test site. Finally, it should be pointed out that the devices and methods of this invention utilize the property of "electrophoretic transport", as opposed to technique of "electrophoresis", which is more properly defined as the use of an electric field to cause the separation of charged molecules through a sieving media.

In some aspects, the devices of this invention can be considered "engines" to move, transport and concentrate charged analytes, reagents from the buffer reservoirs to a hybridization zone on the upper surface of the SPM at the test site microlocation. In another aspect, the devices of this invention also produce a favorable hybridization environment at the test site microlocation. In another aspect, the devices of this invention can produce high local electric field densities which can be used to control, influence, affect, and improve the hybridization and de-hybridization processes occurring on the microlocation test sites.

There are unique features of the systems, devices, and methods of this invention which relate to the various ways of sourcing the current and voltage, and how various current and voltage scenarios are used to improve the performance of the systems. For example, an almost unlimited number of DC and DC/AC pulsing procedures (linear and logarithmic gradients) are possible which appear to provide significant improvements in reagent and analyte transport and concentration, DNA hybridization enhancement.

1.2 Electrophoretic Transport Versus Ionic Strength

It is well established in the field of electrophoresis that there is a logarithmic decrease in the mobility of the charged analyte entity (proteins, DNA, etc.), which is inversely proportional to the square root of the ionic strength of the electrolyte solution (see page 83 and FIG. 3.16 in "Capillary Electrophoresis: Principles and Practice", R. Kuhn and S. Hoffstetter, Springer-Verlag, 1993). At any given constant electric field strength, as the electrolyte concentration decreases relative to the analyte entity (protein, DNA, etc.), the analyte will be transported at a faster rate. Similar results demonstrating this effect for a dansylated amino acid have been shown by J. J. Issaq et. al., Chromatographia Vol. 32, #3/4, August 1991, pages 155 to 161 (see in particular FIG. 3 on page 157). Results demonstrating this effect for DNA in different electrolyte solutions has been shown in P. D. Ross and R. L. Scruggs, Biopolymers Vol. 2, pages 231 to 236, 1964 (see in particular FIG. 1, page 232).

Ionic Strength/Conductance Relationship—For those non-buffering electrolytes (sodium chloride, potassium chloride, etc.) which involve completely dissociated anion and cation species in solution ($Na^+ \leftrightarrows Cl^-$, $K^+ \leftrightarrows Cl^-$, etc.), the ionic strength and conductance are equivalent, i.e., the conductance will usually be proportional to the ionic strength. For those buffering electrolytes (phosphate, acetate, citrate, succinate, etc.) which are in their dissociated states (example: $2\ Na^+ \leftrightarrows PO_4^{-2}$), the ionic strength and conductance will usually be equivalent, i.e., conductance is proportional to the ionic strength. (A buffer has been defined as a chemical solution which is resistant to change in pH on the addition of acid or alkali. See., e.g., Dictionary of Biotechnology, Second Edition, James Coombs, Stockton Press. As stated there, "traditionally", buffers based on inorganic salts (phosphate, carbonate) and organic acid salts (acetate, citrate, succinate, glycine, maleate, barbiturates, etc.) were used in biological experiments. For those buffering electrolytes [Good Buffers (MOPS, HEPES, TAPS, Tricine, Bicine), Amino Acid Buffers, Ampholytes, etc.] which can have a zwitterionic species (no net charge at their pI), the conductance will decrease by approximately a factor of 10 for every pH unit difference between the isoelectric point (pI) and the (pKa). For example, an amino acid in its zwitterionic state ($^-OOC-CH(R)-NH_3^+$) will have a conductance value which will be approximately 1000 fold lower than when the "amino acid moiety" has a full net positive charge ($HOOC-CH(R)-NH_2^+ \leftrightarrows X^-$), or a full negative charge ($Y^+ \leftrightarrows\ ^-OOC-CH(R)-NH_2$). Thus, a formal negative or positive charge develops on the amino acid moiety as it moves away from its pI, and the conductivity and ionic strength will begin to correlate. However, when at or near the pI the conductance will be much lower than is expected for that given ionic strength or concentration. When used at or near their pI's, electrophoresis texts refer to the Good Buffers and amino acid buffers as having "low conductance's at high ionic strength or concentration" (see page 88 of Capillary Electrophoresis: Principles and Practice", R. Kuhn and S. Hoffstetter, Springer-Verlag, 1993). A commonly used electrophoresis buffer "Tris-Borate" actually has a significantly lower conductivity than would be expected from its ionic strength or concentration. This may be due to the "tris cation" and "borate anion" forming a relatively stable zwitterionic complex in solution. The conductivity of a 100 mM Tris-Borate solution was determined to be 694 $\mu$S/cm, which is approximately 20 times lower than would be expected from its ionic strength, and is roughly equivalent to a 5 mM sodium phosphate or sodium chloride solution. Table 1 shows conductivity measurements of a number of transport buffers.

TABLE 1

| Solution/Buffer | Measurement 1 | Measurement 2 | Measurement 3 | Average/Std. Deviation |
|---|---|---|---|---|
| 10 mM MgCl$_2$ | 1.95 mS/cm | 2.02 mS/cm | 2.13 mS/cm | 2.03 +/− 0.09 mS/cm |
| 1 mM MgCl$_2$ | 174 $\mu$S/cm | 208 $\mu$S/cm | 177 $\mu$S/cm | 186 +/− 18.8 $\mu$S/cm |
| 0.1 mM MgCl$_2$ | 16.9 $\mu$S/cm | 16.7 $\mu$S/cm | 18.3 $\mu$S/cm | 17.3 +/− 0.87 $\mu$S/cm |
| 10 mM NaCl | 1.07 mS/cm | 1.10 mS/cm | 1.18 mS/cm | 1.12 +/− 0.057 mS/cm |
| 1 mM NaCl | 112 $\mu$S/cm | 115 $\mu$S/cm | 111 $\mu$S/cm | 112.7 +/− 2.08 $\mu$S/cm |
| 0.1 mM NaCl | 8.80 $\mu$S/cm | 8.98 $\mu$S/cm | 10.5 $\mu$S/cm | 9.43 +/− 0.93 $\mu$S/cm |
| 20 mM NaPO$_4$ | 2.90 mS/cm | 2.79 mS/cm | 3.00 mS/cm | 2.90 +/− 0.11 mS/cm |
| 10 mM NaPO$_4$ | 1.40 mS/cm | 1.44 mS/cm | 1.48 mS/cm | 1.44 +/− 0.04 mS/cm |
| 1 mM NaPO$_4$ | 122 $\mu$S/cm | 128 $\mu$S/cm | 136 $\mu$S/cm | 128.7 +/− 7.0 $\mu$S/cm |
| 50 mM TRIS | 3.50 mS/cm | 3.14 mS/cm | 3.40 mS/cm | 3.35 +/− 0.19 mS/cm |
| 10 mM TRIS | 572 $\mu$S/cm | 562 $\mu$S/cm | 583 $\mu$S/cm | 572 +/− 10.5 $\mu$S/cm |
| 250 mM HEPES | 141 $\mu$S/cm | 144 $\mu$S/cm | 158 $\mu$S/cm | 147.6 +/− 9.07 $\mu$S/cm |
| 25 mM HEPES | 9.16 $\mu$S/cm | 9.44 $\mu$S/cm | 10.5 $\mu$S/cm | 9.7 +/− 0.71 $\mu$S/cm |
| 3.3 mM NaCitrate | 964 $\mu$S/cm | 964 $\mu$S/cm | 1.03 mS/cm | 986 +/− 38.1 $\mu$S/cm |
| 5 mM NaSuccinate | 1.05 mS/cm | 960 $\mu$S/cm | 1.01 mS/cm | 1.01 +/− 0.045 mS/cm |
| 5 mM NaOxalate | 1.02 mS/cm | 1.03 mS/cm | 1.12 mS/cm | 1.06 +/− 0.055 mS/cm |
| 10 mM NaAcetate | 901 $\mu$S/cm | 917 $\mu$S/cm | 983 $\mu$S/cm | 934 +/− 43.5 $\mu$S/cm |
| 250 mM Cysteine | 27.4 $\mu$S/cm | 17.3 $\mu$S/cm | 23.5 $\mu$S/cm | 22.7 +/− 5.09 $\mu$S/cm |
| Milli-Q water | <0.5 $\mu$S/cm | | | Detection limit of 0.1 cell too low |

Certain advantages exist regarding the rate or speed of electrophoretic transport of DNA when using Zwitterionic buffers (Good buffers, amino acid buffers), or the Tris-Borate buffer at or near their pI's, these are: 1) these buffers can be used at relatively high concentrations to increase buffering capacity; 2) their conductance's are significantly lower than other types of buffers at the same concentration, and 3) one gains the advantage of higher electrophoretic transport rates for the analyte of interest (DNA).

Several electrophoretic techniques developed over 20 years ago are based on the ability to separate proteins in zwitterionic buffers "at their pI's": these techniques are called Isoelectrophoresis, Isotachophoresis, and Electrofocusing (see chapters 3 and 4 in "Gel Electrophoresis of Proteins: A Practical Approach" Edited by B. D. Hames & D. Rickwood, IRL Press 1981). Various amino acid buffers and Good buffers were used for these applications, all at their pI's (see Table 2, page 168 of the above reference).

While a given amino acid may or may not have its "highest buffering capacity" at its pI, it will have some degree of buffering capacity. Buffer capacity decreases by a factor of 10 for every pH unit difference between the pI and the pKa; those amino acids with three ionizable groups (histidine, cysteine, lysine, glutamic acid, aspartic acid, etc.) generally have higher buffering capacities at their pI's than those amino acids with only two dissociation's (glycine, alanine, leucine, etc.). For example, histidine pI=7.47, lysine pI=9.74, and glutamic acid pI=3.22, all have relatively good buffering capacity at their pI's, relative to alanine or glycine which have relatively low buffering capacities at their pI's (see A. L. Lehninger, Biochemistry, 2ed, Worth Publishers, New York, 1975; in particular FIGS. 4–8 on page 79, and FIGS. 4–9 on page 80). Histidine has been proposed as a buffer for use in gel electrophoresis, see, e.g., U.S. Pat. No. 4,936,963, but hybridization is not performed in such systems. Cysteine is in a more intermediate position, with regard to buffering capacity. The pI of cysteine is 5.02, the pKa for the α-carboxyl group is 1.71, the pKa for the sulfhydryl is 8.33, and the pKa for α-amino group is 10.78. An acid/base titration curve of 250 mM cysteine, shows that cysteine has a better "buffering capacity" at ~pH 5 than a 20 mM sodium phosphate. In the pH 4 to 6 range, the buffering capacity of cysteine is significantly better than 20 mM sodium phosphate, particularly at the higher pH. However, in these pH ranges the conductance of the 250 mM cysteine solution is very low ~23 µS/cm, compared to 20 mM sodium phosphate which has a value of ~2.9 mS/cm, a factor of 100 times greater.

In addition to ionic strength of the electrolyte solution, the mobility of the charged analyte entity (DNA, proteins, etc.) is related to the nature of the cation and anion species in the electrolyte solution (see pp 89 of "Capillary Electrophoresis: Principles and Practice" reference). This particular point is demonstrated for DNA transport in the above Biopolymers, Vol. 2, pp. 231–236, 1964 reference. FIG. 1 on page 232 of this reference shows the change in DNA mobility when using electrolytes with different univalent anions ($Li^+>Na^+>K^+>TMA^+$) at the same ionic strength. Basically, different cations can have different association constants with the DNA phosphate groups, and/or change the hydration spheres around the DNA molecules, which leads to a change in their transport rate. In addition to the effect on mobility, different cations may effect the relative stability of double stranded DNA.

1.3 Composition of First and Second Buffers for Use in the Invention

Many aspects of this invention relate to our discoveries concerning the various parameters including, DC and DC/AC pulsing scenario's, special electrolytes and buffers for use in the first and second buffer reservoirs (histidine, cysteine etc.), and other conditions which improve or optimize the speed of reagent or analyte (DNA, RNA, etc.) transport, the efficiency of DNA or RNA hybridization reactions, and the overall hybridization specificity in these electronic systems and devices. As was disclosed in our earlier patent applications, various low conductance and zwitterionic buffers, including but not limited to D- & L-histidine, di-histidines, histidine peptides, 1 & 3 methyl-histidines, carnosine, imidazole, pyridine and collidine provided: (1) rapid electrophoretic transport of the DNA; (2) DNA concentration at the test site microlocation, and (3) efficient hybridization reactions in the single-buffer microelectronic chip devices (APEX or NanoChip™ devices). Single-buffer is used in the context of only one buffer at a time being used in the single-buffer reservoir or chamber associated with the planar microchip devices. In contrast, other zwitterionic buffers such as cysteine, glycine, β-alanine and γ-amino-butyric acid (GABA) provide rapid transport, but do not facilitate efficient hybridization under these conditions. When using these buffers for transport and concentration of DNA, hybridization can be achieved by rapidly replacing the buffer with a more classical hybridization buffer (100 mM NaCl & $Na_2PO_4$, etc.) immediately after appropriate DNA concentration has occurred at the test site microlocation.

The effect on hybridization efficiency produced by histidine buffers, in particular, was unexpected. It was noted during experimentation that although several zwitterionic buffers were good transport buffers for concentrating DNA at the test site microlocations of planar microchip DNA devices (the APEX or NanoChip™ devices), this usually did not promote stable hybridization of DNA species. However, zwitterionic histidine which becomes positively charged in the slightly acidic environment produced by the anode (positively biased microelectrode), does now stabilize the hybridized DNA backbone at the microelectrode sites of the microchip devices. During the transport and addressing procedures for DNA concentration and hybridization, the pH immediately above the positively biased electrode is found to be lowered. In separate experiments, it was observed for passive hybridization at acidic pH that histidine can facilitate hybridization when NOT its zwitterionic state. (see Edman, et al., Nucleic Acids Research (1997) Vol. 25, pp 4907–4914).

The advantage of histidine, di-histidines and the other hybridization enhancing buffers, is particularly important for the operation of the planar microchip or microarray type (APEX and NanoChip™) devices where the permeation layer is very near or in direct contact with the microelectrode surface (platinum). These devices usually have 10 micron to 100 micron diameter test site microlocations, and are produced on a silicon substrate using microlithographic techniques.

Generally, in these devices (as opposed to the larger scale devices of the invention) the microelectrodes (platinum) are covered with about one to ten microns of a hydrogel type permeation layer (agarose or acrylamide). These planar microchip devices are operated at a lower range of currents (~10 nA to ~5 uA) and voltages (~1.2 to 5.0 volts). These lower currents and voltages (which still produce electrophoretic transport) are used to reduce active bubbling at the positive and negatively biased microelectrode/permeation layer interface. Oxygen gas is produced at the positive electrode and hydrogen gas is produced at the negative electrode, but the gases are dissipated by diffusion, as opposed to active bubbling. At these lower currents (~10 nA to ~5 uA) and voltages (~1.2 to ~5.0 volts) one finds that the DNA transport rate is reduced when higher conductance buffers and electrolytes (>10 mM NaCl, KCl, sodium phosphate, sodium citrate, sodium borate, Tris, etc.) are used. Additionally, the concentration of the polyanionic nucleic acids is slowed by the competing concentration of the smaller and more numerous electrolyte anions (phosphate, citrate, Cl$^-$, etc.) which amass at the permeation layer surface of the positively biased microlocations. Finally, the ability of target DNA sequences to hybridize to the DNA sequences attached to the test sites is greatly reduced, due to the highly concentrated anionic environment and to corresponding lack of stabilizing cations. It should be kept in mind, that conversely the concentration of the smaller electrolyte cations (Na$^+$,K$^+$,Tris, etc.) is also occurring at the permeation layer surface of the negatively biased microlocations. Also, under low buffering conditions (<10 mM) or when the main buffer component is not an anionic species (phosphate, citrate, borate, etc.), the production of a low pH (<4) acidic environment at the positively biased microlocation reduces the nucleic acid hybridization efficiency and can also can promote precipitation of the DNA or RNA on and within the permeation layer. Conversely, the production of an unbuffered high pH (>10) basic environment at the negatively biased microlocation can have adverse effects.

It is believed that the low conductivity of the histidine buffer system accounts for the rapid transport and concentration (accumulation) of the DNA. There are several explanations as to why the histidine buffer produces relatively efficient DNA/DNA hybridization. One advantage is the good buffering capacity of histidine. With its pI at 7.47, histidine will buffer well under both acidic or basic conditions (see A. L. Lehninger, Biochemistry, 2ed, Worth Publishers, New York, 1975, FIGS. 4–9 on page 80). In the case of the APEX or planar microchip devices, the positively biased microelectrode that provides the electric field necessary to accumulate the DNA for hybridization at the test site microlocation also produces acid, and the histidine may effectively buffer these conditions. In its zwitterionic state, the concentration of histidine can remain high in the local vicinity of both the positively and negatively biased microlocations. More probably and importantly, under the acidic conditions (pH<6) produced at the positively biased microelectrode, the protonation of the imidazole group on histidine begins to convert the molecule into a more di-cationic species. This di-cationic species with a positively charged α-amino group and a positively charge imidazole group promotes hybridization and stabilizes the DNA/DNA hybrids formed at the positively biased test site microlocations on the planar microchip type devices. Cations, di-cations, and polycations are known to help stabilize DNA/DNA hybrids by reducing the repulsion of the negatively charged phosphate backbones on the double-stranded DNA structure. Thus, histidine suggests the design of other compounds (histidine polypeptides, mixed peptides, synthetic derivative, etc.) which have zwitterionic, low conductance, and di-cationic, or multi-cationic character for improving electronic hybridization on the APEX or Nano-Chip™ devices.

Because the devices and methods of the present invention utilize electric fields generated by electrodes which are relatively remote from (i.e., millimeters rather than micrometers) the test site microlocation, the buffers for use in the devices and methods of the present invention are not as limited by the above considerations. For example, Table 2 shows the results for a series of experiments which correlate the parameters of buffer capacity, pH, and the conductivity, with DNA motility or transport rate:

TABLE 2

| Solution | Ionizable groups | pH in water | Conductivity ($\mu$S/cm) & [conc'n] | Relative Transport Rate |
|---|---|---|---|---|
| β-Alanine | pK$_1$ - 3.6<br>pK$_2$ - 10.2 | 6.7 | 4 [50 mM] | +++++ |
| Cysteine | pK$_1$ - 1.7<br>pK$_2$ - 8.3<br>pK$_3$ - 10.8 | 5.1 | 22 [250 mM] | ++++ |
| Histidine | pK$_1$ - 1.8<br>pK$_2$ - 6.0<br>pK$_3$ - 9.0 | 7.6 | 60 [50 mM] | +++ |
| NaPO$_4$ | Complex (adjusted to pH 7.4) | 7.4 | 1,400 [20 mM] | + |

In particular, Table 2 shows the effect of various zwitterionic amino acid buffers (β-Alanine, Cysteine, Histidine) and Sodium Phosphate (not a zwitterionic buffer) on the transport of target DNA to charged test sites. The transport generally correlates with conductivity under the same field conditions. β-alanine, and cysteine show excellent transport, histidine shows good transport, and NaPO$_4$ shows fair transport. In short Table 2 clearly shows the correlation of DNA transport and concentration with low conductivity (β-alanine, cysteine, histidine).

An additional benefit of low conductance buffers when used as a first buffer in the devices of this invention is the relative denaturing condition for the DNA target sequences in such solutions. This denaturing condition may also reduce secondary structure effects in target DNA sequences and competing hybridization from the complementary target strands.

In the present invention, because of favorable first charged entity transport and concentration in zwitterionic buffers "at their pI", these buffers preferred for use in first (upper) buffer reservoir. Thus, when a potential is applied across the test site microlocation, the first charged entity rapidly migrates through the first buffer reservoir to the upper surface of the SPM. Preferred zwitterionic buffers (e.g., histidine β-alanine, cysteine, glycine, ε-amino caproic acid, taurine, methylhistidine, lysine, γ-amino, butyric acid, carnosine) for use in the first buffer reservoir have a significant buffering capacity, and have an initial conductance of less than 1000 $\mu$S/cm, more preferably 250 $\mu$S/cm, more preferably less than 100 $\mu$S/cm, and most preferably less than 50 $\mu$S/cm. Because of intrinsic contaminants in most reagents, persons of skill in the art are rarely able to obtain conductance levels of less than 0.1 $\mu$S/cm in most zwitterionic buffers. Depending upon the nature of the zwitterion, or other buffer species, the concentration of the buffer species can range from 1 mM to 500 mM, more preferably from 10 mM to 300 mM, and most preferably from 25 mM to 200 mM. For DNA applications, a buffer whose pI is at a pH which does not adversely effect the hybridization process or the DNA molecules themselves is preferred. Histidine, whose pI is 7.47, is particularly preferred for the electronic hybridization applications. For other applications, antigen/antibody interactions, enzymatic reactions, synthesis, etc., other zwitterionic buffers whose pI's are at other pH's may be preferred in order to optimize those particular reactions. For instance, an antibody reaction with an acid-labile antigen might be carried out with a lysine zwitterionic buffer as the first buffer solution. In addition, the necessity of maintaining a charge on the first charged entity will often dictate that the first buffer has a pI in a certain pH range. Finally, the upper buffer chamber can also contain chaotropic agents, solvents, non-ionic detergents, polysaccharides, synthetic precursors, cofactors, chelates, ligands, other amino acids, peptides, and/or proteins to aid in achieving the desired reaction performance.

Because of the preference for rapidly transporting the second charged entity to the lower side of the SPM, and through to the upper side of the SPM into the test site microlocation reaction zone, the second buffer composition is preferably based upon a zwitterionic buffer "about or below its pI", where the buffer molecule now has a formal positive or negative chage. However, because the second buffer will also contain the second charged entity, the conductance of the second buffer will usually be, much greater than that of the first buffer. The selection of the second charged entity for inclusion in the second buffer will be guided by number of factors. The first factor is the nature of the reaction being controlled at the test site microlocation and the effect that the practitioner of the invention wishes to have on that reaction. For instance, it is well known in the art that some cations in solution are necessary to properly stabilize a DNA double helix backbone upon hybridization, as illustrated by the protonated histidine in FIG. 7. In addition, for DNA hybridization reactions, dissociated cations (e.g., $NH_4^+$, positively charged amino acids, positively charged oligopeptides, positively charged detergents, protonated amines, and metal cations such as $Na^+$, $K^+$, $Ag^+$, $Cu^+$, $Mg^{+2}$, $Ca^{+2}$, $Zn^{+2}$, $Cu^{+2}$, $Ni^{+2}$, $Co^{+2}$, $Fe^{+2}$, $Se^{+2}$, $Mn^{+2}$, $Al^{+3}$, $Cr^{+3}$, $Fe^{+3}$, $Co^{+3}$, $Mn^{+4}$, $Se^{+4}$, and organically chelated metal cations) are desirable second charged entities to include in the second buffer reservoir to accelerate and stabilize the electronic hybridization reaction. For other reactions, other entities such as detergents, chaotropic agents, solvents, metal ions, ligands, cofactors, synthetic precursors; other amino acids may be chosen for their ability to accelerate, inhibit and/or participate in the desired reaction.

Although many cations which are of sufficient size for controlled transport form the second buffer chamber through the SPM to the reactions zone of the test site/microlocation may be used, histidine and/or histidine derivatives are some of the more preferred buffer cations for use in the electronic DNA hybridization applications of the present invention. Basically, di-cationic histidine provides very good stabilization of the double-stranded DNA structures under electronic hybridization conditions. Indeed, upon examining CPK space filling molecular structures of histidine and ds-DNA, the di-cationic histidine entity appears to have good fit with phosphate oxygen anion spacing along the DNA backbone, promoting electrostatic interaction. Furthermore, the CPK space filling structures suggested that di-histidine and other di-, tri-, and polypeptide structures will further significantly stabilize ds-DNA structures. It is believed that in addition to these peptide structures, a large number of peptide derivatives and synthetic structures can be designed to stabilize ds-DA under electronic hybridization conditions.

The second factor which should be taken into account when choosing the second charged entity is its ability to maintain a charge in the second buffer solution which is opposite the charge of the first charged entity. This is necessary in order to transport the second charged entity across the microlocation SPM for interaction with the anchored specific binding entity and the first charged entity. For DNA hybridization reactions, this consideration is rather tautological, as the preferred cation second charged entities are, per se, of the opposite charge. However, if the preferred second charged entity is a detergent, metal ion, or other species, some care should be taken when choosing buffer conditions which will produce the oppositely charged first and second charged entities (e.g., enzyme reactions).

As one of ordinary skill will perceive, it is not necessary for the second charged entity to maintain its charge upon contact with the first buffer, or with the first charged entity and the specific binding entity. In fact, in instances when the charge of the second charged entity is not necessary for its function in accelerating or inhibiting the reaction at the microlocation, it may be desirable for the second charged entity to lose its charge upon entering the first buffer solution (e.g., generating non-ionic detergents or similar such compounds at the reaction zone). Thus, the localized concentration of the now-uncharged second charged entity will increase even faster at the microlocation, as the electromotive force no longer pulls on the second charged entity, and only passive diffusion forces clear the entity from the microlocation.

The third factor to be taken into account when choosing the second charged entity for inclusion in the second buffer is the rate that the second charged entity will diffuse through the SPM. If the first and second factors stated above do not pose significant limitations upon second charged entity, such as cations for the stabilization of DNA hybridization reactions, then a charged entity may be chosen whose size characteristics are compatible with any convenient SPM composition, chosen as described below. The second charged entity should not be able to freely diffuse across the SPM in a short time frame, but should be able to quickly move across the SPM when an electric field is applied across the microlocation. For instance, in devices for use in DNA hybridization reactions in which an agarose hydrogel (impregnated with streptavidin) of about 1–5 mm thickness is used as the SPM, a charged amino acid species, such as di-cationic histidine, is one of more preferred second charged entities. These species are of such size that their migration through the SPM hydrogel by passive diffusion is significantly retarded but will rapidly migrate through the SPM hydrogel when an appropriate electric field is applied. For other applications, in which the options or the second charged entity are more specific (e.g., $Ca^{++}$, $Zn^{++}$, $Mg^{++}$, $Mn^{++}$, $Co^{++}$, $Fe^{++}$), the SPM should be designed to prevent free diffusion of these entities in the absence of an applied electric potential. For instance, one could use a SPM with a positively charged lower surface. This would inhibit the diffusion of small, positively charged species across the SPM in the absence of an electric field.

Once the appropriate second charged entity has been chosen, the second buffer may be formulated to include the charged entity. It is preferable that the second charged entity be present in the second buffer in a sufficient concentration so that the second charged entity migrates across the SPM in sufficient amounts to cause the desired effect (acceleration or inhibition) on the reaction occurring in the reaction zone at and around the upper surface of the SPM. This concentration will be somewhat entity-specific and will depend, among other factors, upon the rate of migration (as controlled by the electric field) across SPM, the effective concentration necessary to achieve the desired effect upon the reaction, and the rate of diffusion of the second entity away from the test site microlocation reaction zone into the first buffer chamber. As a practical matter the concentrations which are optimal for any particular second charged entity may be determined empirically through routine experimentation by those of ordinary skill in the art. For use in electronic DNA hybridization applications with an agarose or polyacrylamide hydrogel SPM approximately 1 to 5 mm in thickness, the use of a histidine buffer with about 10 mM to about 100 mM, more preferably about 50 mM di-cationic histidine has yielded acceptable results (the concentration of di-cationic species is determined both by the actual buffer concentration and the pH to which it has been adjusted).

In order to strictly control the reaction within the test site reaction zone, it is also desirable that the second charged entity not be present in the bulk of the first buffer solution a concentration sufficient to effect the reaction. Usually, the ratio of the initial concentration of the second charged entity in the first buffer to the initial concentration of the second charged entity in the second buffer will be less than 1/1, more preferably less than 1/10, more preferably less than 1/100, and most preferably less than 1/1000.

2.0 Design and Fabrication of the Basic Devices for Use in the Methods of the Invention

2.1 Structural Design and Fabrication

Figure 2:
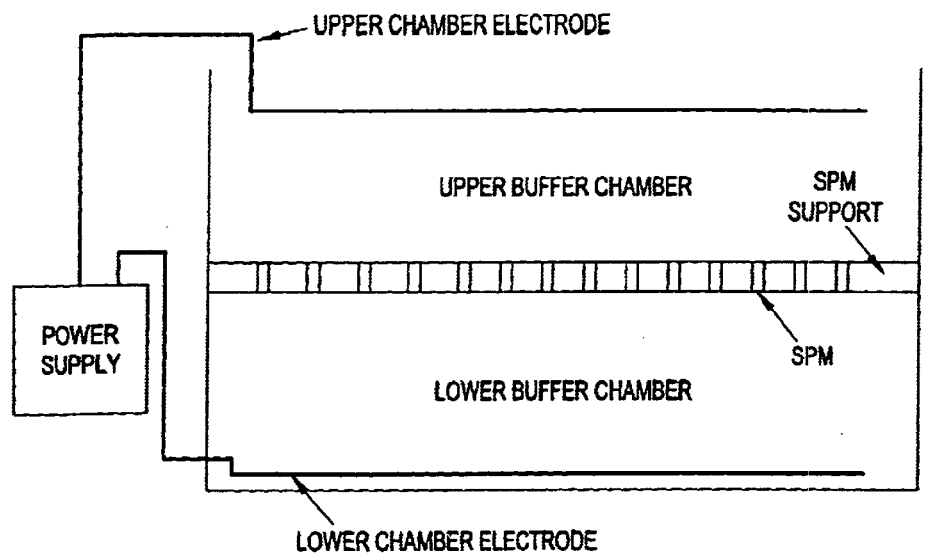
FIG. 2. Simple Embodiment of the Basic Device (a). In this embodiment, a device having a common (i.e. servicing a multiplicity of SPM test sites) first chamber with a single first electrode and common second chamber with a single second electrode is shown.
Figure 8:
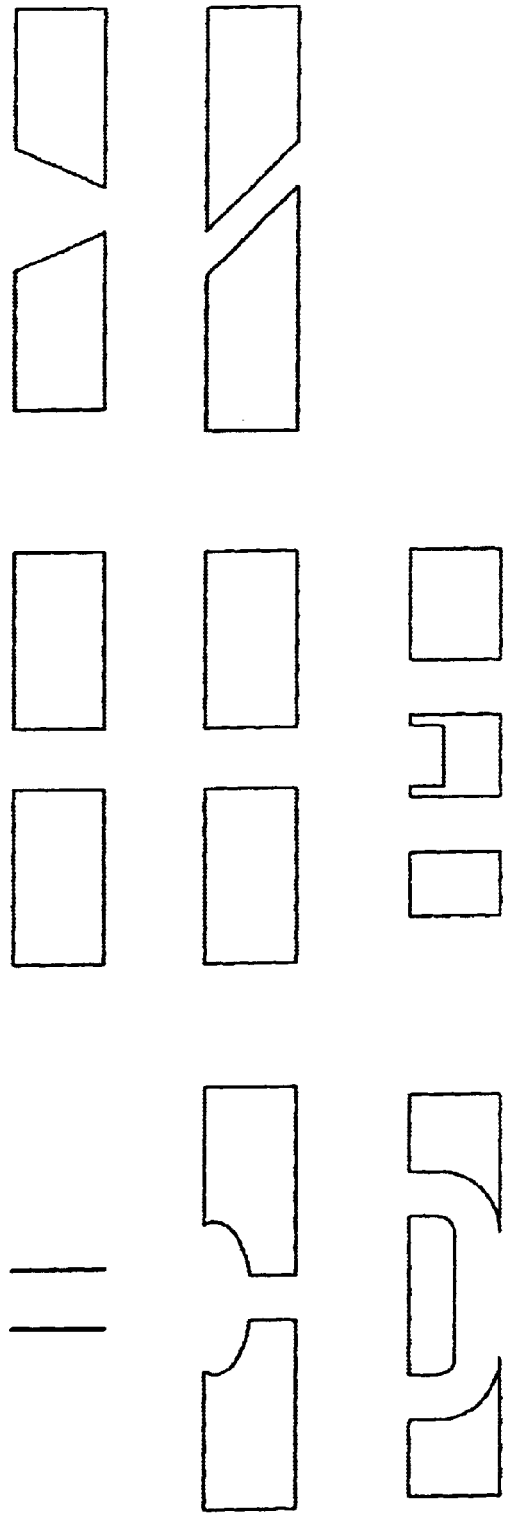
FIG. 8. Various Support Structure Geometries to Aid Sample Loading. Shown are possible well and capillary geometries to aid sample loading at test sites microlocations.
Figure 9:
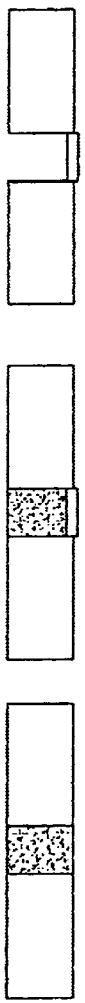
FIG. 9. SPM Embodiments in a Single Form of Test Site Support Design. Shown are various possible SPM embodiments employing both gel (hydrogel, sol gel, etc.) and/or membrane structures in a simple test site support design.
Figure 9:
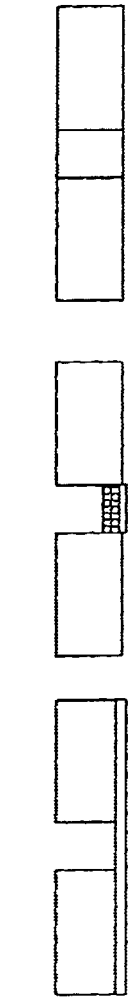
Figure 9:
Figure 9:
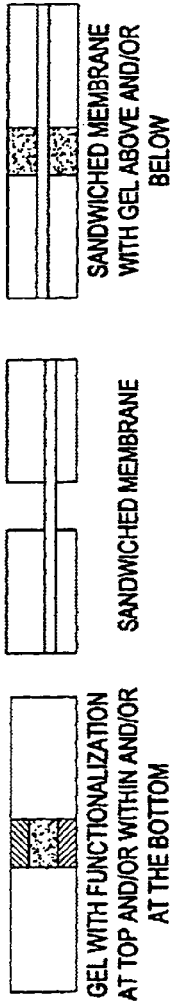

In order for the devices of the invention to actively carry out multi-step and multiplex reactions, they must have electronic components which actively operate in aqueous solutions to support electrophoretic transport. To satisfy this requirement, each test site microlocation must be electronically coupled to two functioning electrodes (for positive and negative bias) through the first and second buffer reservoirs. The test site microlocations can share a common electrode, have independent electrodes, or have independent electrodes on one side and a common electrode on the other site (or various combinations thereof). Thus, the basic conceptual components of the device structure are a first buffer reservoir (chamber) with a first electrode, a second buffer reservoir (chamber) with a second electrode, and a structural component with test site microlocation(s) which separates the two reservoirs (see FIGS. 1 and 2). The test site microlocations comprise a semi-permeable matrix (SPM) which allows controlled selective transport between the two reservoirs when an electric field is applied. The SPM structure is capable of serving as support for attaching specific binding entities and/or to create a zone for controlling reactions (hybridization, affinity, synthetic, catalytic, etc.). As will be evident to one of ordinary skill in the art, these components may be arranged in a variety of functional ways. For instance, the structural component separating the reservoirs can be comprised of insulatory material such as glass, silicon, plastic, rubber, and/or ceramics, with the test site microlocations fabricated within this structure. In other cases, an insulatory structural material can be used to hold a more general semi-permeable matrix material (filter paper, membrane, hydrogel, etc.) onto which binding entities are attached, thus forming the test sites/microlocations. Furthermore, the scope of the invention is not limited to particular physical shapes or spatial arrangements of these components. To emphasize this point, both "gaskets-sandwiched" and U-shaped formats of the devices of the invention have been illustrated in FIGS. 8, 9, and 10. In addition, indentations may be formed by at the test site/microlocations within a common buffer reservoir in order to aid in sample loading. Various configurations for such indentations are illustrated in FIGS. 8 and 9. Other considerations for the design and fabrication of a device include, but are not limited to, materials compatibilities, nature of the specific binding entities and the subsequent reactants and analytes, and the number of desired test sites microlocations.

By "a controllable and functioning electrode" is meant an electrode biased either positively or negatively, operating in a direct current mode (either continuous or pulse or DC/AC), which can in a controllable manner affect or cause the free field electrophoretic transport of the charged entity. The electrodes used in the devices of the invention may be provided in the form of wires or pins contacting the buffer reservoirs, or may be molded into the buffer reservoir walls or separating structure. Such integrated electrodes may be formed by conventional molding techniques. In addition, electronic circuitry for the parallel, serial, or individual control of the electrodes may be built within the device itself by integrated circuit techniques, or as a part of the power supply.

A device can be designed to have as few as one or two test site microlocations or many thousands of microlocations. It is also within the scope of this invention to include high throughput systems, in which a continuous sheet of filter paper, membrane or other semipermeable matrix material is pre-addressed with reactants or affinity binding agents (forming test site microlocations), and then processed through the electronic component device. In general, a more complex device with a large number of test site microlocations would be fabricated using micromachining, or perhaps microlithographic techniques. High-tolerance molding procedures may also be utilized for fabricating the devices of this invention. In most applications, a combination of high-tolerance molding techniques to create buffer reservoirs and micromachining techniques to create the microlocations themselves will be desirable, especially where larger common buffer reservoirs are utilized. Fabrication is carried out using organic polymers or other suitable substrate materials, such as glass, silicon dioxide, rubber, plastic, insulated metallic or ceramic materials. Depending upon intended detection method, materials which produce the lowest background signal are particularly preferred for device fabrication. Certain glasses and black plastics, for instance, have extremely low fluorescence background and are preferred for applications where fluorescent detection will be used.

Depending on the SPM utilized and the geometry of the device, molding of several pieces to be assembled into the functional device may be desirable. For instance, the U-format devices of FIGS. 8 and 9 would most likely be assembled by adhesive or other methods from several machined or molded pieces to create the proper test site microlocation structures between the first and second buffer reservoirs. Also, simpler devices such as that depicted in FIG. 10 may be pressure-fitted with rubber gaskets and O-rings in order to form common upper and lower buffer reservoirs for use in enabling the methods of the invention.

The test site microlocations can be of any shape, preferably round, square, or rectangular. The test site microlocations can range in size from 5 microns to 10 millimeters, with 100 microns to 5 millimeters being the preferred size range for devices fabricated using the micromachining techniques. It is also well within in the scope of this invention to use macrolocation test sites which have size ranges from 1 centimeter to 20 centimeters, with 2 to 5 centimeters being the most preferred. It is also anticipated that the devices of this invention could be used in industrial (bioreactors, etc.), environmental, and agricultural applications where even larger systems would be used. For DNA hybridization analysis applications, the size range 200 micros to 2 millimeters is most preferred to adequately concentrate the target DNA analyte for detection. While microlocations around 1 millimeter in diameter are desirable for analytical and diagnostic type applications, larger microlocations, or "macrolocations" (e.g., larger than 10 millimeters) are desirable for applications such as, but not limited to, DNA complexity reduction clinical or biological sample preparation, preparative scale biopolymer (oligonucleotide or peptide) synthesis, cell manipulations, etc.

The microlocation devices can be fabricated relatively easily using micro-machining or other standard fabrication techniques used to make common molecular biology laboratory devices such as microtiter plates, small electrophoresis chambers, dot blot devices and manifolds, etc. FIG. 10 is a schematic of a representative two-row 12 test site microlocation device. This microlocation device is fabricated from suitable plastic stock materials (11 cm×5 cm×0.3 cm), by drilling 12 proportionately spaced holes (1 mm in diameter) through the material. The semi-permeable matrix for the test site microlocations is then formed by filling the holes with 20% polyacrylamide impregnated with streptavidin (other devices have utilized an agarose hydrogel impregnated with streptavidin). Similarly, the first and second buffer reservoirs may be machined from appropriate plastic stock (11 cm×5 cm×0.6 cm), holding approximately 3 to 5 milliliters of buffer. Platinum wire electrode structures are designed to extend down into and along the middle of the common first and second buffer reservoirs. The first and second buffer reservoirs are then clamped together with the test site microlocation component using rubber gaskets to create a water-tight seal. After filling the first and second buffer reservoirs, the electrode wiring is connected to a DC power supply (BioRad Powerpack 1000 or a Keithley Model 236).

Figure 6:
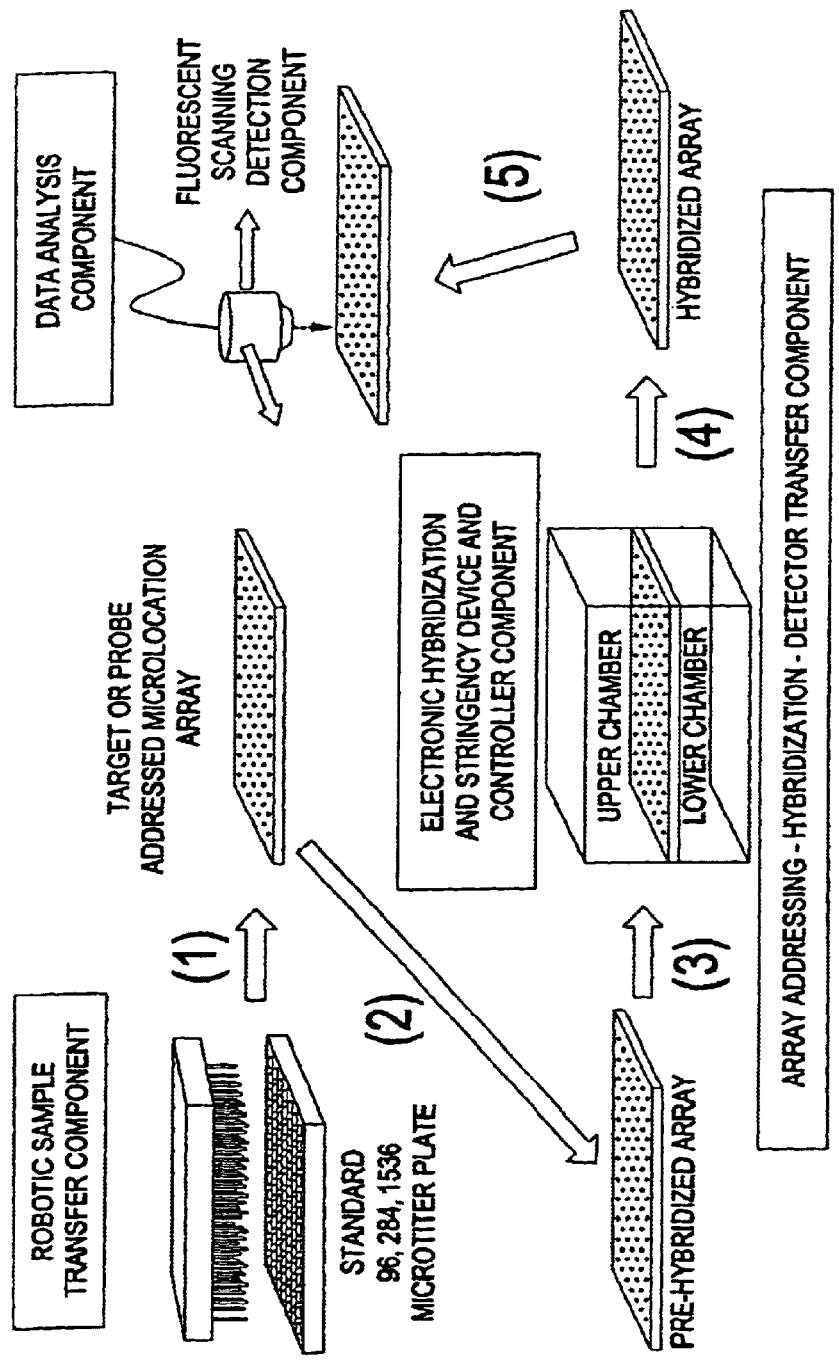
FIG. 6. Flow Diagram of Robotic System Employing the Invention. In this illustration, a simple device of the invention (similar to that pictured in FIG. 100) is loaded from a standard microtiter plate using a commercially available robotic sample handling system an read using a commercially available fluorescent scanning device. As illustrated in this concept system, the devices and methods of the invention may be easily integrated into current automated assay systems FIG. 7. Stabilization of DNA Duplex by a Cationic Amino Acid (Histidine+). The stabilization of duplex DNA by interaction between the negatively charged phosphate backbone of the DNA with the positively charged groups of protonated histidine is shown.
Figure 7:
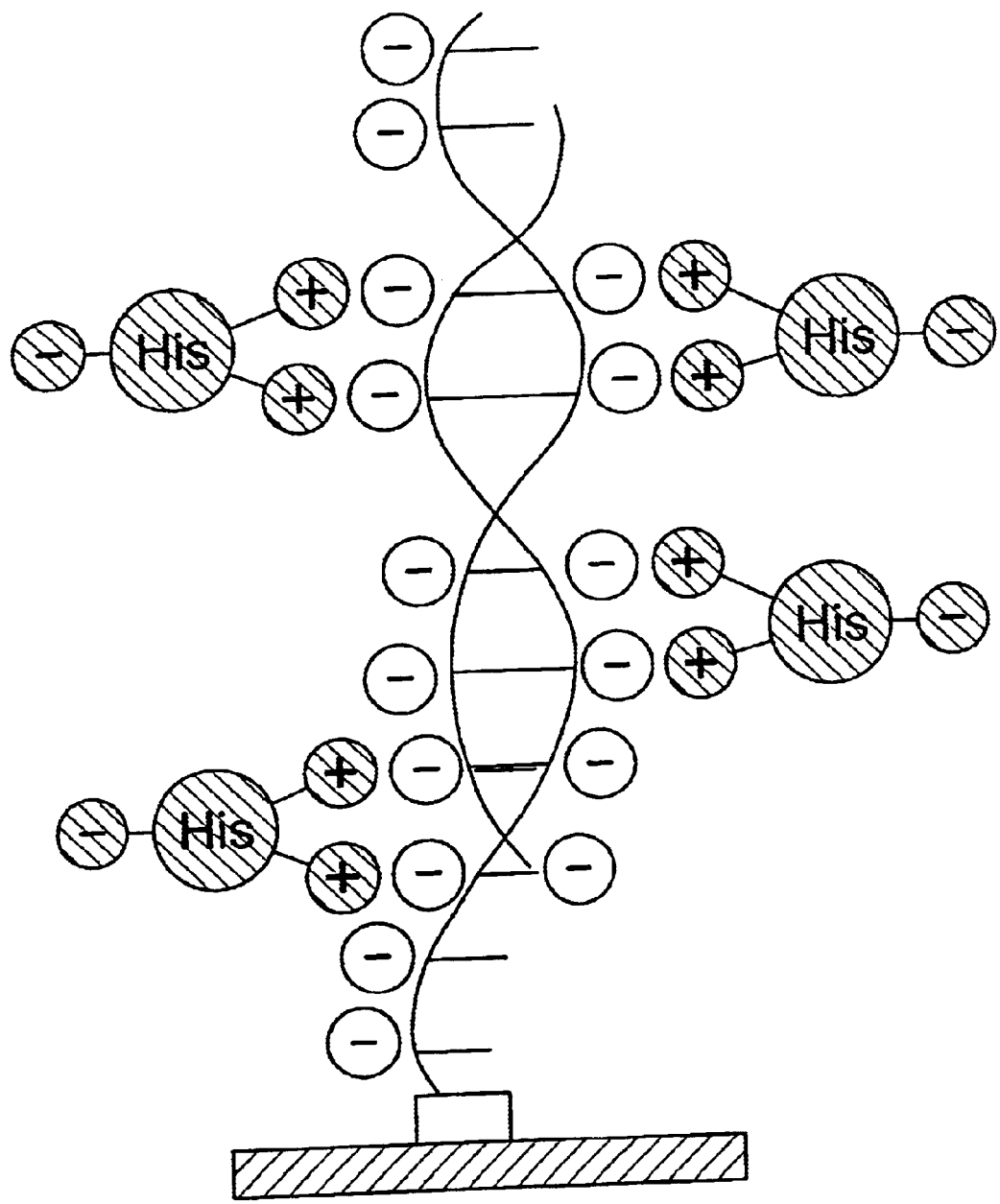

The above descriptions for the design and fabrication of such devices should not be considered as a limit to other variations or forms of the basic device concept. Many variations of the device with larger or smaller numbers of addressable microlocations or combinations of devices can be designed for different analytical and preparative applications. It is also within the scope of this invention to include design of the complete system(s) where robotic sample and liquid handling, control and supporting electronics, detection, and data handling components are included (FIG. 6). Suitable detection techniques include fluorescent scanning or imaging, chemiluminescence, calorimetric, enzymatic, radiometric, electrochemical, and biosensors. The devices and components of this invention can be designed to be compatible with commercially available robotic systems and standard detection or imaging systems. Variations of the device with larger addressable test site macrolocations can be designed for preparative biopolymer synthesis, sample preparation, cell sorting and selection, in-situ hybridization, and as reagent dispensers or waste disposal devices.

After the test site microlocation have been created by using micromachining or other suitable fabrication techniques, chemical modification, polymerization, spin coating, lamination or other fabrication techniques can be used to make the specialized SPM structures, as described below. These important structures effectively impede free or passive diffusion across the test site microlocation by the first and second charged entities in the absence of an electric field.

The spacing between test site microlocations and their size is determined by the ease of fabrication, the requirement for detector resolution between microlocations, the number of microlocations desired on a device, and/or the need to conform to a standard microtiter plate format (96, 384, or 1536 well formats). However, particular spacing between microlocations, or spatial arrangement or geometry of the microlocations is not necessary for device function, in that any combination of microlocations can operate over the complete device area. This aspect of the invention is true whether common first and second buffer reservoirs or a combination of common and individual buffer reservoirs are used. However, the device should be configured such that the electric field is homogeneous at each of the test site microlocations. As outlined below, this can be accomplished with various schemes for individual and/or common electrode placement. When the device is properly configured, free field electrophoretic propulsion provides for the rapid transport and concentration of the first charged entity in the first buffer solution to the test site microlocations, and transport of the second charged entity from the second buffer solution to the test site microlocation reaction zone.

2.2 Choice and Placement of Electrodes for Use in the Devices of the Invention

Any conductive non-soluble material may be used as electrodes in the invention. Metals, such as platinum, gold, palladium, silver, titanium, copper, tin, iridium, aluminum, as well as conductive alloys are suitable. In addition, conducting polymers and conductive non-metals such as carbon may be used. An important consideration is the avoidance of corrosion of the electrode at its surface. Thus, platinum, gold or palladium electrodes are preferred for use in the invention. Alternatively, electrodes which are plated with platinum, gold, or palladium are also preferred for use in the devices of the invention.

The electrodes in the devices of the invention may be placed into the first and second buffer reservoirs, as depicted in FIG. 10, or may be "pins" which are brought into contact with the reservoirs for the purposes of operating the device, as depicted in FIGS. 3, 4 and 5. Alternatively, the electrodes may be formed by wires or printed circuits molded into the buffer reservoir walls or the separating/SPM support structure. If individual electrodes are used for each microlocation, they are preferably so situated in the device, when assembled for use, that the distance between the electrodes is approximately the same for each microlocation. In addition, if individual electrodes are used for each microlocation in combination with common first and second buffer reservoirs, care should be taken so that the electric field for each pair of electrodes mainly passes through the SPM of their individual microlocation. Alternatively, if a common electrode is utilized for all microlocations, either cathode or anode, it preferable that it be so positioned so that the electric field strength is approximately the same at each microlocation.

In a conventional electrophoresis device, either horizontal or vertical, platinum wires are used as the electrodes. The electrodes are placed substantially parallel to the plane of the gel and perpendicular to the electrophoresis direction. Additionally, for DNA separation, the distance between the cathode and sample loading wells is intentionally large so as to provide a uniformed field.

Conventional electrophoresis devices, are essentially two dimensional. The samples are loaded as a 1×n array and the field is generally in the plane of the gel. The devices of the invention can be considered three dimensional because the samples are in a two dimensional array (16 rows by 24 columns to form a 384 site micro-plate) and the electric field is substantially perpendicular to the test site/microlocation sample plate.

In the devices of the invention, field uniformity can be achieved by using plate, wire mesh, screens, or multi-pin electrodes parallel to the two dimensional array sample plate. A gradient. A potentials problem with this design is that gas evolves during electrolysis. Gas bubbles from the electrode may be trapped by the test site microlocation sample plate and can cause changes in impedance, current density and/or field strength. A potential solution would be to provide stirring or mixing to disperse the gas bubbles.

Alternatively, the device could be run vertically such that the gases are allowed to vent. Yet another alternative is to use baffles or barriers to allow electrode placement that provides venting of gases.

The baffles or barriers are constructed from a non-conducting material, such as plastic, rubber or glass. In a horizontal configuration that has upper and lower buffer reservoirs, baffles are only needed for the lower reservoir electrode. The upper reservoir can use a plate or screen electrode that spans all the test site microlocations. The lower reservoir electrodes are placed such that gases evolved during electrophoresis are prevented from becoming trapped on the underside of the test site microlocation sample plate.

2.3 Selection of Semi-permeable Matrix Materials and Construction of the Semipermeable Matrix Semi-permeable matrix materials can include but are not limited to: metal oxides, membranes, agarose, polyacrylamides, hydrogels, sol-gels, aero-gels, fritted glass, porous glass, chromatographic resins, porous silicon, cross linked polymers, and various manmade and natural membrane materials such as nylon, nitrocellulose, cellulose, DEAE, polycarbonate, chitosan, etc. The SPM may comprise a single layer of a single material, a single layer of heterogeneous materials, several layers of the same or similar materials, several layers of different materials.

In SPM's constructed of a single layer of material, the layer may be composed of a uniform material, or a material which has been modified on its surface or within a portion of the material for attachment of the specific binding entity. For instance, an agarose hydrogel containing streptavidin may be used to form the SPM. Alternatively, the surface of a porous glass SPM may be derivatized for the attachment of specific binding entities by known functionalization techniques to provide carboxylic acids, amines, or ester groups. In addition, SPM's containing a single layer of material may be formulated from aggregate materials (e.g., chromatography resins suspended in an agarose hydrogel).

SPM's may be constructed from several layers in order to combine the properties of several materials to more precisely regulate the permeability of the SPM to the first and second charged entities. Alternatively, the layers may be used to provide additional microenvironments not present at the surface of the SPM. These layers may comprise hydrogel layers, membrane layers, aggregate layers, or any combination of such layers necessary to accomplish particular desired effect on the mobility of the first and second charged entities. For instance, a membrane layer in of the SPM may contain pores of a size which will substantially impede the diffusion of the first charged entity. Membranes with pore limits which are slightly greater than the radius of gyration of the first charged entity are preferred. For DNA applications, membrane pore limit sizes from 1 kD to 10 kD are suitable, most preferably those from 3 kD to 5 kD. Similarly, a SPM may comprise a membrane on the second-buffer side of the SPM whose pore size is chosen to impede the diffusion of the second charged entity through the SPM. Membranes with a pore limit of 1 to 10 nm would be useful to impede metal or other dissociable ion species, e.g. $Li^+$, $Mg+^2$, and $Co+^2$. Membranes with larger pore sizes would be useful to impede larger charged entities, e.g. polyvalent peptides and EDTA. In addition to size-exclusion functions, membranes layers in the SPM may also be utilized to attach the specific binding entities.

In addition to membrane layers and hydrogel layers, the SPM may also comprise one or more sedimentation layers comprising a relatively loose material. A sedimentation layer may comprise any suitable sedimentary material, including metallic microspheres, silica, chromatography resins, and polymer microspheres. These sedimentation layers may be held in place in the SPM by being "sandwiched" between other SPM material layers. For example, a chromatography resin may be sandwiched between two polycarbonate membrane layers in an SPM. Alternatively, a sedimentation layer may be bounded only on one side by another SPM layer, and may simply be held in place by gravitational forces. For instance, a layer of metallic microspheres to which a specific binding entity is attached may be deposited by centrifugation over an agarose hydrogel layer. This layer would be held in place by gravity during operation in a horizontal device, such as that pictured in FIG. 10.

SPM's may also comprise a partially insulatory layer which further restricts the electric field within the microlocation. These discontinuous insulatory layers may be fabricated from any solid or viscous insulatory material, e.g. plastic or lipid-like materials. Viscous lipid emulsions may be used, for instance, to add further resistance to the motility of the second charged entity through the SPM. If fashioned from a rigid material, an insulatory layer will preferably be at a surface of the SPM and contain one or more perforations in the layer to allow the passage of charged entities through the SPM. Thus, in these embodiments, the actual conductive surface of the SPM is limited to the conductive surface exposed by the perforations in the insulatory layer. This may assist in further concentrating a first charged entity analyte for detection. In addition, different specific binding entity species may be mechanically deposited at individual perforations in a test site's SPM, allowing for simultaneous detection of specific binding of several species of first charged entity to several species of specific binding entity.

SPM'say comprise a layer of material whose purpose is to regulate the passage of charged molecules based on an exterior, controllable factor. Such gating materials may function according to several mechanisms, including electro-(chemo)-mechanical, electrochemical, and magnetic actuation mechanisms. In electro-(chemo)-mechanical materials, and electric field causes the physical opening and closing of microscale valves. This can be done by pure electromechanics or by a doping/undoping mechanism of a conducting polymer (0.5–2.5 V activation) which leads to swelling or shrinking of the polymer. These materials are somewhat restricted in terms of solvent, present ions and switching speed and stability. In pure electrochemical materials, shrinking and swelling of the polymer in combination with control over surface charge can be used to change the permeability of all species or only charged species. In addition, such mechanisms may be used to change the "wettability" of polymers and surfaces. Electrochemical control over surface charge is not limited to polymers, but is also applicable to any kind of conducting surface.(e.g., M. Nishizawa, V. P. Menon, C. R. Martin Science 268, 700 (1995), in this paper a gold plated aluminum oxide membrane was used to control ion transport by applying +/–0.6 V). Liquid crystal polymers or membranes derivatized with liquid crystal polymer could also be used to change permeability. In magnetic actuation, magnetic beads (large) or polymers loaded with magnetic beads (small) or particles at the bottom of the well are utilized to "gate" the pores of a membrane. Control circuitry for these types of electrically activated materials may be easily incorporated into the semipermeable matrix's support by methods well known in the printed circuit arts.

At least a portion of the semipermeable matrices used in the devices of the invention contains attachment moieties to provides a base for the covalent or non-covalent binding of the specific binding entities. The thickness of this portion of the SPM can range from a nanometer to the entirety of the SPM. In the former cases, the SPM may be chemically modified In the later cases, the SPM can be formed a single material. Certain SPM materials which can be further activated for the coupling of binding entities are included within the scope of this invention. The specific binding entities are covalently or affinity coupled to the attachment moiety containing portion of the SPM. For example, streptavidin can be incorporated into the SPM, providing an affinity binding site for DNA probes which have been derivatized with biotin. Usually, the specific binding entity forms a mono-layer of the specific binding molecules at the first-buffer surface of the SPM. However, in some cases the binding entity layer can have several or even many layers of binding molecules. A common example would be the use of multiple DNA hybridization to create a "sandwiched" structure. Alternatively, the specific binding entity can be attached throughout a portion or the entirety of the SPM, or attached to a portion of the SPM which is adjacent to the second buffer side of the SPM.

Optimally, the portion of the SPM which has been modified for attachment has a very high density of functionalized locations per square micron ($\mu m^2$) for the attachment of specific binding entities. The attached specific binding entity should practically cover the entire surface of the SPM so as to ensure interaction with the first charged entity upon concentration of the first charged entity in the reaction zone. This is especially important when the invention is utilized in diagnostic applications where the analyte is present in very low concentrations in the first buffer reservoir. Conversely, the layer of specific binding entities should not be so dense as to prevent the migration of the second charged entity across the SPM.

3.0. Applications and Uses of the Devices of the Invention

3.1. General Uses and Considerations

In most reactions performed in the devices of the invention, two criteria apply: a) the necessity for movement of materials, reactants, components, etc. to a reaction zone; and, b) within the reaction zone, the presence of an environment conducive to the desired reaction, i.e. the presence of other reagents, binding agents, catalysts, or other such species within the reaction zone at levels sufficient to facilitate the desired reaction. This invention is unique in that it employs electric fields to transport charged entities rapidly and efficiently to the reaction zone, and rapidly concentrate them within the reaction zone. Specifically, low conductivity buffers are used to facilitate electrophoretic transport of charged entities from the first buffer chamber to the reaction zone (to awaiting specific binding entities) while charged entities present in the second buffer chamber (that will aid and support the desired reaction) enter the reaction zone from the other side of the SPM, also moved and concentrated by the same electrophoretic force.

In general, once a device has been addressed with specific binding entities on or within the SPM test site microlocations, a variety of molecular biology type multi-step and multiplex reactions and analyses can be carried out using this electric field controlled two chamber device. The devices of this invention are able to electronically provide active and dynamic control over a number of important reaction parameters. This electronic control leads to new physical mechanisms for controlling reactions, and significant improvements in reaction times, specificities, and sensitivities. The improvements in these parameters come from the ability of the device to electronically control and directly affect: (1) the rapid transport of reactants or analytes to a specific microlocation reaction zone containing attached specific binding entities; (2) an increase in reaction rate due to the concentration of reactants or analytes with the specific binding entities on or within the specific test site microlocation; (3) the rapid and selective removal of un-reacted and non-specifically bound components from the test site microlocation; and (4) the stringency for optimal binding conditions.

The devices of this invention are able to rapidly carry out a variety of micro-formatted multi-step and/or multiplex reactions and procedures; which include, but are not limited to:

DNA and RNA hybridizations procedures and analysis in conventional formats; e.g., attached target DNA/probe DNA, attached probe DNA/target DNA, attached capture DNA/target DNA/probe DNA;

multiple or multiplexed hybridization reactions in both serial and parallel fashion;

restriction fragment and general DNA/RNA fragment size analysis; STR analysis; SNP analysis;

molecular biology reactions, e.g., restriction enzyme reactions and analysis, ligase reactions, kinase reactions, and DNA/RNA amplification;

antibody/antigen reactions involving large or small antigens and haptens;

diagnostic assays, e.g., hybridization analysis (including in-situ hybridization), gene analysis, DNA fingerprinting, forensic applications and immunodiagnostics;

sample preparation, cell storing, selection, and analysis; gene expression analysis;

biomolecular conjugation procedures (i.e. the covalent and non-covalent labeling of nucleic acids, enzymes, proteins, or antibodies with reporter group, including fluorescent, chemiluminescent, colorimetric, and radioisotopic labels);

biopolymer synthesis, e.g., combinatorial synthesis of oligonucleotides or peptides;

water soluble synthetic polymer synthesis, e.g., carbohydrates or linear polyacrylates; and macromolecular and nanostructure (nanometer size particles and structures) synthesis and fabrication.

3.2. Nucleic Acid Hybridization 3.2.1 General Aspects of Nucleic Acid Hybridization Nucleic acid hybridizations are an important embodiment of the methods of the invention because of their importance in diagnostics, and because hybridization reactions characterize one of the more difficult types of binding (affinity) reactions. The devices and methods allow nucleic acid hybridization to be carried out in a variety of conventional formats (e.g., "dot blot" hybridization and "sandwich" hybridization , as well as novel formats. The ability of the devices of the invention to electronically control and accelerate reaction parameters greatly improves nucleic acid hybridization analysis, particularly the ability of the devices to provide electronic stringency control (ESC) to the test site microlocations.

The term "nucleic acid hybridization" is meant to include hybridization reactions between all natural and synthetic forms and derivatives of nucleic acids, including: deoxyribonucleic acid (DNA), ribonucleic acid (RNA), polynucleotides and oligonucleotides, peptide nucleic acid; etc. These hybridization reactions may be performed by themselves, as in sandwich hybridization detection methods, or as part of a multi-step process, as in the SDA amplification reactions of Example 7.

For the purposes of illustration, a device for DNA hybridization analysis may be designed, fabricated, and used in the following manner:

A support structure for SPM microlocations, e.g. a plate comprised of an array of holes which, for the purpose of this example, may be considered to be 1 to 2 mm diameter and 3 to 5 mm deep but, in other embodiments, may have different dimensions, is fabricated from plastic, ceramic or other such previously described insulatory materials using standard molding or micromachining techniques. The structure itself may have additional elements, e.g., waveguides, control circuits, biosensors, magnetic sensors, optical sensors, temperature and pH sensors, cantilevers, microsensors, etc., located near or within the SPM or reaction zone of each microlocation. These sensors might be employed to provide feedback control of the test site reaction zone microlocation operating environment (e.g. voltage or current regulation), or, alternatively, these sensors might be employed detect specifically targeted and/or hybridized entities, reactant levels, or reaction products (bound or free) in or around the reaction zone. The individual test sites microlocations for the SPM may have an enlargement, indentation, or beveling on the first buffer side such that when SPM material is deposited or cast within the hole, a portion of the hole on the first buffer side remains unfilled, thereby creating a small well or depression into which sample material may be deposited or loaded (FIG. 8). The number of addressable microlocations fabricated on an array depends on the final use. However, it is desirable that the microlocations be of such number and spacing so as to be compatible with standard microtiter plate (e.g., 96 well, 384 well or 1536 well) dimensions. These embodiment of the invention allow the improved reactions of the devices and methods of the invention to be performed with standard, readily available, robotic or highly integrated dispensing devices. The use of such automated sample handling devices eases sample loading, fluid/reagent delivery and general overall handling and storage.

Pre-fabricated SPMs such as membranes, filter papers or self-supporting gels are attached to or incorporated into support structures by lamination (heat, adhesives), adhesion, press-fitting or sandwiching. These SPMs can be derivatized or loaded with reactive groups or specific binding moieties before, during or after the attachment or incorporation process. SPMs can also be produced during or after attachment or incorporation into support structures. For example, wells or capillaries within the support structure may be filled or coated with solutions or precursors (particles, beads) that can be polymerized (chemical, thermal, photochemical), gelled (temperature, exposure to other chemicals), melted or sintered to form SPMs. For this purpose, wells or capillaries may be temporarily or permanently terminated with a semipermeable membrane or a simple screen to prevent liquids or precursors from leaking out of the enclosure. An additional advantage of such a geometry is that air that otherwise might get entrapped in the well or capillary can be removed by application of pressure, vacuum or centrifugal force. Yet another advantage of such a geometry is that at least one surface of the SPM is flat and level with the surface of the support structure, which can be desirable to avoid entrapment of air bubbles during filling of buffer reservoirs.

After fabrication, appropriate storage conditions for SPM containing devices need to be considered. Depending on the matrix and matrix loading (e.g. reactive groups, specific binding entities) it might be necessary to store SPM containing devices in liquid, in liquids that contain preservatives, under inert or controlled atmosphere, in the dark, or at low temperatures. The desired shelf-life of the SPM and compatibility of storage conditions with the use and loading of the matrices in the devices and methods of the invention are also important considerations. In general, care should be taken to avoid excessive exposure to acid, base or organic and inorganic chemicals that might alter or damage SPMs before, during or after the application of electric fields. It should be noted that the application of electric fields usually generates resistive heat that could alter or damage SPMs, and that these thermal effects should be considered when choosing the electric field parameters.

The attachment or association of specific binding entities on or within the SPM can be accomplished in either covalent or non-covalent fashion by incorporating or activating reactive entities on or within the SPM and/or the specific binding entities. Suitable reactive entities for covalent attachment are amines, alcohols or carboxylates that react with N-hydroxysuccinimidyl-esters (NHS) and other activated esters, epoxides, anhydrides, carbonates, isocyanates, acyl-azides, aryl-fluorides, aldehydes (followed by reduction), or sulfonyl-chlorides. Other reactive entities are thiols that react with bromo- or iodoacetyls, maleimides or other activated multiple bonds. Further covalent attachment reactions are initiated by UV light exposure as part of a polymerization or grafting process. One skilled in the art would be able to readily synthesize such materials from commercially available chemicals. For example, a glass based SPM could be easily modified with specific binding entities such as DNA oligonucleotides. The SPM would be first coated with amine-terminated silanes (e.g., 3-aminopropyltriethoxy-silane), followed by reaction wit carboxyl-derivatized DNA oligonucleotides (custom synthesized) in presence of a common coupling agent such as EDC (1-(3-dimethylaminopropyl)-3-ethylcarbodiimide hydrochloride).

Specific non-covalent attachment is preferably achieved by a substrate-protein interaction between biotin and streptavidin (avidin). For example, a polyacrylamide based SPM could be loaded with streptavidin (commercially available) and then incubated with biotinylated DNA oligonucleotides (custom synthesized or PCR product). The streptavidin-polyacrylamide would be obtained by co-polymerization of acrylamide/bis-acrylamide with streptavidin and acrylic acid N-hydroxysuccinimidyl ester. Other biological systems include antibody/antigen interactions. A synthetic alternative is the non-covalent binding of phenylboronic acid to salicylhydroxamic acid (Prolinx® system). Simple electrostatic or Van der Waals interactions are also useful for attachment of specific binding entities to SPMs.

Specific binding entities and the respective reactive entities for their attachment are either an integral part of the SPM or are attached to the SPM in additional steps. First charged entities are preferably introduced in additional steps. Identical or a number of non-identical specific binding entities and reactive entities can be located throughout, at either side, at both sides, in the interior, or across the exposed surface of a SPM. The desired distribution and density is tailored for the particular reaction by chemical, structural, photochemical, photolithographic, mechanical or fluidic means.

Following addition of the SPM to the support structure, the device itself may then be assembled by clamping or otherwise fixing the SPM with its support structure between the first and second buffer chambers, as illustrated in FIG. 10. In a vertical embodiment of the device, the support structure with SPM maybe inserted into a groove present in open tube or trough whereby, after the support structure with SPM has been inserted, two chambers are thereby created on either side of the support structure. A further embodiment of this process would be a series of support structures set into grooves, holders or other suitable frames to construct a series of chambers segregated by support structures with SPMs.

In another possible assembly, one or several capillary tubes filled with SPM or other sets of individual SPM containing support structures are placed or mounted between the first and second buffer chambers. In yet another version of the device, the support structure comprises an assembly of having both the support structure and one or more integral buffer chambers. This assembly is placed into second chamber or reservoir such that contact between the two chambers or reservoirs is mediated by the SPM. The support structure assembly can then be physically moved from between a variety of second buffer chambers, as needed, thereby facilitating the process of buffer exchange, washing, etc. Variations of this would include devices and systems whereby only a support structure with SPM was moved between chambers.

Figure 14:
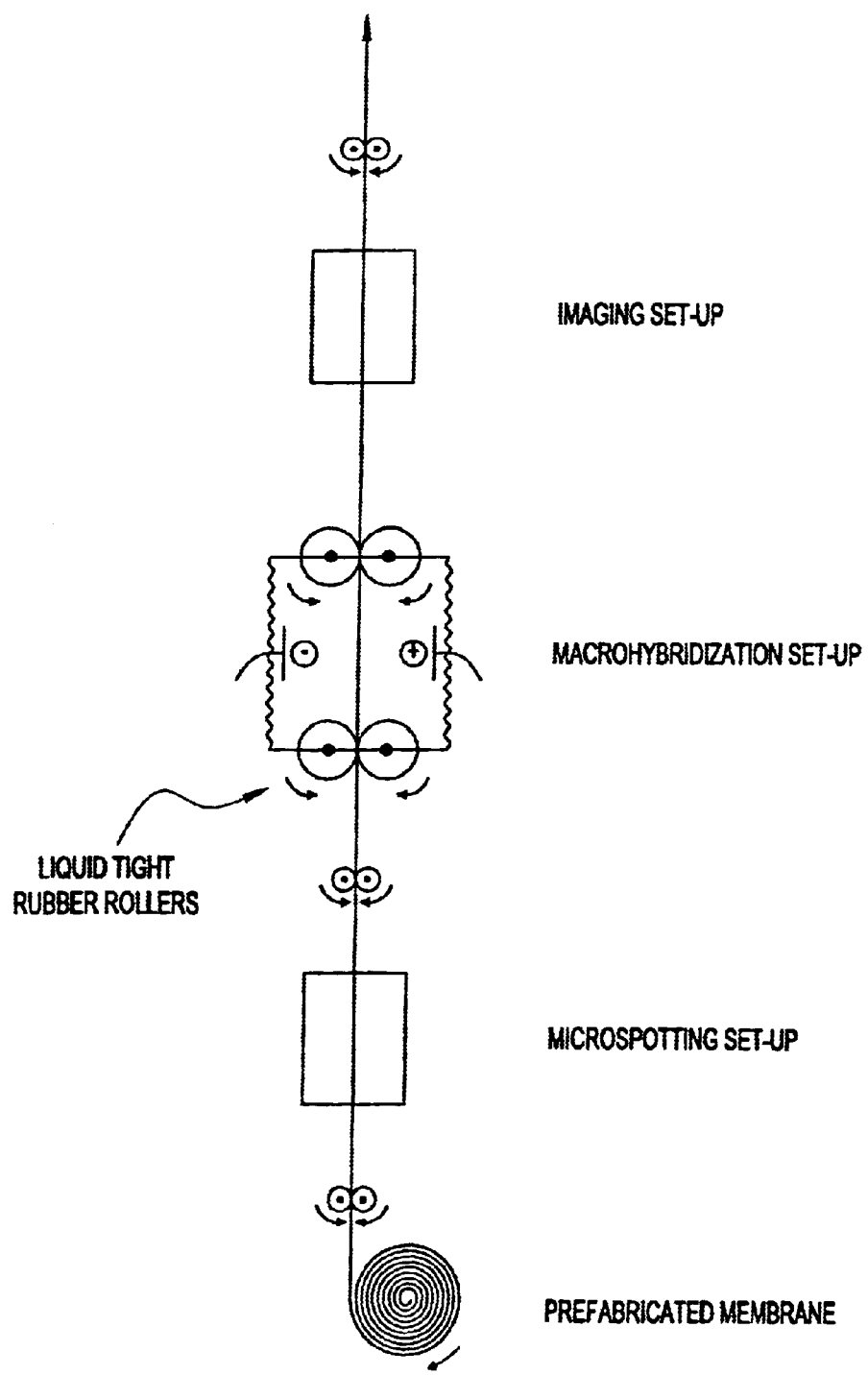
FIG. 14: "Rolling Mill" Embodiment of the Device of the Invention. The devices of the invention may be formatted for continuous feed processing, such as in this "rolling mill" schematic. A contiguous strip or sheet of membrane with test site microlocations on it may be fed through a system in a continuous or semi-continuous manner. The microlocations may be defined by a plastic laminate layer with holes at defined intervals. A microspotting set-up then applies a specific binding entity and labeled sample (first charged entity). The membrane SPM's may then be fed through a dual-chambered set-up defining the first and second buffer chambers, which may be constantly or intermittently supplied with fresh buffer. After hybridization and electronic stringency, the membrane SPM may then be fed into an imaging set-up for detection of the bound sample.

As another embodiment of the device and method of the invention, the support structure is fed into a "rolling mill" continuous feed device. In these embodiments, an extended sheet forms the support structure/SPM between the two components of the "rolling mill" apparatus (also supporting the SPM), creating a separation within a larger chamber to form the two necessary separate chambers. SPMs made of membrane or modified membrane materials are especially suited to this embodiment of the method. The specific binding entity and first charged entity may be "spotted" onto the extended sheet prior its introduction into the rolling mill, and then hybridization performed as described below after the introduction of the SPM into the rolling mill in order to create microlocation between the two chambers. An illustration of this embodiment is provided in FIG. 14.

Present within these first and second chambers of these various device assemblies are electrodes comprised of platinum (or other electrically conductive material as described earlier). These electrodes are so fabricated as to be either permanently mounted within their respective chamber, or are mounted or placed in a removable fashion within their respective chambers so that the electrodes can be present within the device as needed.

Buffers of suitable composition are then introduced into the respective chambers. For the purposes of this specific example, the first buffer chamber might receive a buffer of low conductivity (e.g. 50 mM histidine at its pI) while the second buffer chamber might receive a buffer composed of with a higher percentage of net positively charged species (e.g., 50 mM histidine adjusted to pH 5.5). In embodiments wherein the first and second chambers are in a vertical or stacked configuration with either the lower or upper chamber serving as the first buffer chamber, i.e. the SPM support forms a horizontal layer between the two chambers (as in FIG. 10), care must be taken to ensure that air and evolved gas bubbles are not entrapped between the lower chamber and the bottom of the SPM support. One method found to efficiently prevent or minimize this phenomenon is to construct the lower chamber in such a fashion that the level of buffer in this chamber is higher than the SPM support (see FIG. 10). By tilting the apparatus during filling with buffer, air bubbles are released from the chamber, resulting in a contiguous liquid layer being present between the buffer chamber and the support system upon setting the device back to the horizontal.

Alternatively, wicking layers may be added to the SPM support on this lower side to aid in providing contiguous electric contact between the lower chamber, the SPM and the upper chamber. In a further possible embodiment, the device might be so constructed that a permanent or fixed angle (i.e. non-horizontal) aspect is given to the arrangement of the support as situated in the lower chamber such that air bubbles freely migrate out past the SPM support and out through suitable openings within the device. Or, the SPM support plus upper chamber might be placed into a larger lower chamber at angle then set horizontally once all entrapped air is released.

In other embodiments of the device, channels or grooves might be made in the lower aspect of the support structure facing the lower chamber such that bubbles are moved away from SPM microlocations. Alternatively, the support structure might be designed and fabricated with an angular character. Such angles may be fabricated on the support structure or formed upon insertion of the support structure between the two chambers in order to prevent air entrapment (e.g., forming an angular or V shaped bottom rather than a flat bottom). In further embodiments, the surface of the support structure might be modified either chemically or physically to lower surface tension and increase wettability. Any combination of these mothods plus othr, related approaches may be employed to minimize air entrapment during assembly of the device.

The introduction or loading of the various entities (specific binding entities, their respective reactive entities for attachment, and the first charged entities) onto the microlocation is performed by liquid (solutions, mixtures, suspensions, pure materials) or vapor (mixtures or pure materials) exposure. Liquid exposure includes, e.g., spotting or microspotting onto the SPM in the absence of buffer, volume exposure (introduction of liquid to the device or dipping of the device in liquid), or local dispensing of small aliquots (solutions, suspensions or pure materials) into water, buffer or solvent. Localized dispensing of small aliquots onto the STM may be aided by addition of agents that change viscosity or density of the solutions or suspensions to be dispensed (e.g., 6% glycerol, sucrose or ficol). This approach is akin to the method commonly employed in standard polyacrylamide gel electrophoresis (PAGE) experiments for sample introduction. Liquid application of entities can be performed in presence (hot load) or in absence of an electric field, light (photolithography), convection, or pressure or vacuum induced flow. Dispensing of liquids may be performed in a manual fashion (pipette, syringe) or by an automated or semi-automated system in a serial or parallel process. Vapor exposure, most suitable for reactive attachment reagents, may be performed in presence or in absence of light (photolithography), convection, pressure or vacuum induced flow.

Another method for dispensing binding entities to each microlocation is to transport specific binding entities such as specific oligonucleotides from a separate electronic reagent supply device. This supply device would hold a large quantity of binding entities or reagents for loading the test site microlocations. Using the controlled application of electric fields, specific binding entities or first charged entities may be electronically transported between the two devices. This system eliminates the need for physical manipulations, such as micro-pipetting, and for complicated fluidic delivery systems within or between devices.

The specific binding entity, first charged entity, and second charged entity may represent single species, forms, or classes (e.g., all of the specific binding entity or all of the first charged entity is a group of oligonucleotides having the same sequence). Alternatively, these entities may consist of a plurality of molecular species. Such would be the case if the first charged entity comprised two or more oligonucleotides composed of different sequences or if two or more functional groups were utilized as the specific binding entity. Having a plurality of species permits a multiplicity of reactions to occur within the same reaction zone microlocation (e.g., detection of more than one type of oligonucleotide using different wavelength fluorescent reporter oligonucleotides), and also permits "linked" stepwise reactions utilizing multiple species within the same reaction zone microlocation.

Relative electrophoretic transport rates of multiple species comprising a charged entity will reflect the mobility of each species in the electric field as well as other possible influences (e.g., interactions with buffer, etc.) such that different species might be staggered or ranked in their movement and accumulation in the reaction zone at the microlocation. Under certain circumstances, the ability to effectively "layer" species in such a fashion may provide a novel mechanism whereby a gradient of charged entities (either number or type) may be formed within the reaction zone using electric fields (e.g., by isoelectric focusing). Alternatively, the electric field may be used to time their relative arrivals at the reaction zone.

It should also be noted that the specific binding entities need not be permanently fixed within the SPM. That is, the specific binding entities may be separable from the support matrix such that they may be subsequently released (as well as any bound charged entity) upon completion of the reaction. An example of this is where the binding entities are anchored by labile linkages (either covalent or non-covalent) to the semi-permeable matrix (e.g., an ester linkage, or even a portion of DNA sequence containing a restriction endonuclease recognition site). Upon completion of the desired reaction(s), the binding entities (along with the bound product of the reaction) might be released by cleavage of the labile linkages using either enzymatic, photochemical, pH change, altered salt concentration, solvents, etc., or by other means into the first buffer chamber. Alternatively, the binding entities may be present as surface modifications on larger objects or structures such as microspheres. The microspheres may be present within a labile matrix which upon the completion of the reaction would be dissolved either enzyimatically, with altered pH, change in solvent, change in temperature, or by other means. The microspheres, along with the bound entities, would then be available for subsequent manipulation, on or off of the device.

A variation of having a removable or exchangeable reaction zone microlocation is an embodiment in which the SPM comprises magnetic or paramagnetic devices or microspheres having surface modifications suitable for anchoring binding entities. The SPM is held in place by use of gravity or magnetic forces (arising from either the support structure or external to the device). Upon cessation of the applied magnetic field, the magnetic devices or microspheres may then be removed and/or moved to another microlocation by either physical, fluidic, magnetic or other means, along with any bound or hybridized materials, after the reaction. Additional multiplexing can be achieved if a mixture of magnetic devices or microspheres, each with a unique specific binding entity, is present at the microlocation.

Alternatively, a SPM microlocation might be transiently formed from an aggregate of species electrophoretically transported and concentrated at the microlocation whereby, at the cessation of the applied electric field, the aggregate would dissociate back into its component elements. Such would be the case if the SPM were comprised from colloidal or related lipid-like materials concentrated in the reaction zone under the influence of the applied electric field.

A consideration when using the devices of the invention is osmotic pressure set up by the imbalance of ions on either side of the SPM in partitioned systems. The structure of the SPM should be constructed in such a fashion as to maintain the integrity of the SPM in those instances where the imbalance is great. Methods to accomplish this include the use of bonding agents to fix the SPM into the support system, "stiffeners" or specialty polymers to add structural support within the SPM, and/or timing events such that SPM breakdown does not occur within the time period necessary to achieve the desired reaction.

Having assembled the device with appropriate buffers and binding entities, an electrical current is passed through the device utilizing the electrodes present in the first and second chambers. The electronic control of the interaction between binding entities within the reaction zone is accomplished in a variety of fashions, dependent upon the designs features of the overall device, the nature of the entities reacting with each other and the overall purpose of the reactions. In one embodiment, a serial system of voltage application (either by individual site or by row) provides the means to explore a variety of reaction conditions on one plate. This would be a desirable feature to rapidly and efficiently determine optimal condition for operating particular devices of the invention, since the geometry of test site microlocation (both in terms of its particular shape and size and its relationship to the respective chambers and electrodes shape, size and spatial configuration), buffer volume, concentration & viscosity, binding entity concentration and binding affinities, SPM depth, porosity & form (e.g., hydrogels vs. sol gels), temperature, etc., are variables interrelated in their effect upon the reaction zone and thus affect the desired reaction. Therefore, serial methods for determining electric field conditions might be the most efficient route for determining optimal system operating parameters (including applied voltage, form of applied electric field, time of application, etc.)

Operational voltages for the devices of this invention are expected to range from approximately 1V up to 1000V. Governing factors for voltage selection include but are not limited to: device size and geometry; buffer conductance; mobility of the charged entities in the applied electric field; resistivity of the SPM; and assay requirements, e.g., targeting of the binding entity vs. hybridization of the first charged entity vs. electronic stringency. Device size and geometry plays a role in the following fashion, distances that the first binding entity must traverse in small first buffer chambers (e.g. on the scale of millimeters to a few centimeters) are necessarily shorter than those in larger first chambers, e.g. centimeters to tens of centimeters. Very small devices may achieve reasonably rapid concentration of the charged entities with voltages ranging from 1V to 5V. In order to achieve effective concentration of the first binding entity at the test site in larger chambers in the same time period as in smaller devices, more electromotive force needs to be applied, therefore higher voltages are utilized. In moderately sized devices, e.g., FIG. 10, voltages ranging from 2V to 100V have proved useful.

Likewise, the resistivity of the SPM and the conductance of the buffer influence the voltage drop across the device as well as the net electromotive force on the charged entities. In order to achieve within the same device the same degree of effective concentration of charged entities, the applied potential should account for any differences in conductivity of the buffer or SPM as described earlier.

The nature of the reaction or assay step also influences the range of voltages applied. That is, in targeting binding entities to the SPM, a few volts have proved adequate in the moderately sized devices. Likewise, for hybridization, 5V to 20V have proved adequate to achieve hybridization between the binding entity (e.g., DNA) to the first charged entity (e.g., DNA) as mediated by the second charged entity (e.g., histidine having a net positive charge). In contrast, under these conditions, electronic stringency has proved more successful with higher potentials (e.g., five to tenfold higher). Voltages necessary for electronic stringency are also affected by additional considerations, e.g., temperature, buffer composition and concentration, etc. and therefore should not be considered as absolute guidelines. Thus, in a moderately sized device, such as is shown in FIG. 10, voltage ranges of 2V to 100V have proved useful. In considerably larger devices, it is expected that higher voltages, e.g. up to 1000V might be employed for efficient use of the device whereas in smaller devices, such as would be incorporated into laboratory-on-a-chip devices, voltages between 1V to 50V would be expected to be adequate.

Control of electric field application can be accomplished in a variety of fashions. As means of varying the system, the basic structures of the individual chambers, FIGS. 3, 4 and 5), can be further modified by use of either a variety of geometries of the chambers themselves, test site microlocations and electrodes and/or by having individual control of the applied electric field, either by control circuitry built into the SPM support system or the use of additional control circuitry not present on the device. One embodiment would be to have circuitry built into the electrode system for individual chambered electrodes such that a different potential or current would simultaneously be experienced by each. Alternatively, gating materials having high resistivity or which are insulatory in nature may be incorporated into the SPM support system at each test site microlocation to control the initiation and progress of the reaction. A simple embodiment of this would be a mechanical barrier controlled by external circuitry. An embodiment with this technology would be to employ a layer of electroactive polymer whose porosity is affected by an applied voltage (from control elements in the SPM support system) either increasing or decreasing the polymer's permeability to charged entities and therefore serving as a regulatory element of either the electric field or of the movement of various sized charged entities into the reaction zone.

As will be recognized by those of skill in the art, the application of current through the resistive SPM will cause some degree of heating due to joule heating effects. Although slight heating may be desirable to elevate the temperature of the reaction to further accelerate the reactions or to provide thermal stringency for DNA hybridizations, such joule heating can also cause detrimental effects to the first and second charged entities and/or specific binding entity. Thus, the temperature of the reaction zone at the test site microlocations may be regulated by any conventional means, such as heating or cooling the buffer reservoirs, or the entire device, in order to maintain a desired temperature at the reaction zone.

In certain small dimension devices, electro-osmotic flow (EOF) may occur upon the application of the electric field. This surface phenomenon may not be a factor in lager, e.g., multi-millimeter scale devices, however, if devices are constructed which exhibit this property and it is undesirable, then surface treatments to neutralize the zeta potential or charge of the surfaces may be employed to lessen or eliminate electro-osmotic fluid movement. The time course of the desired reaction may also be rapid enough to be only minimally impacted by this EOF phenomenon.

The electronic control of the hybridization process significantly improves the subsequent detection of the target DNA molecules by enhancing the overall hybridization efficiency and by removing non-specific DNA from the, microlocation areas. As few as 10,000 to 100,000 copies of target sequences in un-amplified genomic DNA or mRNA in a sample may be detectable using the devices and methods of the invention. Hybridization reactions of this type can be carried out in a several minutes or less under isothermal conditions well below the Tm of the probes; and with minimal outside manipulations (i.e., conventional washing steps are reduced and in some cases are completely eliminated).

Thus, because of the high efficiencies allowed by the use of the devices and methods of the invention, one may expect to achieve modulations of DNA hybridizations and other reactions of at least 10 fold. Using the devices of the invention with low-concentration analytes, accelerations of DNA hybridization reactions of at least 50, 100, 200, 500, and even over 1000 fold over passive hybridization techniques. For instance, the DNA hybridization in Example 5 using the devices and methods of the invention achieved the same level of hybridization signal in 1/1900 the time necessary when using traditional passive hybridization techniques in high salt buffers. As is evident from this example, the most dramatic acceleration of biological reactions using the devices of the invention will be achieved in low-concentration applications, such as the analysis of patient biological samples in clinical settings. However, the ability to electronically control the inhibition or acceleration of other reactions to a more modest extent (10 or 50 fold) will still be extremely useful in other industrial biochemical and chemical settings.

Stringency refers to increased binding specificity and can be applied during the binding event as well as afterwards. Overall stringency can be increased by traditional means such as raising the temperature, lowering the ionic strength, adding chaotropes, denaturants or co-solvents, or by increasing or changing the bias of the voltage. For example, the addition of a positively charged chaotrope such as guanidinium chloride, in the lower buffer reservoir can reduce nonspecific background as well as increase hybridization stringency. The guanidinium cation and the histidine cation both migrate to the reaction zone. The histidine enables, hybridization while the guanidinium increases the stringency. However, it isn't a requirement that the species be charged in order to raise the system stringency. Solvents, such as alcohols, formamide, can raise the system stringency without being actively transported and concentrated in the reaction zone. Similarly, the presence of nonionic detergents in the buffer reservoir(s) during electronic hybridization may decrease the amount of nonspecific background binding.

Hybridization stringency can be achieved by the conventional parameters of temperature, buffer, salt concentration, and pH and the new parameter of electric field. An important aspect of the disclosed devices is the ability to perform "electronic stringency" by regulating the electric field. Stringency control is especially useful for hybridization specificity, and is particularly important for resolving one base mis-matches in point mutations, as described in Example 3. Electronic stringency control can also be applied to multiple-base mis-match analysis. Perfectly matched DNA hybrids are slightly more stable than mis-matched DNA hybrids. By biasing the microlocations negative (i.e. having a negative bias in the lower or second chamber) and delivering a defined amount of electrophoretic power for a given time, it is possible to denature or remove the mismatched DNA hybrids while retaining the perfectly matched DNA hybrids. (Given the presence of buffer chambers on either side of the SPM, an enhanced positive bias will accomplish the same end). The devices of the invention are capable of providing high hybridization specificity via electronic stringency control. By delivering a defined amount of power it is possible to remove nonspecifically bound molecules as well as discriminating between perfectly matched and mismatched hybrid sequences. As discussed earlier, there are many factors than govern the operational current and voltage conditions necessary for electronic bioassays. Generally, stringency is performed in a high conductivity buffer, such as 20 mM sodium phosphate. Higher voltages are therefore required to generate electric field strengths necessary for stringency. However, the application of conventional stringency parameters, such as temperature, can reduce the amount of electronic stringency required because the overall stringency of the system has been increased.

Electronic protocols for stringency can use either current or voltage sourcing and can consist of DC, DC biased AC or pulse (square, sawtooth, step, etc) waveforms. By way of comparison, on planar microelectronic biochips, stringency protocols are generally 600–1200 nA per 80 micron microlocation using a pulse waveform (3–5 Hz, 30–50% duty) for 1–4 minutes in a phosphate buffer. Comparably, similar protocols may be used in the macroscopic devices of this invention, using voltages in the range of 1 to 5 V up to 1000 V, and utilizing appropriate scaling factors. Depending on factors such as temperature and buffer conditions, the voltage applied during electronic stringency may be greater, less, or the same as the voltage applied during the original reaction. Likewise, the time period of the ESC may be the same, less, or greater than that of the reaction itself. For instance, when the first buffer is exchanged after the hybridization reaction for a higher salt buffer, an ESC voltage of 2–5 times that used in the reaction may be applied across the device. However, in some circumstances, and ESC comprising a simple reversal of the bias at the approximate same voltage as the reaction voltage for about the same period of time will also produce significant improvements in specificity.

During ESC the bias is usually reversed and the mismatched hybrids are moved towards the upper buffer reservoir. If similar conditions are used with the same bias, then the mismatched hybrids still experience the same electric fields. They eventually dissociate selectively (as compared to perfect matches), and electrophorese through the remainder of the SPM towards the lower buffer reservoir. Depending on the SPM composition, this may be a lengthier process compared to ESC, and may require higher voltages.

In a further embodiment, the claimed device provides independent stringency control to each specific hybridization reaction occurring on the device. In effect, each hybridization in each reaction zone/test site is an independent reaction. With a conventional or passive array format, it is impossible to achieve optimal stringency for all the hybridization events which are occurring in the same hybridization solution. However, the active array devices of this invention are able to provide different electronic stringency conditions for each hybridization at different microlocations. This attribute overcomes the nearest limitation in conventional matrix or array hybridization formats, sequencing by hybridization (SBH) formats, and other multiplex analyses.

Compared to conventional passive hybridization procedures, the electronic hybridization methods utilizing the devices of the invention show greatly improved hybridization efficiency and a very large discrimination ratios for one base mis-matches. In addition to improving the specificity (i.e., discrimination ratio) and sensitivity for hybridization (such as single point mutations detection), electronic stringency control allows the use of oligonucleotides outside the normal size range in these applications. Oligonucleotide sequences ranging from 8-mer to 21-mer are traditionally considered acceptable for point mutation detection with conventional hybridization procedures. In the current conventional hybridization procedures, which utilize temperature and salt concentration for stringency control, oligonucleotides in the 10-mer 19-mer size range used most frequently. Oligonucleotides shorter than 10-mers have been found to be unacceptable for multiplex hybridizations; and sequences shorter than 8-mers are not even considered for use because of poor hybridization efficiencies. As the sequence length goes beyond a 21-mer, the ability to distinguish the difference in the hybridization signals between the match and mis-match probes is greatly reduced.

However, as the devices of the invention are able to carry out electronic stringency control, both shorter (7-mer and shorter) and longer (22-mer and longer) oligonucleotides may be used with very high discrimination ratios. The use of shorter oligonucleotide sequences (7-mer and less) have advantages for sequencing by hybridization (SBH). Shorter length sequences allow arrays with a smaller number of oligonucleotides (8-mers=65,536, 7-mers=16,384, 6-mers=4,096) to be used for this SBH applications. For instance, an embodiment of the devices of the invention which is compatible with a 1536 well microtiter plate format could be used to do SBH with 6-mers in a 4-plate-per-sequence format, utilizing standard equipment to load the and read the device. The rapidity and specificity of the methods and devices of the invention make high-throughput SBH utilizing macroscopic devices such as these commercially and logistically feasible. The use of longer sequences (22-mer and longer) with electronic stringency control allows more sensitive and selective point mutation analysis to be carried out. The use of longer probes provides higher sensitivity in DNA samples with high complexity, or which include multiple commonly repeated sequences, and also allow higher overall hybridization efficiencies.

Having applied the appropriate electric fields to achieve the desired reactions, it is desirable to evaluate the efficiency of the reaction. In cases of binding reactions involving fluorescent labeled reporter entities, it is possible to use optical detection systems that use epifluorescent-type microscopes, optical fibers or assemblies of optical fibers, laser or non laser based scanning systems, general-purpose fluorescent imagers in combination with cooled charged coupled devices (CCD), intensified charged coupled device (ICCD), microchannel plate detectors, photon counting photomultiplier (PMT), CMOS image sensors or photodiode arrays. The optical components and associated detectors allow for static or dynamic detection of limited or extended ranges of the UV, visible or IR spectrum. Measurable quantities are fluorescence intensity, emission wavelength, fluorescence polarization, multicolor fluorescence ratios, fluorescence resonance energy transfer (FRET) or fluorescence quenching.

In addition to a variety of fluorescent dyes and reporter entities which can be used to label DNA probes, target DNAs, or antibodies, other types of labels or reporter entities can be used. These include chemiluminescent or radioactive labels, non-linear optical (frequency doubler) materials, magnetic materials, nanoparticles, colloids, non-biotin/avidin complexes and various enzyme linked and cell based systems.

Some embodiments of the devices may involve integrating optoelectronic, electronic or magnetic detection elements within the present device. Both optical and direct electronic detection of DNA is possible with these systems. It is contemplated by this invention that some embodiments may also involve sandwiching together a microelectronic detector and on board controller component in the basic device structure. This strategy solves a number of problems related to fabrication techniques, materials compatibilities, and cost effectiveness for making the device or substantial parts of it disposable.

3.2.1 Applications Employing Nucleic Acid Hybridization

For the purposes of illustration, the following series of events might be envisaged for a simple parallel multistep hybridization assay (i.e. a "sandwich" assay) performed on multiple samples:

First, a support system comprising a multisite array of streptavidin-agarose SPM microlocation test sites within wells (described above) is placed between two chambers, the first (upper) containing 50 mM histidine at its pI and a lower chamber (second chamber) containing 50 mM histidine adjusted to pH 5.5 (or 50 mM histidine at its pI for attaching biotinylated capture sequences (specific binding entities) to the SPM). The electrodes in these respective chambers are then attached to a standard electrophoresis power supply. A few microliters (1 $\mu$l to 5 $\mu$l) of a biotinylated capture oligonucleotides solution (100 nM) in a glycerol-containing sample loading buffer are then deposited at each location using a robotic loading system. A potential of approximately 5 V is then applied across the SPM's of the device with a positive bias to the lower (second) chamber for a short period of time (e.g., 30 seconds). The capture oligonucleotides are rapidly moved under the influence of the electric field to the awaiting binding sites. These capture oligonucleotides then bind to the microlocation test sites, and become the specific binding entity attached to the SPM of the sites.

The buffer solution in the first (upper) chamber is then replaced with fresh 50 mM histidine and target oligonucleotide (first binding entity) solutions are then placed at each test site microlocation (as above) or are part of the bulk buffer solution. Again a potential of 5 V is applied across the SPMs with a positive bias at the lower chamber. In this case, the negatively charged target oligonucleotides present in the low conductance buffer are rapidly transported to and concentrated in the reaction zone of the test site microlocations. Concurrently, the positively charged histidine molecules (second binding entity) migrate from the lower chamber across the SPM to the reaction zone. As nucleic acid hybridization does not occur in the low conductance neutral histidine buffer, it is positively charged histidine cations which enable the hybridization of the target oligonucleotides within the reaction zone of the test site microlocation.

After the initial hybridization event, a reverse bias at approximately the same voltage is applied to remove unbound target (first binding entity) oligonucleotides from the test site microlocations. The buffer in both chambers is then replaced with fresh buffer solution. Fluorescently labeled reporter oligonucleotides are then introduced into the upper (first) chamber and the process of electronic hybridization repeated. Again, unbound reporter oligonucleotides are removed by application of a brief reverse bias. The fluorescence labeled bound reporters are then quantified using optical detection systems described previously, with or without a buffer exchange, dependent upon the concentration of unbound reporter in the bulk solution.

One particular application using this approach would be to employ amplicons, or other large DNA fragments, as the first charged entity and utilize electronic stringency to detect point mutations in the amplified sequence. Double-stranded PCR amplicon products, other amplicon products (SDA, etc.), DNA fragments, or RNA fragments may be: (1) diluted directly into a low conductance histidine buffer (1 to 50, or higher dilution), (2) rapid heat denatured, (3) applied (~5 $\mu$l) to a suitable test site microlocation (pre-addressed with capture probe sequences for discrimination), (4) electronically hybridized for 2 minutes, (5) washed, (6) electronically hybridized with a fluorescent reporter probe sequence (optional), (7) subjected to a 30 second electronic stringency step (using the appropriate current level for the particular base mismatch sequence), (8) and then fluorescently detected and the results analyzed (~1 minute).

The time necessary to carry out the entire above process is less than 30 minutes. The fast hybridization rate is due to the unique advantage of electronic hybridization in low conductance buffers like histidine combined with the provision of cations from the second buffer chamber. The rapid base mismatch discrimination is due to the unique advantages of electronic stringency applied utilizing the active devices of the invention. Double-stranded PCR products can be applied to the devices with minimal denaturation, and it is not necessary to isolate single-stranded target sequences. Step (6) is not necessary if the amplicon or fragment is already fluorescently labeled, as can be carried out in a PCR amplification procedure using fluorescent labeled primers. For fully amplified PCR amplicons it is not necessary to de-salt the sample, as the target nucleotides can be diluted directly into the low conductance (histidine) buffer. For lower copy number amplicons or DNA/RNA isolated directly from cells, a de-salting step to lower conductance is optional.

Another common format for oligonucleotide hybridization assay uses target DNAs as the charged binding entity immobilized at the SPM, with specific probes hybridized as the first charged species to these immobilized target DNAs, a.k.a. the "dot blot". In this format either the same target DNAs may be used at multiple test site microlocations, or different target DNAs (e.g. from different patient samples) at specific test sites. In situations where the target DNA is an amplicon, the amplicon may incorporate a moiety for attachment, e.g., biotin, into the amplicon as part of the amplification procedure. An advantage of using low conductivity buffers in the first buffer chamber to which the target DNA is added is that these buffers do not promote re-hybridization of the double stranded entities until these entities encounter the reaction zone containing the stabilizing cations (arriving from the second buffer chamber).

The electronic hybridization methods of the invention can be used to carry out in-situ hybridizations. In-situ represent a fundamentally different hybridization format in that the target DNA (or RNA) is not removed from cells, but detected directly inside them. In-situ hybridization procedures are generally complex and time consuming, and the detection of short target sequences (i.e. single point mutations) is nearly impossible. Electronic controlled in-situ hybridizations can be carried out at test site microlocations which are so constructed to attach cells directly on the surface of the SPM. Rather than extracting DNA from the cells, the cell membrane may be permeabilized (e.g. application of high frequency and high voltage pulses), and the reporter probes (the first charged entity) electronically concentrated in the reaction zone for hybridization with the DNA within the cells (the specific binding entity). Electronic stringency control is used to increase both selectivity and sensitivity by eliminating much of the non-specific binding and improving overall hybridization efficiency.

Alternatively, the devices and methods of the invention also provide a convenient platform for complex sample processing techniques in which cells are captured and lysed, with the subsequent hybridization and analysis of genomic DNA or mRNA. For instance, cells could be lysed in hyper or hypo-tonic solutions, high voltage pulses and/or detergents. The sample can then be addressed to a microlocation in a device that contains a prefilter to eliminate cellular debris which may clog the SPM. Alternatively, for mRNA, a first round of capture onto poly[A] derivatized SPM or beads can be performed. The unbound material is removed or the beads are transferred to another microlocation for further analysis.

The electronically controlled hybridization methods of the invention also provide new mechanisms for detecting DNA hybridization without using a labeled DNA probe. Rather than covalently labeling the first charged entity DNA, a more direct detection of the hybridization process itself with DNA binding dyes such as ethidium bromide and 5YBR Green. These dyes bind to both double-stranded and single-stranded DNA, but with a markedly greater affinity for the double stranded DNA. Typically, these dyes have a net positive charge and are therefore suitable species for inclusion into the second (lower) buffer chamber. Thus, as the DNA is transported by the electric field to the reaction zone from the first chamber, the dye is transported from the second along with cations for hybridization. The dye binds to both hybridized and unhybridized DNA sequences. By continued bias with a buffer exchange in the lower buffer or by reversing the bias, dye molecules bound to un-hybridized single stranded DNA at these microlocations or nonspecifically bound within the SPM are selectively removed. A proper amount of potential can be applied which does not adversely affect the DNA hybrids. The hybridized DNAs with associated dye molecules may then be fluorescently detected using either stand alone or integrated optical systems.

The following list reiterates several important advantages provided by the devices and methods of the invention with regard to various nucleic acid hybridization reactions and analyses:

(1) The rapid transport of dilute target DNA and/or probe DNA sequence to specific microlocation(s) where hybridization is to occur. This process may take place in the range of 5 to 120 seconds.
(2) Concentrating dilute target DNA and/or probe DNA sequences at specific microlocation(s) here hybridization is to occur. The concentrating effect may be well over thousand fold ($>10^3$).
(3) The rapid removal of non-specifically bound target DNA sequences from specific microlocation(s) where hybridization has occurred. This process may take place in the range of 5 to 300 seconds.
(4) Rapid removal of competing complementary target DNA sequences from specific microlocation(s) where hybridization has occurred. This process may take place in the range of 5 to 300 seconds.
(6) The ability to carry out a large number of independent hybridization reactions in a matter of minutes.
(7) The ability to carry out a hybridization process at isothermal conditions well below the Tm of the probes, and with minimal outside manipulations or washing steps.
(8) The use of electronic stringency control (ESC) to remove partially hybridized DNA sequences.
(9) The ability to carry out hybridization analysis of un-amplified genomic target DNA sequences.
(10) The use of ESC to improve the discrimination ratio (i.e., resolution) and sensitivity of single base mis-match hybridizations (point mutations).
(11) The ability to use single point mutation probes that are either shorter (7-mer or less) or longer (22-mer or greater) than those used in conventional hybridization procedures.
(12) The use of ESC to provide individual stringency, control in matrix hybridization.
(13) Improving the detection of hybridization event by removing non-specific background components.
(14) The ability to carry out electronic in-situ hybridization on fixed cells.
(15) The development of a detection method which eliminates the need for using covalently labeled reporter probes or target DNA to detect hybridization.

As will be evident to those of skill in the molecular biological arts, most commonly used nucleic assay formats may be readily adapted for use in the devices and methods of the invention. As the nucleic acid hybridization reaction is typically the limiting step in most procedure times, utilization of the devices of the invention in the hybridization steps necessary for most DNA and RNA detection and manipulations can dramatically decrease the times necessary for these procedures.

For instance, the devices and methods of the invention may be employed to greats advantage in DNA or RNA amplification procedures, such as the strand displacement amplification (SDA) procedure illustrated by Example 7. Any other primer-based amplification procedure, such as the thermal-cycle polymerase chain reaction (PCR) or ligase chain reaction (LCR), can be adapted for use in the device.

3.3 Other Uses and Applications 3.3.1 Combinatorial Biopolymer Synthesis

The devices of this invention are also capable of carrying out combinatorial synthesis of biopolymers such as oligonucleotides and peptides at reaction zone test sites. A significant advantage of the combinatorial synthesis disclosed in this invention allows very large numbers of sequences to be synthesized on a device (dependent on the number of SPM microlocations). Key to this is the employment of those devices having either individual buffer chamber(s) for each test site or individual control and modulation of the electric field at each reaction zone. The basic concept for combinatorial synthesis capitalizes on the use free field electrophoretic transport to deliver, concentrate, and react monomers, coupling reagents or deblocking reagents at specific addressable microlocations on the device. Alternatively, the electric field can be utilized to protect sites from reaction. Also important to the concept is the identification of selective steps in these chemical synthesis processes where one or more of the reactants has either a net positive or negative charge, or the creation of such suitable reagents for these processes.

One method for combinatorial oligonucleotide synthesis begins with a set of selectively addressable microlocations whose surfaces have been derivatized with blocked primary amine (X—NH—) groups (the specific binding entity). The initial step in the process involves selective deblocking of microlocations using a charged deblocking reagent (the first charged entity). In this case, the reagent would carry a positive (+) charge and would be present in the common first chamber. The process is carried out by applying a negative bias to the second (lower) chamber electrodes specific to individual test site microlocations. Conditions would be chosen to rapidly concentrate the deblocking agent at the specific test sites to a level necessary to achieve rapid and selective deblocking of the desired functional group. In short, application of positive (or in other cases, negative) potentials to selective electrodes causes the charged reagents to be moved from a reagent delivery site or chamber and concentrated at the desired microlocation being de-blocked.

In the second step, chemical coupling of the first base, to the deblocked microlocations is carried out by simply exposing the system to the phosphoramidite reagent (x-base) in the upper chamber. The nucleotide couples to de-blocked entities at the selected microlocations, but not to any of the blocked entities at other microlocations. At this point, standard phosphoramidite chemistry is carried out until the next de-blocking step.

At the second de-blocking step, those electrodes specific to the desired microlocations which are to be coupled with the next base are made negative, as above, and those to be protected are not activated. The system is now exposed to the next base to be coupled, and selective coupling to the de-blocked microlocation is achieved, as above. The coupling and de-blocking procedures are repeated, until all the different DNA sequences have been synthesized at each of the test site microlocations.

3.3.2 Oligonucleotide Synthesis With Terminal Transferase

Another embodiment of the methods of the invention for the combinatorial synthesis of oligonucleotides involves the use of nucleic acid polymerizing enzymes to add nucleotides. This approach utilizes terminal transferase; 3'-monophosphate esters of 5'-deoxyribonucleotide triphosphates, and a phosphatase. Terminal transferase is used to couple the nucleotides. The 3'-phosphate ester serves as a blocking group to prevent the addition of more than one nucleotide in each, coupling step. A 3'-phosphatase is used to remove the 3'-phosphate ester for the next coupling step.

Because all reagents are water soluble and charged, the techniques described above can be used to enhance the steps in this combinatorial synthesis procedure. In this approach, an array is used which has A, T, G, and C nucleotides linked through their 5'-hydroxyl position at the appropriate microlocations on the device (the specific binding entities). These first nucleotides are linked using the electric field enhanced addressing techniques.

The first round of coupling reactions is initiated by biasing the lower chambers positive at all those microlocations which are to be coupled with an adenosine (A) in their second position, while the common upper chamber contains terminal transferase and the 3'-phosphate ester of deoxyadenosine triphosphate (the first charged entities). Notable in this scenario is the presence of an essential cofactor to the reaction, $Mg^+$ (the second charged entity), in the second chamber. The reagents are free field electrophoresed to the appropriate microlocations and concentrated in the reaction zone. The A nucleotide is coupled by the terminal transferase to the first nucleotide on the matrix. Because the nucleotide triphosphates are esterified with a phosphate group in their 3' positions, terminal transferase adds only one nucleotide at a time.

After the nucleotide coupling is complete, the bias is reversed and the enzyme and spent reagents are removed. The process is repeated for the first round coupling of G, C, and T nucleotides until all the microlocations have been coupled.

When first round of coupling (A, T, G and C)is complete, the first buffers replaced with one containing 3'-phosphatase and the 3'-phosphatase is free field electrophoresed and concentrated at the microlocations where it hydrolyses the 3'-phosphate ester. The removal of the phosphate ester leaves the 3'-hydroxyl group ready for the next round of coupling reactions. The coupling reactions are carried out until the desired oligonucleotide sequences are complete at all test site microlocations in the device.

In addition to DNA synthesis, a similar process can be developed for RNA synthesis, peptides synthesis, and other complex polymers.

3.3.3 Electronically Controlled Molecular Biology and Amplification Reactions

A variety of molecular biological reactions including linear and exponential multiplication or amplification of target DNA and RNA molecules can be carried out on these devices using the electric field to concentrate reagents and to non thermally "melt" hybridized structures during the amplification cycles or steps.

Restriction enzyme cleavage restrictions and DNA fragment analysis can be carried out under complete electronic control. Nucleic acid multiplication or amplification reactions with these devices are distinct from other isothermal or thermal cycling amplification procedures (PCR, LCR, SDA), in that a) the rate-limiting nucleic acid hybridization reaction step can be carried out with dramatic rapidity, as described above, and b) enzymes and reagents useful in the enzymatic reactions themselves may be rapidly transported to the reaction zone and/or supplied by the second buffer chamber in simultaneous or subsequent steps. New mechanisms for amplification come directly from the active nature of the use of electric fields to mediate various steps in the process, to concentrate reagents and to selectively denature duplex DNA. That is, the device provides unique electronic mechanisms to: (1) selectively denature nucleic acid hybrids under isothermal reaction conditions and well below their Tm point (thermal melting temperature); (2) rapidly transport or move nucleic acids back and forth between two or more microlocations; and (3) rapidly hybridize these nucleic acids to capture probes/primers on the SPM.

In addition to reducing the time necessary for hybridization of target nucleic acids with primers or capture probes, the devices and methods of the invention can selectively concentrate DNA modifying enzymes, such as, but not limited to, restriction endonucleases, DNA or RNA polymerases, and ligases, at any desired microlocation on the device as well as to control movement of essential cofactors, in particular $Mg^{++}$, for these enzymes in alternate buffer systems (e.g. lower vs. upper chambers). Examples of electronically controlled molecular biology and amplification reactions which can be carried out on the devices include: (1) electronically directed restriction enzyme cleavage of ds-DNA sequences; (2) electronic amplification of target DNA by DNA polymerases; (3) electronic ligation and amplification of target DNA sequences by DNA and RNA ligases; (4) electronic amplification of target RNA by RNA polymerases, and 5) electronic phosphorylation and de-phosphorylation of nucleic acids and proteins by kinases and phosphatases.

As is evident from this discussion, the devices and methods of the invention may be employed to great advantage in DNA or RNA amplification procedures, such as the strand displacement amplification (SDA) procedure illustrated by Example 7, greatly increasing their speed and efficiency. Any other primer-based amplification procedure, such as the thermal-cycle polymerase chain reaction (PCR), ligase chain reaction (LCR), rolling circle amplification, nucleic acid sequence based amplification, and other techniques such as reverse-transcription and transcription mediated amplification (TMA), may be carried out on the device.

3.3.4 Electronic Restriction Fragment Analysis

In addition to carrying out restriction enzyme cleavage of ds-DNA, these devices and electronic techniques can be used to analyze and determine the relative size of DNA fragments. This is possible when DNA fragments with different lengths can be hybridized to a common capture sequence on individual test site microlocations. Or, these methods may be used when DNA fragments of different lengths can be hybridized to different capture sequences, all of which have the same hybridization or binding energy. In these cases, electronic stringency control can be used to selectively de-hybridize the different DNA fragments according to the length of their un-hybridized or overhanging sequence. The electrophoretic force on the fragments with longer overhanging sequences causes them to de-hybridize before the fragments with shorter overhanging sequences. Thus, if the fragments are labeled for detection, and addressed to specific microlocations, their sizes can be determined by the electrophoretic potential or power level required to de-hybridize from the microlocations. Thus, the devices and methods of the invention maybe used to carry out an "electronic" restriction fragment length polymorphism analysis.

3.3.5 Controlled Enzymatic Reactions

Distinct from the DNA manipulations mentioned above, the devices and methods of the invention can be used to accelerate enzymatic reactions by the controlled use of electric fields. The controlled electrophoretic transport of substrates, reagents, enzymes and cofactors from the first and second chambers to the reaction zone allows these devices to mediate the reaction process in a controlled manner. In addition, these devices may also mediate reactions by accelerating discrete steps in a reaction process, such as increasing product release by influence of the electric field or by altering the catalytic environment of the enzyme in the reaction zone.

For instance, mediation of the hexokinase enzyme reaction may be readily achieved in these devices. Hexokinase catalyzes the addition of phosphate onto D-glucose, in which the source of the phosphate is ATP and the enzymatic reaction has an absolute requirement for $Mg^{++}$ as a cofactor. In an illustrative method, hexokinase is bound within the reaction zone on the SPM as the specific binding entity. The transport of reagents to the reaction zone is mediated by electric field transport to the reaction zone of ATP (the first charged entity) from the first buffer chamber and $Mg^{++}$ (the second charged entity) from the second buffer chamber. Glucose, being uncharged, is not governed by the presence of the electric field however, its negatively charged product, glucose 6-phosphate, is. Therefore, the charged product of the reaction may be drawn into the SPM or the second buffer chamber by the electric field. Thus, precise control of the enzymatic process would be achieved. Applications arising from enzymatic manipulations of this sort include derivatizing test compounds (e.g. enzymatic based synthesis), and radioactively labeling (and subsequently separating labeled material from the starting reagents) biomolecules for subsequent quantification.

One might readily extend this to the employment of non-organic catalysts located within the reaction zone of the test site microlocation. In these applications, novel chemistries and reactions light take place under the concentration of reagents from the two chambers. A further embodiment may have linked reactions within the same reaction zone. Alternatively, steps of a complex reaction could be linked by utilizing electronic control of the microlocations utilized to move the reactants from one reaction zone to the next in serial fashion.

3.3.6 Improved Antibody or Affinity Based Reactions

Improved performance of competition assays utilizing antibodies may also be accomplished using the devices and methods of the invention. Some improvements in assay performance may be decreased time for coupling between antigen and primary antibody in the reaction zone (from hours to minutes or seconds) due to the concentration of reactants in reaction zone by the applied electric field. Antibody reactions may be further improved, using the devices of the invention by the ability to link the steps of binding to those of detection.

One example of the linkage of binding and detection reactions are improved competitive assays using the devices of the invention. One embodiment of this is having, in each first chamber, a first charged unknown or test antigen mixed with a defined quantity of known standard (also a first charged entity). The known standard is capable of binding to the primary antibody located in the reaction zone (the specific binding entity) in a competitive fashion to that of the charged unknown. Upon application of the electric field and electronic concentration of the various first charged entities within the reaction zone, a competition between unknown test antigens and the standard at the primary antibody occurs. The bias is reversed and non-bound materials, e.g., non-bound standard, is removed.

The buffer in the first chamber is then replaced with components suitable for signaling the presence of the standard (without interference to the binding domain recognized by the primary antibody). An example might be a second antibody linked to a chemiluminescent enzyme, e.g., luciferase. Again, a bias applied across the reaction zone would concentrate the antibody-enzyme species at the reaction zone where it binds to all standards within the test site microlocation. The buffers in both chambers are then exchanged to include the necessary components for the luminescent signaling reaction, e.g., ATP in the first chamber and $Mg^{++}$ in the second. Application of the appropriate bias across the reaction zone results in a rapid concentration of reactants and enzymes in this location, producing the luminescent signal. Therefore, the overall process of competitive enzyme linked immunoassays is shortened from hours to minutes in this invention, and the amount of reagents (antigen standards labeled antibodies, ATP, etc.) may also be significantly reduced.

The invention has the further advantage of reusability. That is, bound antigen or standard may be readily removed by the use of buffers with suitable characteristics (e.g., presence of detergents and pH selected to weaken binding of the antigen or standard without harm to the antibody itself) and the application of electric fields. This aspect is not readily achievable in standard microtiter plate based assays.

EXAMPLES

The following examples are offered to further illustrate the various aspects of the present invention, and are not meant to limit the invention in any fashion. Based on these examples, and the preceding discussion of the embodiments and uses of the invention several variations of the invention will become apparent to one of ordinary skill in the art. Such self-evident alterations are also considered to be within the scope of the present invention.

The recipes for buffers, solutions, and media in the following examples are described in J. Sambrook, E. F. Fritsch, and T. Maniatis, *Molecular Cloning: A Laboratory Manual*, 2 Ed., Cold Spring Harbor Laboratory Press, Cold Spring Harbor, N.Y. 1989. All referenced patents, articles, and publications mentioned in this specification are explicitly incorporated by reference in their entirety.

Example 1

Semipermeable Matrix Preparation

Streptavidin-agarose Preparation 2.5% glyoxal agarose (Bio Whittaker) was prepared in water per manufacturer's instructions. Agarose solution was incubated at 60° C. until ready to use. Streptavidin (Boehringer Mannheim) was dissolved in 100 mM sodium phosphate, pH 7.4 to a final concentration of 5 mgs/ml. Fresh 200 mM sodium cyanoborohydride in sodium phosphate, pH 7.4 was prepared. Streptavidin-agarose (4:1), was mixed and incubated at 60° C. for 2 minutes.

Gels were cast in either cut down Pasteur pipettes (~5 mm diameter gel tubes) or 1 mm holes drilled into an ABS plastic plate (for the device shown in FIG. 10). Pipettes received 150 microliters, and sample plate holes received 5 microliters of SA-GA. After gelling, cyanoborohydride solution was pipetted over the top of the gels and the reduction reaction allowed to proceed for 2 hrs at room temperature or 16 hrs at 4° C.

Streptavidin-polyacrylamide Preparation

PEG-Streptavidin Synthesis:

A solution of 500 mg streptavidin in 20 ml PBS buffer and 150 mg Acrylic-PEG-NHS linker in 10 ml PBS buffer were mixed and slowly stirred at room temperature for 1–2 hrs. The mixture was then dialyzed overnight in 50 mM phosphate buffer pH 7.4 and 500 mM NaCl followed by 50 mM phosphate buffer and 150 mM NaCl. The dialyzed product was concentrated in centrifuge to obtain the desired concentration.

Gel Preparation:

Aliquots of Monomer Solutions Were Prepared by Mixing:

- 30 or 60 microliters of a 40:5 acrylamide/bis-acrylamide solution in water
- 6 microliters of a 1.9% Darocur 4265 solution in DMSO
- 15 microliters DMSO
- 10.8 microliters of a 17% PEG-streptavidin solution in phosphate buffer
- 58.2 or 28.2 microliters water to reach a total volume of 120 microliters Small amounts (0.5–3 microliters) of freshly prepared monomer solution were introduced into vertically drilled through-holes (0.4–1.5 mm diameter) in a black plastic sheet (0.2–0.4 mm thick acrylic or ABS) and exposed to UV light on both sides for 20–30 sec. After polymerization the gel-filled plastic sheets were stored in 25–50 mM phosphate buffer pH 7.4 until further use.

Example 2

Electronic Hybridization and Dehybridization

Figure 12:
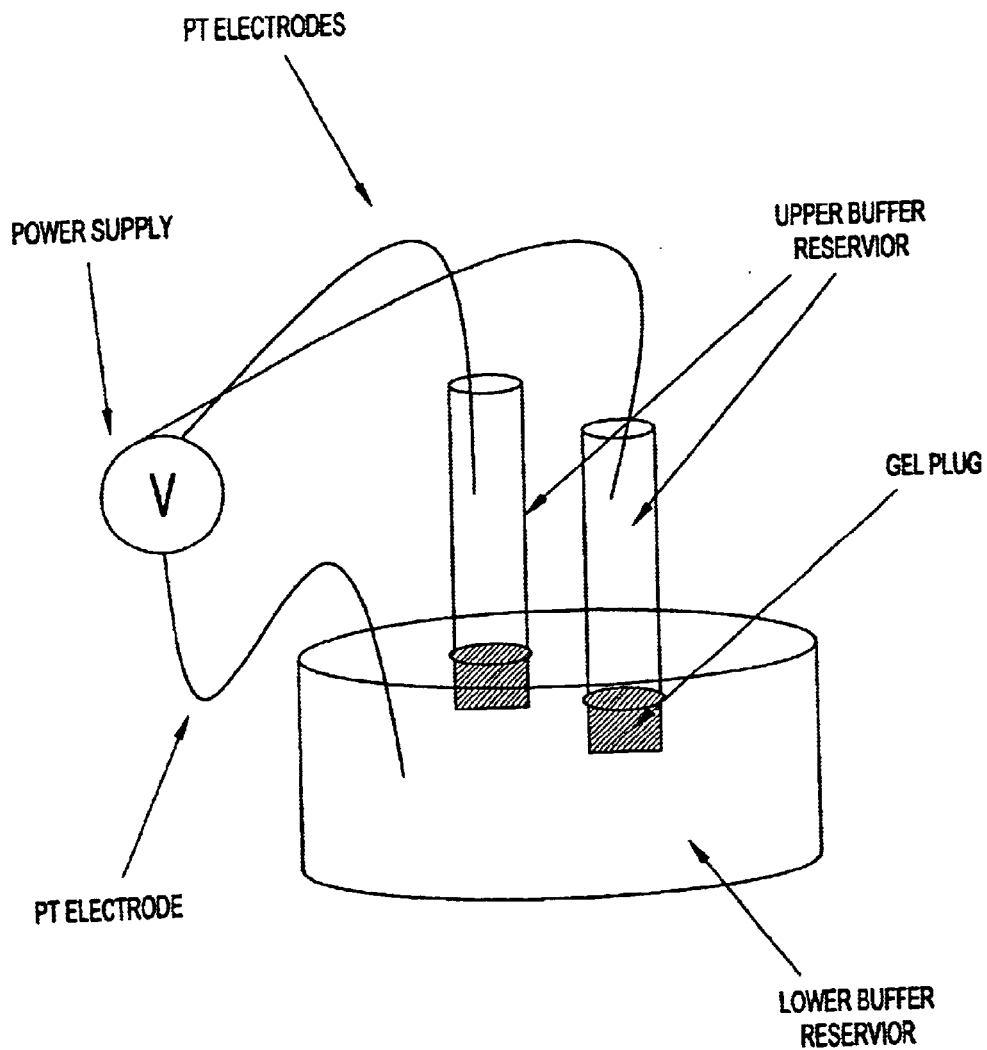
FIG. 12: Second Functional Prototype Device. Schematic of a prototype device utilizing the "gel tube" format. Gel tubes were produced from 5 mm diameter pipettes as described in Example 1. This device was utilized in Examples 2 and 3.

For this example, the gel tube apparatus illustrated in FIG. 12 was used with an agarose/streptavidin SPM synthesized as described in Example 1.

Attachment of Capture Oligonucleotides (Specific Binding Entity):

Upper and lower buffer reservoirs were filled with 50 mM histidine, pI. Specific capture ATA5 (5'biotin-GATGAGCAGT TCTACGTGG [SEQ. ID NO. 1]) or nonspecific ATA4 (5'biotin-GTCTCCTTCC TCTCCAG [SEQ. ID NO.2]) oligos were pipetted onto the top of the gel (5 microliters 500 nM in 50 mM histidine, pI, 10% glycerol). The lower buffer reservoir was biased positive and the oligos electrophoresed into the gel for 2 minutes, 20V using a Bio-Rad PowerPac 1000 power supply. Reversing the bias for 2 minutes effected an electronic wash. Gel tubes were then rinsed in histidine buffer, pI.

Hybridization:

Upper buffer chamber was filled with 50 mM histidine, pI and the lower buffer was filled with 100 mM histidine, pH 5. BodipyTR labeled RCA5 reporter (5'btr-CCACGTAGAA CTGCTCATC [SEQ. ID NO.3]) at 100 nM in loading buffer (50 mM histidine, pI, 10% glycerol) was loaded onto the test sites with gel tubes containing specific or nonspecific attached capture oligonucleotides and electrophoresed for 2 minutes, 20V. The lower reservoir electrode was biased positive. An electronic wash was performed for the same amount of time by revering the electric field bias at the same voltage. The gel tubes were rinsed in 50 mM histidine, pI and visualized under an epifluorescent microscope (Jena). Images were acquired and stored digitally using a Sony digital recorder. A similar experiment was repeated using histidine pI in both upper and lower reservoir chambers.

Dehybridization:

Upper and lower buffer reservoirs were filled with 20 mM sodium phosphate, pH 7.4. The upper reservoir electrode was biased positive and the gels were electrophoresed for 2–5 minutes at increasing voltage levels starting at 20 V. After each step, signal on the specific and nonspecific gel tubes was quantified and fresh buffer was added to the reservoirs.

Results:

Specific hybridization signal was observed after electronic hybridization in the $HIS_{pI}/HIS_{pH\ 5}$ but not in the $HIS_{pI}/HIS_{pI}$ buffer system. This indicates that protonated histidine (cation) is necessary to stabilize DNA hybridization. By reversing the bias, nonspecific signal was removed after biasing 2 minutes, 40V in 20 mM sodium phosphate, pH 7.4.

| Intensity | $HIS_{pI}/HIS_{pH\ 5}$ | $HIS_{pI}/HIS_{pI}$ | Dehybridization |
|---|---|---|---|
| Specific ATA5 | 94 | 16 | 5 |
| Nonsp. ATA4 | 4 | 14 | nd |

Example 3

SNP Mutation Discrimination in H-Ras System

For this example, the gel tube apparatus illustrated in FIG. 12 was used with an agarose/streptavidin SPM synthesized as described in Example 1.

Capture:

Ras G wild type and Ras T mutant captures are loaded as per Example 2.

(RAS G: 5'biotin-CACACCGGCG GCGCC [SEQ. ID NO.4],

RAS T: 5'biotin-CACACCGTCG GCGCC [SEQ. ID NO. 5])

Hybridization:

As per example 2 using BodipyTR labeled Ras C reporter complement (5'btr-GGCGCCGCCG GTGTG [SEQ. ID NO. 6].

Stringency/Dehybridization:

As per example 2.

Results:

Hybridization signal was observed on both wild type and mutant gel caps before reversing the bias. By reversing the bias, mismatch signal was selectively removed after biasing 5 minutes, 70 V in 20 mm sodium phosphate, pH 7.4. A discrimination ratio of 79:1 was obtained.

|           | Initial Intensity | Final Intensity |
|-----------|-------------------|-----------------|
| Wild type | 164               | 79              |
| mutant    | 134               | 1               |

Example 4

Electronic Dot Blot With PCR Amplicons

For this example, the apparatus illustrated in FIG. 10 as used with an agarose/streptavidin SPM synthesized as described in Example 1.

Haemochromatosis patient samples were amplified using AmpliTaq protocols. Primer sequences were: forward primer 1947, 5'biotin-TGAAGGATAA GCAGCAAT [SEQ. ID NO. 7] and reverse primer 1948, 5'TCCTCTCAAC CCCCAATA [SEQ ID NO. 8]. The products (229 bp) were analyzed by 12.5% PAGE (Novex) and purified using Qia-Prep kit (Qiagen), eluted in 50 µl water.

Target:

The biotinylated amplicon was diluted 1/10 in 50 mM histidine, pI, denatured at 95° C., 10 minutes and then snap cooled on ice. Glycerol was added to 10% final concentration and 5 µl was applied to each streptavidin-agarose plug on the macro-hybridization device. ATA4 is used as a nonspecific control. Addressing conditions as in Example 2 where only the biotinylated single stranded target remains bound to the streptavidin-agarose Hybridization:

As per Example 2 using a BodipyTR labeled reporter (5'AGGGGCTGAT CCAGGCCTGG GTGCTCCACC TGGCAC-btr [SEQ. ID NO. 9]). Hybridization and wash voltages were reduced to 5 V due to the reduced test site diameters.

Results:

PCR generated targets were electronically loaded and hybridized in less than 10 minutes. Specific signal was easily detected over nonspecific or background signal.

|             |    |
|-------------|----|
| Specific    | 40 |
| nonspecific | 4  |

Example 5

Hybridization Kinetics on the Mycrohyb Device

For this example, the apparatus illustrated in FIG. 10 was used with an agarose/streptavidin SPM synthesized as described in Example 1.

Capture:

As described, in Example 2 except, the macro-hybridization device was used and ATA5 specific or ATA4 nonspecific captures were loaded for 60 seconds, 5V.

Hybridization:

As described in Example 2, except 5 nM btr-RCA5 reporter was either electronically hybridized for 30 seconds, 5V or passively hybridized at room temperature for 30 seconds to 16 hours. Upper and lower reservoir buffers were 50 mM $HIS_{pI}/HIS_{pI}$, $HIS_{pI}/HIS_{pH\,5}$, $HIS_{pH\,5}/HIS_{pH\,5}$ or 100 mM $NaP_{pH\,7.4}/NAP_{pH\,7.4}$ (sodium phosphate, pH 7.4).

Dehybridization:

Electronic wash was performed in 20 mM $NaP_{pH\,7.4}$, 30 seconds, 10V.

Results:

Comparison of active vs. passive hybridization kinetics in various buffer combinations indicate that 30s electronic hybridization in 50 mM $HIS_{pI}/HIS_{pH\,5}$ is roughly equivalent to 16 hours of passive hybridization in a more conventional buffer, 100 mM $NaP_{pH\,7.4}/NAP_{pH\,7.4}$. Thus under these buffer conditions with this set of DNA sequences for hybridization, the hybridization reaction using a device of the invention was accelerated by factor of about 1900 as compared to the passive hybridization reaction in a traditional high salt buffer.

|         |      |     | $HIS_{pI}/HIS_{pI}$ | $HIS_{pI}/$ $HIS_{pH\,5}$ | $HIS_{pH\,5}/$ $HIS_{pH\,5}$ | $NaP_{pH\,7.4}/$ $NAP_{pH\,7.4}$ |
|---------|------|-----|---------------------|---------------------------|------------------------------|---------------------------------|
| Passive |      |     |                     |                           |                              |                                 |
| 30 s    | ATA5 | sp  | 15                  | 5                         | 2                            | 7                               |
|         | ATA4 | nsp | 0                   | 4                         | nd                           | 8                               |
| 300 s   | ATA5 | sp  |                     |                           |                              | 8                               |
|         | ATA4 | nsp |                     |                           |                              | nd                              |
| 1 hr    | ATA5 | sp  |                     |                           | 20                           | 28                              |
|         | ATA4 | nsp |                     |                           | 15                           | 3                               |
| 16 hrs  | ATA5 | sp  |                     |                           |                              | 55                              |
|         | ATA4 | nsp |                     |                           |                              | 6                               |
| Active  |      |     |                     |                           |                              |                                 |
| 30 s    | ATA5 | sp  | 15                  | 48                        | 3                            |                                 |
|         | ATA4 | nsp | 10                  | 7                         | 0                            |                                 |

Background (~40 rfu) was subtracted from all values.
nd = not done.

Example 6

Electronic Hybridization and De-hybridization on the Macrohyb Device

For this example, the apparatus illustrated in FIG. 10 was used. Streptavidin-polyacrylamide gels were prepared according to the recipe above using 60 microliters of 40:5 acrylamide/bis-acrylamide in water.

Passive Capture Load:

Biotinylated capture probes ATA7 (5'-TTCCACAGAC TTAGATTTGA C [SEQ. ID NO. 10]) and GH26 (5'-GTGCTGCAGG TGTAAACTTG TACGAG [SEQ. ID NO. 11], 2 µM in 2×SSC) were loaded by passive incubation (60 min). After incubation the gels were rinsed with 25–50 mM phosphate buffer pH 7.4 and stored in the same medium until further use.

Electronic Hybridization:

The lower buffer chamber of the macrohyb device was first filled with 50 mM L-histidine pH 5 ($HIS_{pH\,5}$). The upper buffer chamber was filled with a solution of 50 nM Bodipy-TR labeled RCA7 (5'btr-GTCAAATCTA AGTCTGTGGA A [SEQ. ID NO. 12]) in 50 mM L-histidine. ATA7 and GH26 loaded gels were electronically hybridized for 5 min at +5 V (0.25–0.2 mA).

De-hybridization:

Both upper and lower buffer chambers were emptied and refilled with 25 mM phosphate buffer pH 7.4. Non-specifically bound target oligonucleotides were removed by application of −5 V(−1.6 mA) for 9 min.

Figure 11:
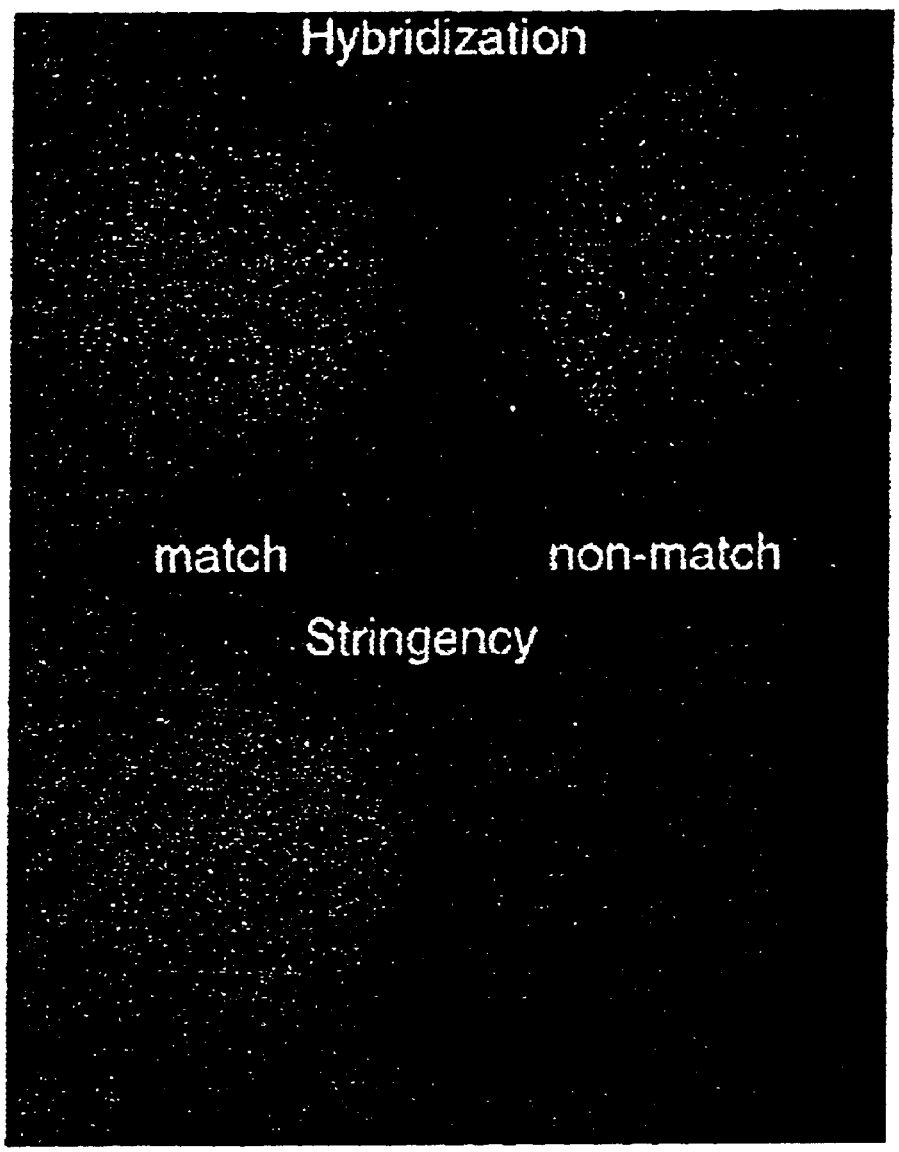
FIG. 11: Hybridization of DNA Utilizing the Device. Hybridization result before and after electronic stringency performed as described in Example 6 on a twelve-test-site device as depicted in FIG. 10, using streptavidin-acrylamide SPMs Nonspecific signal is significantly reduced relative to specific hybridization signal. Intensity scale between hybridization and stringency panels was not normalized.

Results (See Also FIG. 11):

| Intensity* | $HIS_{pI}/HIS_{pH\,5}$ | De-hybridization |
|---|---|---|
| ATA7 loaded gel | 42 | 31 |
| GH26 loaded gel | 48 | 2 |

Example 7

Factor V Anchored SDA Amplification

Figure 13:
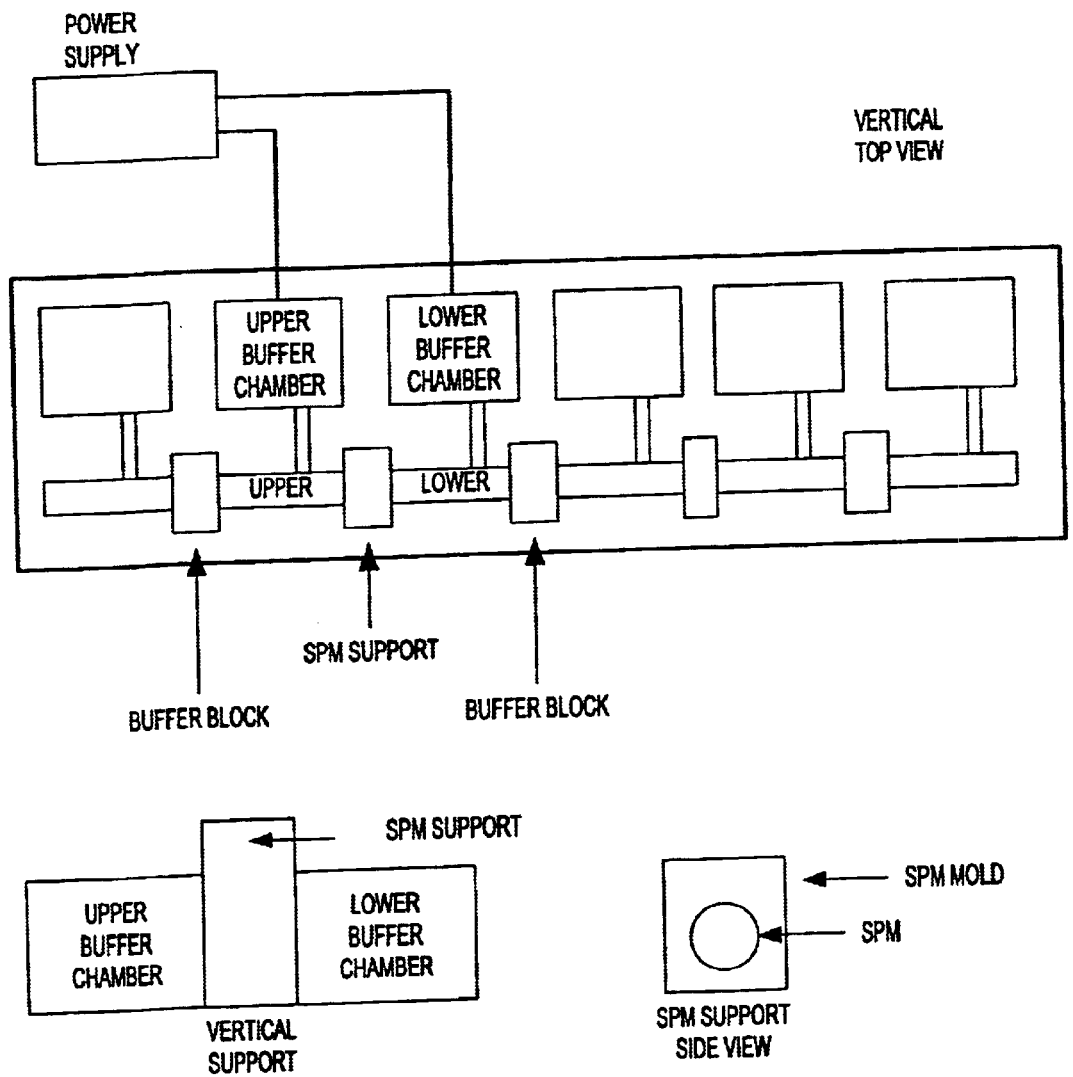
FIG. 13: Vertical Embodiment of A Third Functional Prototype Device. The schematic of a working prototype with a vertical SPM support is shown. This device was used for DNA amplification on the SPM after electronic hybridization of target DNA in Example 7.

The device shown in FIG. 13, 14 cm×5 cm with a vertical SPM support, was used for this example. Streptavidin-agarose was prepared as described above. As shown in the schematic, acrylic buffer blockers (Buffer block; 2 cm×1.3 cm) define the working buffer chambers and distance of the SPM from the electrodes. Multiple reactions can be carried out in the apparatus by placing buffer blockers between SPM supports and physically separating buffer components. The larger (2 cm×1.5 cm×1.5 cm) upper and lower buffer chambers contain electrodes which connect to an external power supply. The smaller (1.5 cm×0.3 cm×0.5 cm) upper and lower buffer chambers are connected to the larger buffer chambers via smaller channels milled into the one-piece plastic apparatus. This allows a reduction in sample volume (approximately 200 µl) needed for electronic addressing and hybridization. The SPM support is a two piece acrylic mold that sandwiches a 0.2 µm Micropore filter (0.8 cm in diameter). Streptavidin agarose is poured on top of the micropore filter to completely fill the mold. The resulting SPM plug is approximately 1–2 mm thick. The SPM support is placed in the vertical apparatus such that the SPM plug faces the upper buffer chamber. The lower buffer chamber is in contact with the bottom of the micropore filter in the SPM support.

SDA Primer and Bumper Sequences Used:
  Factor V sense SDA: 5'biotin-ACCGCATCGA ATGCAT-GTCC TCGGGTCTCT GGGCTAATAG GA [SEQ ID NO. 13]
  Factor V antisense SDA: 5'-biotin-ACGATTCAGC TCCAGACTTC TCGGGTCAGA ATTTCTGAAA GG [SEQ. ID NO. 14]
  Factor V bumper sense: ACTACAGTGA CGTGGA-CATC [SEQ. ID NO. 15]
  Factor V bumper antisense: TGTTATCACA CTGGT-GCTAA [SEQ ID NO. 16]
  Factor V reporter: 5'btr-ACTTCTAATC TGTAAGAG-CAG [SEQ. ID NO. 17]

Primer Load:
  The electrophoresis apparatus was assembled, and filled with 50 mM histidine, pI. The upper reservoir buffer was then replaced with 0.5 µM biotinylated SDA primers (FacV) in 50 mM histidine, pI. The primers were electrophoresed at 33 volts for 15 minutes to bind biotinylated primers to the streptavidin agarose SPM. The device was then washed extensively with 50 mM histidine to remove unattached SDA primers.

Hybridization:
  Template DNA (FacV PCR amplicon; 1:100) was denatured at 95° C. for 5 minutes in 50 mM histidine, pI. The lower reservoir buffer was replaced with 50 mM histidine buffer (pH 5.0). The template DNA was then electrophoresed at 33 volts for 10 minutes to hybridize template DNA to bound SDA primers. The device was then washed extensively with 50 mM histidine, pI to remove non-hybridized template DNA.

SDA Amplification:
  The SDA reaction was performed for 45 minutes at 60° C. (6 mM MOPS, pH 7.8, 1.7 mM each dCTP αS, dTTP, dATP and dGTP, 85 mM KCl, 18 mM MgCl$_2$, 23 mM NaCl, 3.5 mM Tris-HCl, pH 7.9, 0.035 mM dithiothreitol (DTT), 1.5 units BsoBI, 0.8 units BstI polymerase and 25 nM each bumper primer). The device was then washed with 0.5×SSC, pH 7.0, then washed with 0.5×SSC, pH 12.5 for 4 minutes, and finally washed with 0.5×SSC, pH 7 and 4×SSC. The SPM was then incubated with reporter oligonucleotide (factor V 1321; <10 µM in 4×SSC) in the first buffer chamber. After washing extensively with 4×SSC and incubating with 0.2×SSC/1.0% SDS to remove unbound reporter oligonucleotide, the SPM was imaged with appropriate lasers and filters Results:
  In this experiment, a 1:1100 dilution of factory V PCR amplicon (+template) was hybridized onto anchored SDA primers in the macro-agarose plug. After amplification, the SDA amplicon products were denatured, hybridized with fluorescent (Bodipy Texas Red) reporter oligonucleotide and visualized with the appropriate lasers and filters. A negative control consisting of no template hybridization (−template) was used to determine if amplification took place. A fluorescent signal was seen only in the presence, but not in the absence of template DNA. The MFI values in the presence of template were approximately 2.5 times higher than in the absence of template DNA. This experiment demonstrates that DNA amplification by enzymatic processes can be performed on electronically hybridized target DNA using the devices and methods of the invention.

Example 8

Support Materials for Use in Fabrication of the Devices of the Invention

To select appropriate plastic, substrates of low fluorescent background, different plastic substrates were tested as to their fluorescent characteristics 600 nm. The plastics were tested by an epifluorescent microscope imaging system and by a fluorometer. The following table provides the list of substrates and fluorescent readings obtained from an LS50B fluorometer:

| Plastic Substrate | | Intensity at 610 nm, 5 sec int. |
|---|---|---|
| ABS | black | 0.140 |
| | white | 6.811 |
| Polystyrene | | 7.955 |
| Acrylic | clear | 0.169 |
| | white | 51.77 |
| | tinted | 0.151 |
| | black | 0.035 |
| | transwhite | 51.22 |
| UHMW | black | 0.743 |
| | white | |
| Delrin | black | 1.834 |
| | white | 61.39 |
| TFE | | 96.05 |
| Polypropylene | white | 22.18 |
| | natural | 25.82 |
| Polycarbonate | clear | 11.32 |
| | tinted | 3.103 |
| | white | 45.31 |
| | black | 0.156 |
| PVC | gray | 2.667 |

The experiments show that black acrylic ABS, and polycarbonate have the lowest fluorescence background levels.

We claim:

1. A device for the modulation of a reaction comprising:
a first buffer reservoir containing a first buffer and a first charged entity, wherein the first buffer has an initial conductance less than 1000 $\mu$S/cm;
a second buffer reservoir separated from the first buffer reservoir containing a second buffer comprising a second charged entity, wherein the second charged entity has a charge opposite that of the first charged entity, the second charged entity modulates the specific reaction between the specific binding entity and the first charged entity;
a conductive semipermeable matrix contained in a non-conductive support material, the conductive semipermeable matrix disposed between and fluidically connecting the first buffer reservoir and the second buffer reservoir;
a first electrode linked to a power source and located in the first buffer reservoir and contacting the first buffer; and
a second electrode linked to the power source and located in the second buffer reservoir and contacting the second buffer; and
a specific binding entity which reacts specifically with the first charged entity and which is physically fixed on, in, or adjacent to the semipermeable matrix.

2. The device of claim 1 comprising a common first buffer reservoir connected through a plurality of semipermeable matrices to a common second buffer reservoir.

3. The device of claim 1 further comprising a plurality of first buffer reservoirs connected through a plurality of semipermeable matrices to a common second buffer reservoir.

4. The device of claim 1 further comprising a plurality of first buffer reservoirs connected through a plurality of semipermeable matrices to a plurality of second buffer reservoirs.

5. The device of claim 1 further comprising a common first buffer reservoir connected through a plurality of semipermeable matrices to a plurality of second buffer reservoirs.

6. The device of claim 1 comprising a common first electrode and a common second electrode.

7. The device of claim 1 further comprising a plurality of first electrodes and a common second electrode.

8. The device of claim 1 further comprising a common first electrode and a plurality of second electrodes.

9. The device of claim 1 further comprising a plurality of first electrodes and a plurality of second electrodes.

10. The device of claim 1 wherein the specific binding entity is attached through a covalent or non-covalent bond to a portion of the semipermeable matrix comprising at least the portion of the semipermeable matrix at or around the first-buffer-side of the semipermeable matrix.

11. The device of claim 1 wherein the initial conductance of the first buffer is in the range of 0.1 to 250 $\mu$S/cm.

12. The device of claim 1 wherein the initial conductance of the first buffer is in the range of 0.1 to 100 $\mu$S/cm.

13. The device of claim 1 wherein the initial conductance of the first buffer is in the range of 0.1 to 50 $\mu$S/cm.

14. The device of claim 1 wherein the concentration of the buffer species in the first buffer is in the range of 10 mM to 300 mM.

15. The device of claim 1 wherein the concentration of the buffer species in the first buffer is in the range of 25 mM to 200 mM.

16. The device of claim 1 wherein the ratio of the initial concentration of the second charged entity in the first buffer to the initial concentration of the second charged entity in the second buffer is less than 1:1.

17. The device of claim 1 wherein the ratio of the initial concentration of the second charged entity in the first buffer to the initial concentration of the second charged entity in the second buffer is less than 1:10.

18. The device of claim 1 wherein the ratio of the initial concentration of the second charged entity in the first buffer to the initial concentration of the second charged entity in the second buffer is less than 1:100.

19. The device of claim 1 wherein the ratio of the initial concentration of the second charged entity in the first buffer to the initial concentration of the second charged entity in the second buffer is less than 1:1000.

20. The device of claim 1 wherein the first buffer comprises a zwitterionic buffer.

21. The device of claim 20 wherein the zwitterionic buffer is chosen from the group consisting of β-alanine, taurine, cysteine, histidine, methylhistidine, lysine, γ-amino butyric acid, glycine, ε-amino caproic acid, and carnosine buffers.

22. The device of claim 20 wherein the zwitterionic buffer is a histidine buffer.

23. The device of claim 1 wherein the second charged entity is more than one charged species.

24. The device of claim 23 wherein the each of the charged species comprising the second charged entity has approximately the same rate of migration through the semipermeable matrix when an electric potential is applied across the semipermeable matrix.

25. The device of claim 23 wherein the each charged species comprising the second charged entity has a significantly different rate of migration through the semipermeable matrix when an electric potential is applied across the semipermeable matrix.

26. The device of claim 1 wherein the first charged entity is more than one charged species.

27. The device of claim 1 wherein the first charged entity is a nucleic acid polymer.

28. The device of claim 27 wherein the specific binding entity is a nucleic acid polymer.

29. The device of claim 1 wherein the specific binding entity is a polypeptide.

30. The device of claim 1 wherein the first charged entity is a polypeptide.

31. The device of claim 1 wherein the second charged entity is a cation.

32. The device of claim 31 wherein the cation is chosen from the group consisting of positively charged amino acids, positively charged oligopeptides, metal cations, organically chelated metal cations, positively charged detergents, and positively charged amines.

33. The device of claim 31 wherein the cation is protonated histidine.

34. The device of claim 33 wherein the cation is selected from the group consisting of $Na^+$, $K^+$, $Ag^+$, $Cu^+$, $Mg^{+2}$, $Ca^{+2}$, $Zn^{+2}$, $Cu^{+2}$, $Ni^{+2}$, $Co^{+2}$, $Fe^{+2}$, $Se^{+2}$, $Mn^{+2}$, $Al^{+3}$, $Cr^{+3}$, $Fe^{+3}$, $Co^{+3}$, $Mn^{+4}$ and $Se^{+4}$.

35. The device of claim 1 wherein all first electrodes and second electrodes are connected to a power source which controls the voltage of the electrodes in parallel.

36. The device of claim 9 wherein the plurality of first electrodes and second electrodes are connected to a power source which controls the voltage of the electrodes in series.

37. The device of claim 9 wherein the plurality of first electrodes and second electrodes are connected to a power source which controls the voltage of the electrodes independently.

38. The device of claim 9 wherein the plurality of first electrodes and second electrodes are connected to a power source which controls the current through the electrodes in parallel.

39. The device of claim 9 wherein the plurality of first electrodes and second electrodes are connected to a power source which controls the current through the electrodes in series.

40. The device of claim 9 wherein the plurality of first electrodes and second electrodes are connected to a power source which controls the current through the electrodes independently.

41. The device of claim 9 wherein the plurality of first electrodes and second electrodes are connected to a power source which controls the power to the electrodes in parallel.

42. The device of claim 9 wherein the plurality of first electrodes and second electrodes are connected to a power source which controls the power to the electrodes in series.

43. The device of claim 9 wherein the plurality of first electrodes and second electrodes are connected to a power source which controls the power to the electrodes independently.

44. The device of claim 1 wherein the first electrodes and second electrodes comprise a material chosen from the group consisting of as aluminum, gold, silver, tin, platinum, titanium, copper, palladium, iridium, conductive polymers, conductive metal alloys, and carbon.

45. The device of claim 1 wherein the first electrodes and second electrodes comprise platinum.

46. The device of claim 1 wherein the semipermeable matrix is contained within a support material selected from the group consisting of glass, polymers, rubber, ceramics, and combinations thereof.

47. The device of claim 1 wherein the semipermeable matrix is contained within a support material that produces a low background signal.

48. The device of claim 46 wherein the support material is a black-colored organic polymer material with a low fluorescence signal.

49. The device of claim 46 wherein the support material is a low-fluorescence silica glass.

50. The device of claim 1 wherein the semipermeable matrix comprises a single layer of material.

51. The device of claim 50 wherein the single layer of material is substantially uniform throughout the semipermeable matrix.

52. The device of claim 50 wherein the single layer of material is chemically modified at or near the first-buffer-side surface of the semipermeable matrix for the attachment of a specific binding entity.

53. The device of claim 50 wherein the single layer of material consists of a composite material.

54. The device of claim 1 wherein the semipermeable matrix comprises a plurality of material layers.

55. The device of claim 54 wherein the semipermeable matrix comprises a membrane layer.

56. The device of claim 55 wherein the membrane has an pore size limit which is slightly greater than the radius of gyration of the first charged entity.

57. The device of claim 55 wherein the membrane has a molecular weight cutoff between 1 kilodalton and 10 kilodaltons.

58. The device of claim 55 wherein the membrane has a molecular weight cutoff between 3 kilodaltons and 5 kilodaltons.

59. The device of claim 55 wherein the membrane has a pore size limit which is between 1 nm and 10 nm.

60. The device of claim 55 wherein the membrane has a charged surface.

61. The device of claim 60 wherein the membrane has a negatively charged surface.

62. The device of claim 60 wherein the membrane has a positively charged surface.

63. The device of claim 55 wherein the membrane provides sites for the attachment of the specific binding entity.

64. The device of claim 1 wherein the semipermeable matrix comprises a sedimentation layer.

65. The device of claim 64 wherein the sedimentation layer is bounded on only one side by another layer of the semipermeable matrix.

66. The device of claim 64 wherein the sedimentation layer comprises a material chosen from the group consisting of metallic microspheres, silica, chromatography resins, and polymer microspheres.

67. The device of claim 1 wherein the semipermeable matrix comprises at least one material chosen from the group consisting of organic hydrogels, sol-gels, aero-gels, fritted glass, porous glass, chromatographic resins, porous silicon, cross linked polymers, and membranes.

68. The device of claim 67 wherein the organic hydrogel is chosen from the group consisting of polyacrylamide gels and carbohydrate gels.

69. The device of claim 67 wherein the chromatographic resin is chosen from the group consisting of charged chromatographic resins and size-exclusion pore chromatographic resins.

70. The device of claim 69 wherein the charged chromatographic resin is an anionic chromatographic resin.

71. The device of claim 69 wherein the charged chromatographic resin is a cationic chromatographic resin.

72. The device of claim 67 wherein the membrane is chosen from the group consisting of cellulose membranes, nitrocellulose membranes, nylon membranes, chitosan membranes, polycarbonate membranes, and DEAE membranes.

73. The device of claim 1 further comprising a microprobe at the first-buffer-side surface of the semipermeable matrix which is capable of detecting the concentration of the second charged entity at and around the first-buffer-side surface of the semipermeable matrix.

74. The device of claim 73 wherein the microprobe measures pH at and around the first-buffer-side surface of the semipermeable matrix.

75. The device of claim 73 wherein the microprobe measures conductance at and around the first-buffer-side surface of the semipermeable matrix.

76. The device of claim 73 wherein the microprobe is connected to a microprocessor which controls the first electrodes and second electrodes.

77. The device of claim 1 further comprising a microprobe at the first-buffer-side surface of the semipermeable matrix which is capable of detecting the concentration of the product of a reaction between the first charged entity, the second charged entity, and the specific binding entity, at and around the first-buffer-side surface of the semipermeable matrix.

78. The device of claim 77 wherein the microprobe measures pH at and around the first-buffer-side surface of the semipermeable matrix.

79. The device of claim 77 wherein the microprobe measures conductance at and around the first-buffer-side surface of the semipermeable matrix.

80. The device of claim 77 wherein the microprobe is connected to a microprocessor which controls a voltage regulator which controls the first electrodes and second electrodes.

81. The device of claim 1 wherein the second buffer reservoir is a common second buffer reservoir for all semipermeable matrices, and the second electrode is a common second electrode for all semipermeable matrices, and wherein the device further comprises a set of baffles in the second buffer reservoir.

82. The device of claim 1 wherein the semipermeable matrix is so composed as to inhibit free diffusion of molecules between the first and second buffer reservoirs.

83. The device of claim 1 wherein the semipermeable matrix is so composed that there is little or no migration of the first charged entity through the semipermeable matrix into the second buffer reservoir during the time necessary to complete the biochemical reaction in the absence or presence of an electric potential across the semipermeable matrix.

84. The device of claim 1 wherein the semipermeable matrix is so composed that there is little or no migration of the second charged entity through the semipermeable matrix into the first buffer reservoir during the time necessary to complete the biochemical reaction in the absence of an electric potential across the semipermeable matrix, but so that there is controlled migration of the second charged entity through the semipermeable matrix in the presence of an electric potential across the semipermeable matrix.

85. The device of claim 1 wherein the first electrode is negatively biased.

86. The device of claim 1 wherein the second electrode is positively biased.

* * * * *